US007763620B2

(12) United States Patent
Hamilton et al.

(10) Patent No.: US 7,763,620 B2
(45) Date of Patent: Jul. 27, 2010

(54) PIPERAZINONE COMPOUNDS AS ANTI-TUMOR AND ANTI-CANCER AGENTS AND METHODS OF TREATMENT

(75) Inventors: Andrew D. Hamilton, Guilford, CT (US); Said Sebti, Tampa, FL (US); Hairuo Peng, Chestnut Hill, MA (US)

(73) Assignees: Yale University, New Haven, CT (US); University of South Florida, Tampa, FL (US)

( * ) Notice: Subject to any disclaimer, the term of this patent is extended or adjusted under 35 U.S.C. 154(b) by 1142 days.

(21) Appl. No.: 10/484,560

(22) PCT Filed: Aug. 23, 2002

(86) PCT No.: PCT/US02/26881

§ 371 (c)(1),
(2), (4) Date: Dec. 18, 2006

(87) PCT Pub. No.: WO03/017939

PCT Pub. Date: Mar. 6, 2003

(65) Prior Publication Data
US 2008/0221123 A1 Sep. 11, 2008

Related U.S. Application Data

(60) Provisional application No. 60/314,795, filed on Aug. 24, 2001.

(51) Int. Cl.
*A61K 31/4965* (2006.01)
*C07D 241/04* (2006.01)
(52) U.S. Cl. .................. 514/255.02; 544/384
(58) Field of Classification Search ............ 514/255.02; 544/384
See application file for complete search history.

(56) References Cited

U.S. PATENT DOCUMENTS

| 4,251,438 | A | 2/1981 | Moon |
| 5,885,995 | A | 3/1999 | Dinsmore |
| 5,922,717 | A | 7/1999 | Pieper et al. |
| 6,358,956 | B1 | 3/2002 | Hartman et al. |

FOREIGN PATENT DOCUMENTS

| DE | 2519400 A1 | 3/1976 |
| DE | 2519400 A1 | 3/1976 |
| EP | 0457195 A3 | 11/1991 |
| WO | 98/27109 A1 | 6/1998 |
| WO | WO 98/27109 | 6/1998 |
| WO | 99/09985 A1 | 3/1999 |
| WO | WO 99/09985 | 3/1999 |
| WO | WO 99/37304 | 7/1999 |
| WO | WO 00/32590 | 6/2000 |
| WO | WO-00/32590 A1 | 6/2000 |
| WO | 01/07436 A2 | 2/2001 |
| WO | WO 01/07436 | 2/2001 |

OTHER PUBLICATIONS

Office Action issued by the European Patent Office on Mar. 27, 2007.
European Search Report, May 20, 2009.
Chow, M et al. "Structure and biological effects of lipid modification on proteins" Curr. Opin. Cell. Biol. 1992, 4:629-636.
Rowell, CA et al. "Direct demonstration of geranylgeranylation and farnesylation of Ki-Ras in vivo" J. Biol. Chem. 1997, 272:14093-14097.
Whyte, DB et al. "K- and N-Ras are geranylgeranylated in cells treated with farnesyl protein transferase inhibitors." J. Biol. Chem. 1997, 272:14459-14464.
Clark, EA et al. "Genomic Analysis of Metastasis Reveals an Essential Role for RhoC" Nature 2000, 406:532-535.
Zohn, IM et al., "Rho family proteins and Ras transformation: the RHOad less traveled gets gongestted" Oncogene 1998, 17:1415-1438.
Sebti, SM et al. "Farnesyltransferase and getanylgeranyltransferase-1 inhibitors and cancer therapy: lessons from mechanism and bench -to-bedside translational studies" Oncogene 2000, 19:6584-5493.
Aznar, S et al. "Rho signals to cell growth and apoptosis" Cancer Letters 2001, 165:1-10.
Whitehead, IP et al., "Rho GTPase dependent transformation by G-protein-coupled receptors" Oncogene 2001, 20:1547-1555.
Sun, J. et al. "Antitumor efficacy of a novel class of non-thiol-containing peptidomimetic inhibitors of farnesyltransferase and geranylgeranyltransferase1: Combination therapy with the cytotoxic agents cisplatin, taxol and gemcitabine." Cancer Res. 1999, 59:4919-4926.
Sun, J. et al., "Both farnesyltransferase and geranylgeranyltransferase 1 inhibitors are required for inhibition of oncogenic K-as prenylation but each alone is sufficient to suppress human tumor growth in nude mouse xenografts" Oncogene 1998, 16:1467-1473.
Sun, J., et al. "The geranylgeranyltransferase I inhibitor GGTI-298 induces hypophosphorylation of retinoblastoma and partner switching of cyclin-dependent kinase inhibitors- A potential mechanism for GGTI-298 antitumor activity." J. Biol. Chem. 1999, 274:6930-6934.
Macchia, M. et al., "Geranylgereanyl diphosphate-based inhibitors of post-translational geranylgeranylation of cellular proteins." J. Med. Chem. 1996, 39:1352-1356.
Zahn, TJ et al. "Synthesis and evaluation of GGPP geometric isomers: divergent substrate specificities of FTase and GGTase I" Bioorg. Med. Chem. Lett. 2001, 11:1605-1608.
Huber, HE et al. "Anions modulate the potency of geranylgeranyl-protein transferase I inhibitors." J. Biol. Chem. 2001, 27:24457-24465.

(Continued)

*Primary Examiner*—James O Wilson
*Assistant Examiner*—Ebenezer Sackey
(74) *Attorney, Agent, or Firm*—Dickstein Shapiro LLP

(57) ABSTRACT

The present invention relates to piperazinone compounds, pharmaceutical compositions containing those compounds and methods of treating tumors and cancer, among other disease states and conditions in mammalian patients, especially including humans.

15 Claims, 15 Drawing Sheets

OTHER PUBLICATIONS

Graham, SL et al. "Pseudopeptide inhibitors of Ras farnesyl-protein transferase" J. Med. Chem. 1994, 37:725-732.

Qian, YM et al. "Selective inhibition of type-I geranylgeranyltransferasae in vitro and in whole cells by CAAL peptidomimetics" Bioorg. Med. Chem. 1998, 6:293-299.

Vasudevan, A et al., "Potent, highly selective, and non-thiol inhibitors of protein geranylgeranyltransferase-I" J. Med. Chem. 1999, 42:1333-1340.

Berman, JM et al. "Aryloxy substituted N-arylpiperazinone as dual inhibitors of farnesyltransferase and geranylgeranyltransferasae-I" Bioorg. Med. Chem. Lett. 2001, 1411-1415.

DiMaio, J. et al. "Synthesis of chiral piperazine-2-ones asmmodel peptidomimetics" J. Chem. Soc. Perkin Trans. I 1989, 1687-1689.

Hunt, JT et al. "Potent, cell active, non-thiol tetrapeptide inhibitors of farnesyltransferase" J. Med. Chem. 1996, 39:353-358.

Sellier, C., Liebigs Ann. Chem. "Zur Synthese von (Z)- und (E)-3-(1H-Imidazol-4-ul)-2-propenamin und einigen 3-(1H-Imidazol-4-71)propanaminen." 1992, 317-324.

Matsui, T et al. Novel 5-HT3 antagonists-isoquinolinones and 3-aryl-2-pyridones: J. Med. Chem. 1992. 35:3307-3319.

Yamashita, T et al., "Synthesis and opiate activity of pseudo-tetrapeptides containing chiral piperazine-2-one and piperazine derivatives" Chem. Pharm. Bull. 1997, 45:1940-1944.

Hoffman, RW "Flexible molecules with defined shape-conformational design." Angew. Chem. Int. Ed. Engl. 1992, 31:1124-1134.

Vogt, A. et al. Protein geranylgeranylation, not farnesylation, is required for G1 to S phase transition in mouse fibroblasts.: Oncogene 199, 13:1991-1999.

Strickland, CL et al. "Crystal structure of farnesyl protein transferase complexed with a CaaX peptide and farnesyl diphosphate analogue." Biochemistry 1998, 37:16601.

Nowick, JS et al. "An improved method for the synthesis of enantiomerically pure amino acid ester isocyanates." J. Org. Chem. 1992, 57:7364-7366.

Sun, J. et al. "Both farnesyltransferase and geranylgeranyltransferase I inhibitors are required for inhibition of oncogenic K-Ras prenylation but each alone is sufficient to suppress human tumor growth in nude mouse xenografts." Oncogene 1998, 16:1467-1473.

Sun, J. et al. "Ras CAAS Peptidomimetic FTI-276 selectively blocks in nude mice the growth of a human lung carcinoma with a K-Ras mutation and a p53 deletion." Cancer Research 1995, 55:4243-4247.

Horwell, "The use of heterocycles for the conformational restriction of biologically active peptoids." Tetrahedron 54:4591-4606 (1998).

Scheme 1

Scheme 2

Scheme 3

Scheme 4

Scheme 5

Scheme 6

Scheme 7

Scheme 8

Table 1 GGTase-I and FTase inhibition data for piperazinone derivatives 26-33, and 13a1.

26 (GGTI-2364) R₁ = Me, R₂ = O
27 (GGTI-2365) R₁ = H, R₂ = O
28 (GGTI-2411) R₁ = Me, R₂ = S
29 (GGTI-2412) R₁ = H, R₂ = S 30 (GGTI-2376) R = Et
31 (GGTI-2377) R = H 32 (GGTI-2410)

13a1 (GGTI-2421) R = 
33 (GGTI-2422) R = H

| No. | Inhibitors | $IC_{50}$ (nM) | | FTase/ GGTase | $IC_{50}$ (μM) | |
|---|---|---|---|---|---|---|
| | | GGTase | FTase | | Rap1A | H-Ras |
| 26 | GGTI-2364 | >10,000 | >10,000 | | 20 | >30 |
| 27 | GGTI-2365 | 5,000 | >10,000 | >2 | >10 | >10 |
| 28 | GGTI-2411 | >10,000 | >10,000 | | >10 | >10 |
| 29 | GGTI-2412 | >10,000 | >10,000 | | >10 | >10 |
| 30 | GGTI-2376 | 18,000 | 8,600 | <0.5 | >10 | >10 |
| 31 | GGTI-2377 | 5,900 | 7,600 | >1 | >10 | >10 |
| 32 | GGTI-2410 | >10,000 | 9,300 | >1 | >10 | >10 |
| 13a1 | GGTI-2421 | 125 | >10,000 | >80 | >10 | >10 |
| 33 | GGTI-2422 | 9500 | >10,000 | >1 | >10 | >10 |

FIGURE 10

Table 2 GGTase-I and FTase inhibition data for piperazinone derivatives 34-53.

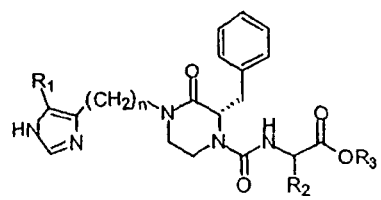

| No. | Inhibitor | n | R₁ | R₂ | R₃ | IC$_{50}$ (nM) GGTase | IC$_{50}$ (nM) FTase | FTase/GGTase | IC$_{50}$ (μM) Rap1A | IC$_{50}$ (μM) H-Ras |
|---|---|---|---|---|---|---|---|---|---|---|
| 34 | GGTI-2413 |   |   | (S-CH₂) | Me | 5300 | 1800 |   | ~10 | ~10 |
| 35 | GGTI-2414 | 1 | H | (S-CH₂) | H | 390 | 210 | 0.5 | >10 | >10 |
| 36 | GGTI-2415 |   |   | iPr | Me | 520 | >10,000 |   | 0.7 | >10 |
| 37 | GGTI-2416 | 1 | H | iPr | H | 79 | 3800 | 48 | >10 | >10 |
| 38 | GGTI-2395 |   |   | iPr | Me | 9900 | >10,000 |   | ~5 | >10 |
| 39 | GGTI-2396 | 3 | H | iPr | H | 16 | >10,000 | >625 | >10 | >10 |
| 40 | GGTI-2417 |   |   | iPr | Me | 1,000 | >10,000 |   | 0.3 | >10 |
| 41 | GGTI-2418 | 1 | Me | iPr | H | 9.5±2.6 | 58,000±6083 | 6105 | >10 | >10 |
| 42 | GGTI-2419 |   |   | (S-CH₂) | Me | 380 | >10,000 |   | ~10 | >10 |
| 43 | GGTI-2420 | 1 | Me | (S-CH₂) | H | 220 | 450 | 2 | >10 | >10 |
| 44 | GGTI-2399 |   |   | iBu | Me | >10,000 | >10,000 |   | >10 | >10 |
| 45 | GGTI-2400 | 1 | Me | iBu | H | >10,000 | >10,000 |   | >10 | >10 |
| 46 | GGTI-2401 |   |   | iPr | Me | >10,000 | >10,000 |   | >10 | >10 |
| 47 | GGTI-2402 | 1 | Me | iPr | H | 360 | 5600 | 15 | >10 | >10 |
| 48 | GGTI-2403 |   |   | Bn | Me | >10,000 | >10,000 |   | >10 | >10 |
| 49 | GGTI-2404 | 1 | Me | Bn | H | 5600 | >10,000 | >2 | >10 | >10 |
| 50 | GGTI-2405 | 1 | Me | CH₂-cyclohexyl | Me | 6900 | >10,000 |   | >10 | >10 |
| 51 | GGTI-2406 |   |   | CH₂-cyclohexyl | H | 240 | >10,000 | 42 | >10 | >10 |

| No. | Inhibitor | n | R₁ | R₂/R₃ group | GGTase | FTase | Rap1A | H-Ras |
|---|---|---|---|---|---|---|---|---|
| 52 | GGTI-2407 | 1 | Me | N-tBu | >10,000 | >10,000 | >10 | >10 |
| 53 | GGTI-2358 | 1 | Me | N-(p-tolyl) | >10,000 | >10,000 | >10 | >10 |

Table 3 GGTase-I and FTase inhibition data for piperazinone derivatives 54-60.

| No | Inhibitors | $R_1$ | $R_2$ | $R_3$ | IC$_{50}$ (nM) GGTase | IC$_{50}$ (nM) FTase | FTase/ GGTase | IC$_{50}$ (μM) Rap1A | IC$_{50}$ (μM) H-Ras |
|---|---|---|---|---|---|---|---|---|---|
| 40 | GGTI-2417 | benzyl | H | Me | 1,000 | >10,000 |  | 0.3 | >10 |
| 41 | GGTI-2418 | benzyl | H | H | 9.5±2.6 | 58,000± 6083 | 6105 | >10 | >10 |
| 54 | GGTI-2429 | naphthylmethyl | H | Me | 32 | >10,000 |  | 0.5 | >10 |
| 55 | GGTI-2430 | naphthylmethyl | H | H | 13.8±6.4 | 4838± 1050 | 350 | >10 | >10 |
| 56 | GGTI-2431 | 4-F-benzyl | H | Me | >10,000 | >10,000 |  | 0.7 | >10 |
| 57 | GGTI-2432 | 4-F-benzyl | H | H | 19.8±16.8 | 168,333± 42,525 | 8502 | >10 | >10 |
| 58 | GGTI-2433 | benzyl | H | Me | >10,000 | >10,000 |  | >10 | >10 |
| 59 | GGTI-2434 | benzyl | H | H | 780 | >10,000 | >13 | >10 | >10 |
| 60 | GGTI-2435 | benzyl | iPr | H | 7200 | >10,000 | >1 | >10 | >10 |

Figure 12A
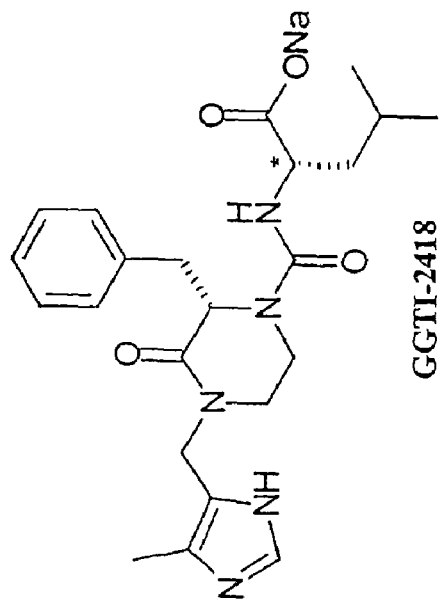
GGTI-2418
*in vitro* IC$_{50}$: GGTase I = 9.5nM; FTase =58,000nM
*in vivo* IC$_{50}$ : GGTase I = 0.3_M; FTase > 50_M
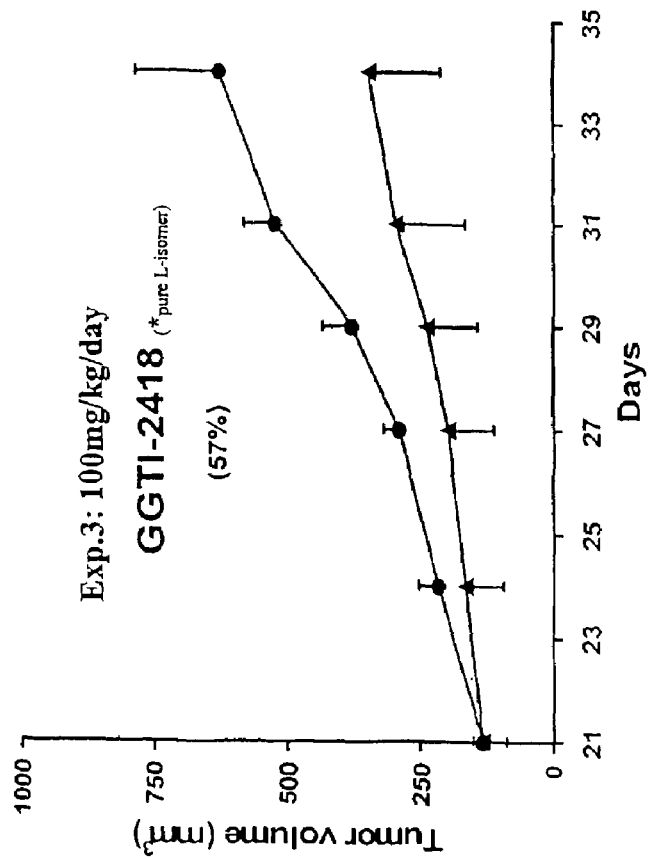

Figure 12B
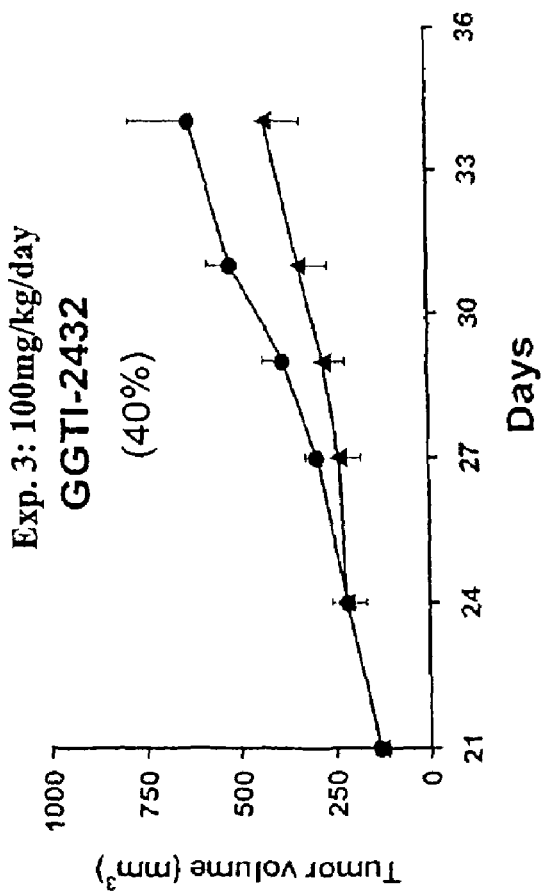
Exp. 3: 100mg/kg/day
GGTI-2432
(40%)
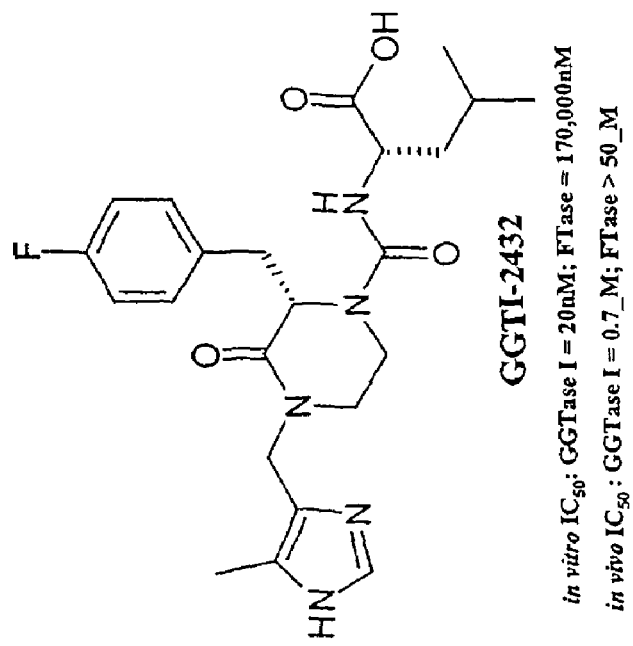
GGTI-2432
*in vitro* $IC_{50}$: GGTase I = 20nM; FTase = 170,000nM
*in vivo* $IC_{50}$ : GGTase I = 0.7 μM; FTase > 50 μM

Figure 12C
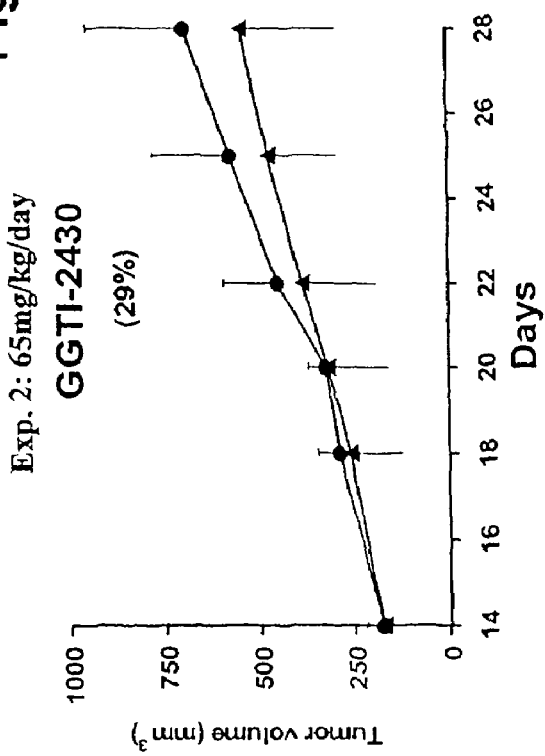
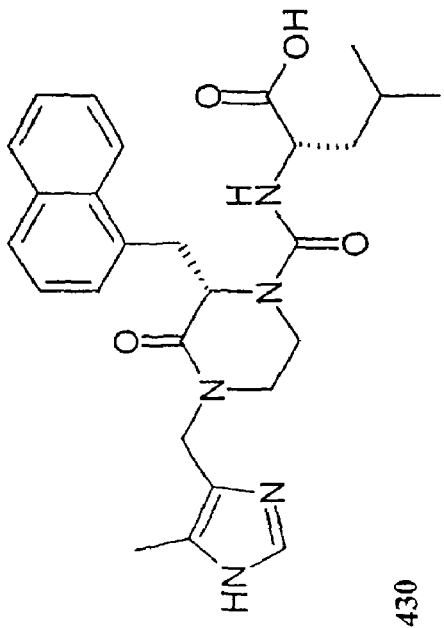
GGTI-2430
*in vitro* IC$_{50}$: GGTase I = 14nM; FTase = 4800nM
*in vivo* IC$_{50}$: GGTase I = 0.7_M; FTase = 50_M

Figure 12D
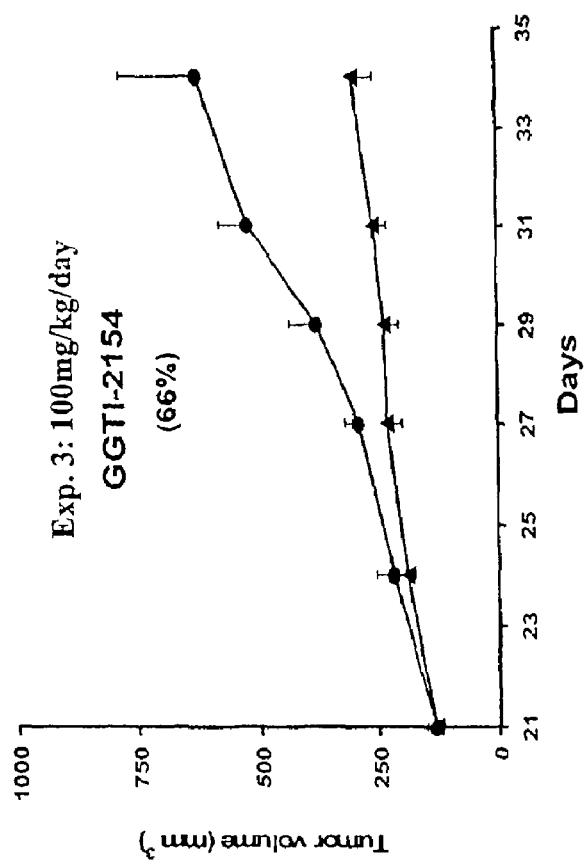
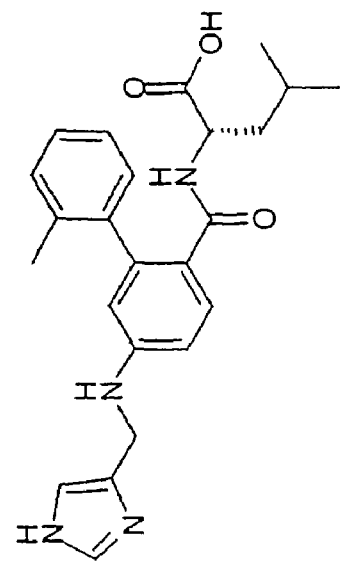
GGTI-2154
*in vitro* IC$_{50}$ : GGTase I = 20nM; FTase = 5600nM
*in vivo* IC$_{50}$ : GGTase I = 0.3_M; FTase > 10_M

PIPERAZINONE COMPOUNDS AS ANTI-TUMOR AND ANTI-CANCER AGENTS AND METHODS OF TREATMENT

RELATED APPLICATIONS

This application claims priority from U.S. provisional application Ser. No. 60/314,795, filed Aug. 24, 2001.

This invention was made with government support under CA067771 awarded by the National Cancer Institute. The government has certain rights in the invention.

FIELD OF THE INVENTION

The present invention relates to piperazinone compounds, pharmaceutical compositions containing those compounds and methods of treating tumors and cancer in mammalian patients, especially including humans.

BACKGROUND OF THE INVENTION

Cancer is a disease of abnormal cell growth often leading to death. Cancer is treated by three principal means; surgical removal of the tumor, therapeutic radiation, and treatment with anti-tumor chemical compounds. Treatment with chemical compounds, termed chemotherapy, is often hindered by the inherent toxicity of the chemicals to the patient and resistance of the tumor to the chemical treatment. Therefore the identification of less toxic anti-tumor agents capable of inhibiting growth of resistant tumors and/or treating cancer is of great importance. Alternative mechanism and targets for anti-tumor/anti-cancer therapy represent viable potential means of obtaining these goals.

Protein prenylation is an important lipid post-translational modification that affects about 0.5% of cellular proteins.[1] Prenylated proteins are covalently modified with either farnesyl or geranylgeranyl isoprenoid via thioether bonds to the C-terminal cysteine residues. Prenylated proteins mainly belong to the low molecular weight GTPase family, such as the Ras oncoproteins, and depend heavily on prenylation for their proper cellular localization and biological function.

Over the past decade, the major effort in designing prenyl-transferase inhibitors focused on protein farnesyltransferase (FTase), with the goal of specifically blocking malignant transformation caused by mutated Ras proteins. A particular emphasis was placed on developing highly selective FTase inhibitors (FTIs) to avoid potential toxicity. The approach has been very successful, even though, the antitumor activity of FTIs likely results from blocking farnesylation of one or more target-proteins other than Ras.[2,3] Some FTIs have demonstrated significant antitumor activity and lack of toxicity in animal models, and several compounds are currently in phase II clinical trials.

Recently, protein geranylgeranyltransferase I (GGTase-1) has gained increasing attention because many of its substrates, such as RhoC, RhoA, Rac-1, Cdc42, R-Ras, TC-21 were found to play critical roles in promoting tumorigenesis and/or metastasis.[4-8] In addition, K-Ras, the highly mutated and the most relevant target for Ras-targeted anticancer drug discovery, was found to be activated through geranylgeranylation when its farnesylation is inhibited by FTIs.[2-3] Further reasons for targeting GGTase-I in the development of novel anticancer agents arise from the desirable biological activities observed for GGTase inhibitors (GGTIs). These agents inhibited human tumor growth in vitro and in vivo with a mechanism that is consistent with a cell cycle arrest at the G1 phase.[9-11] This includes induction of the CDK inhibitor p21$^{waf}$, inhibition of CDK2 and CDK4 kinase activities and induction of hypophosphorylation of pR.[9-11] No significant toxicity was observed in animal studies at the doses tested.

The complex networks of signal transduction pathways involving key GGTases have not been fully characterized. Therefore, developing highly selective GGTIs, would provide valuable tools to study the related proteins in normal and cancer cell growth. Specific GGTase-I inhibitors, in combination with other anti-cancer therapy, may have significant potential as cancer chemotherapeutic agents for the treatment of malignant tumors advanced to the metastatic stage.

OBJECTS OF THE INVENTION

In one aspect of the invention, an object of the present invention is to provide compounds and methods for the treatment of tumors and/or cancer in mammals, especially humans.

It is another object of the invention to provide pharmaceutical compositions for use in the treatment of tumors and/or cancer.

It is still another object of the invention to provide inhibitors of GTTase enzymes, in particular GTTase I enzyme and methods of inhibition such enzymes in patients.

In other aspects of the invention, objects of the present invention provide compounds, pharmaceutical compositions and methods for the treatment of neoplasia, hyperproliferative cell growth, psoriasis, intimal hyperplasia (restinosis) and chronic inflammatory diseases including rheumatoid and osteoarthritis.

One or more of these and/or other objects of the present invention may be readily gleaned from a review of the description of the present invention which follows.

<sup>a</sup>Reagents and conditions: (a) 1,2-dibromoethane, K$_2$CO$_3$, NaOH, H$_2$O, 95° C., 5 h, 75%; (b) H$_2$SO$_4$, EtOH, reflux, 85%; (c) N-1-trityl-deaminohistidine, EDCI, DIEA, CH$_2$Cl$_2$, 90%; (d) 40% TFA/CH$_2$Cl$_2$, triethylsilane, 90%; (e) NaOH/H$_2$O, MeOH, 90%.

Figure 6:
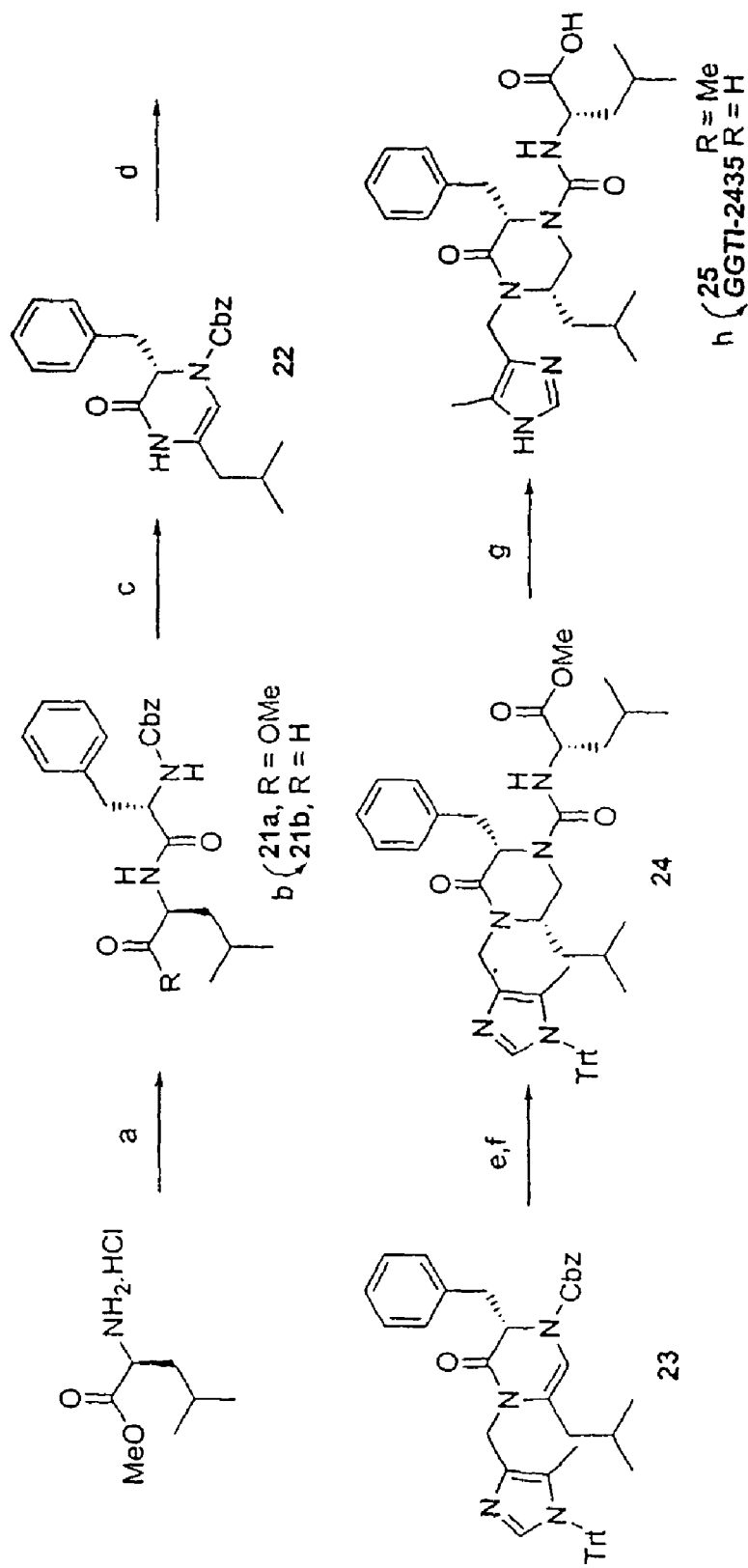

FIG. 6 shows the chemical synthesis of GGTI-2435 according to the present invention. <sup>a</sup>Reagents and conditions: (a) N-Cbz-L-Phe, EDCI, DIEA, CH$_2$Cl$_2$, 90%; (b) DIBAL/CH$_2$Cl$_2$, 40%; (c) 70% TFA/H$_2$O, 87%; (d) NaH, 9, THF, 60° C., 2 h; 15% (e) H$_2$, 10% Pd/C, EtOAc/MeOH, 98%; (f) 5a, CH$_2$Cl$_2$, 0° C.-rt, 4 h, 88%; (g) 40% TFA/CH$_2$Cl$_2$, triethylsilane; 90%; (h)1N NaOH/H$_2$O, MeOH, 90%.

Figure 7:
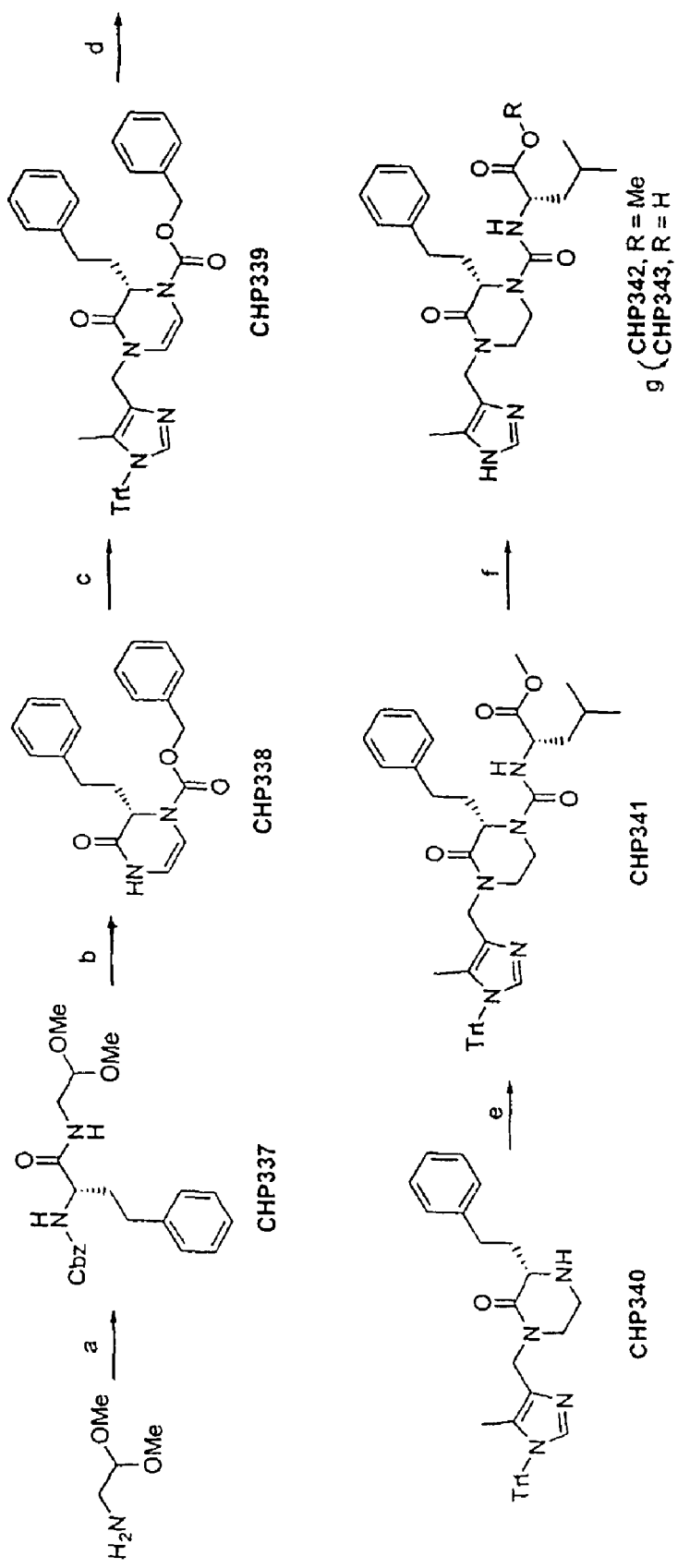

FIG. 7 shows the chemical synthesis of analogs CHP342 and CHP343 according to the present invention. <sup>a</sup>Reagents and conditions: (a) N-Cbz-homophenylalanine, EDCI, DIEA, CH$_2$Cl$_2$, 90%; (b) 70% TFA/H$_2$O, 95%; (c) NaH, 4-chloromethyl-5-methyl-1-trityl-imidazole, THF, 60° C., 2 h, 18%; (d) H$_2$, 10% Pd/C, MeOH, 100%; (e) L-leucine methyl ester isocyanate, CH$_2$Cl$_2$, 0° C.-rt, 4 hr, 84%; (f) 40% TFA/CH$_2$Cl$_2$, triethylsilane, 85%; (g) 1N NaOH/H$_2$O; MeOH, 88%.

Figure 8:
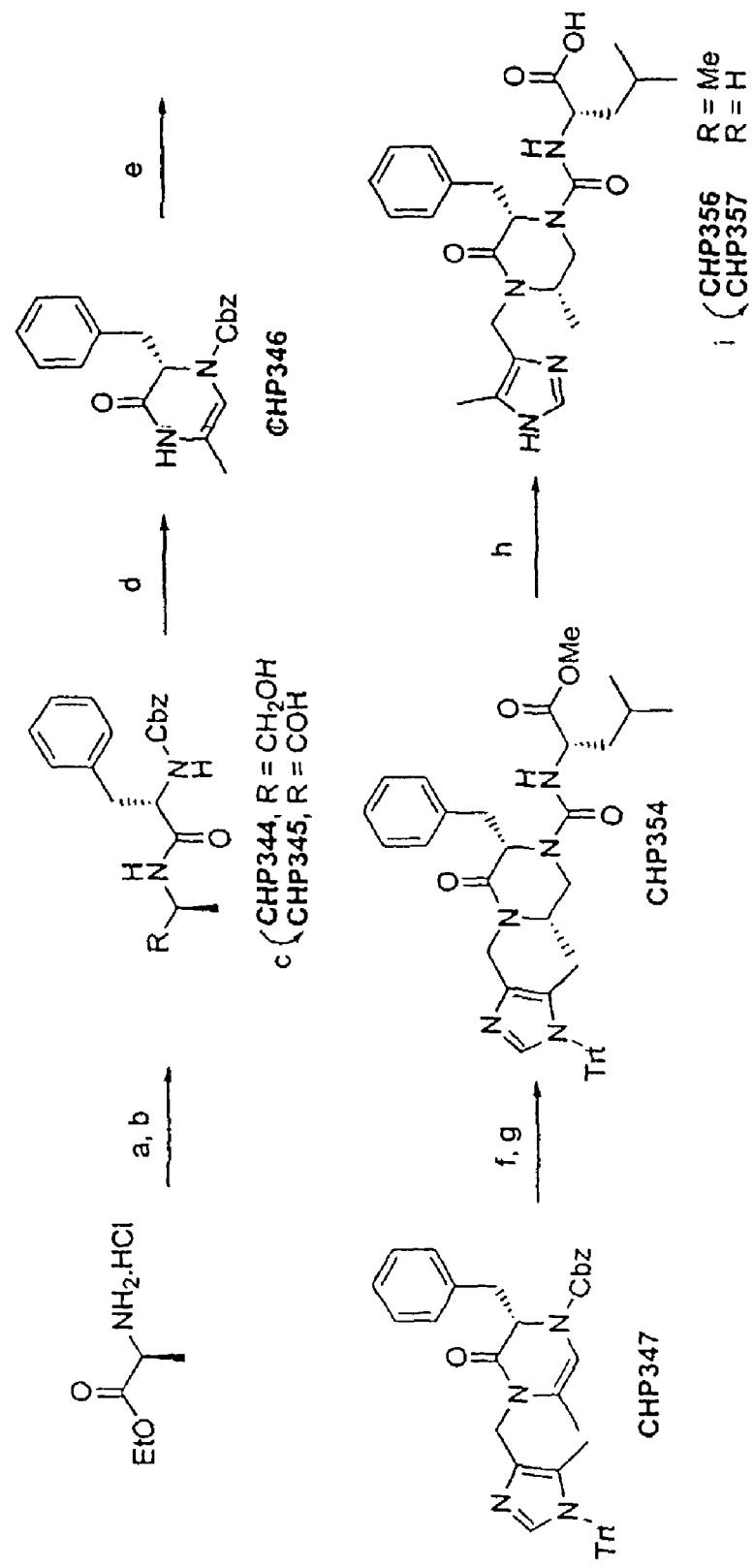

FIG. 8 shows the synthesis of CHP 356 and CHP 357, compounds according to the present invention. <sup>a</sup>Reagents and conditions: (a) N-Cbz-LPhe, EDCI, DIEA, CH$_2$Cl$_2$ 88%; (b) DIBAL/CH$_2$Cl$_2$, rt, 2 h, 83%; (c) Swern oxidation, 80%; (d) 70% TFA/H$_2$O, 95%; (e) NaH, 4-chloromethyl-5-methyl-1-trityl-imidazole, THF, 60° C., 2 h, 10%; (f) H$_2$, 10% Pd/C, MeOH, 90%; (g) L-leucine methyl ester isocyanate, CH$_2$Cl$_2$, 0° C.-rt, 4 hr, 79%; (h) 40% TFA/CH$_2$Cl$_2$, triethylsilane, 85%; (i) 1N NaOH/H$_2$O; MeOH, 85%.

Figure 9:
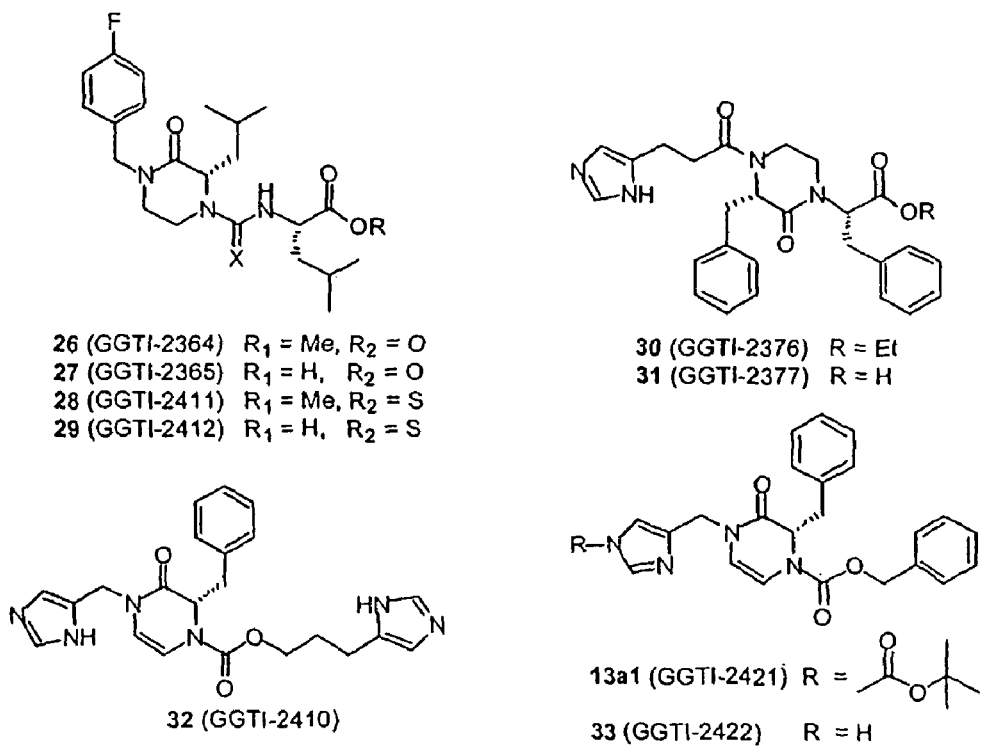
Figure 11:
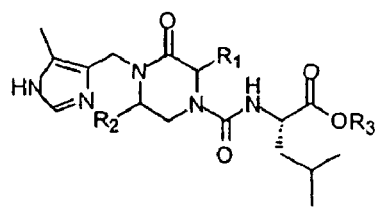

FIGS. 9-11 show the results of in vitro inhibition studies on GGTase using compounds according to the present invention.

FIGS. 12a-d show the results of in vivo inhibition activity of the indicated compounds against tumor growth. In the experiment described, A-549 cells were implanted s.c. in nude mice and when the tumors reached an average size of about 50 to 100 mm$^3$, the animals were randomized and treated either with vehicle or the indicated compounds. FIGS. 12A-D show that, over a period of 28-34 days, tumors from animals that were treated with vehicle reached an average size of about 600 mm$^3$ whereas those treated with GGTI-2418 (FIG. 12A), GGTI-2132 (FIG. 12B), GGTI-2430 (FIG. 12C) and GGTI-2154 (FIG. 12D) grew to average sizes of 280, 300, 500 and 250 mm$^3$, respectively.

SUMMARY OF THE INVENTION

The present invention relates to compounds according to the structure:

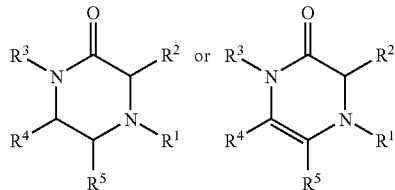

where $R^1$ and $R^3$ are each independently a $C_5$-$C_{15}$ is alkyl or alkenyl group, an aryl, heterocycle, alkylenearyl, alkenylenearyl, alkyleneheterocycle or alkenylene heterocycle group, preferably an alkylenephenyl group, most preferably a benzyl group, wherein said alkylene, alkenylene, aryl or heterocycle group may be unsubstituted or substituted, wherein said alkylene or alkenylene group preferably ably contains up to 8 carbon atoms, even more preferably no more than 4 carbon atoms, a $C_2$-$C_{10}$ ether or thioether group, a COR (keto containing group) CO$_2$R (carboxylic acid or ester group), COSR (thioester group), a (CH$_2$)$_n$COR, (CH$_2$)$_n$CO$_2$R or (CH$_2$)$_n$COSR group, where n is 1 to 8, preferably 1 to 4, R is H, a $C_1$-$C_{10}$ alkyl or alkenyl group, an unsubstituted or substituted aryl (preferably, a phenyl) or heterocycle group, an alkylenearyl, alkenylene aryl, alkyleneheterocycle or alkenyleneheterocycle group, wherein said alkylene, alkenylene, aryl or heterocycle group is unsubstituted or substituted, a thioether group containing from 2 to 8 carbon atoms, a

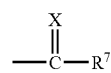

group, where X is O or S, preferably O,
where $R^7$ is a $C_1$-$C_{10}$ alkyl, alkenyl, ether or thioether group, an aryl or heterocycle group, an alkylenearyl, alkenylenearyl, alkyleneheterocycle or alkenylene heterocycle group, which may be unsubstituted or substituted, wherein said alkylene or alkenylene group preferably contains up to 8 carbon atoms, preferably no more than 4 carbon atoms, an amine or alkyleneamine group which may be substituted or unsubstituted on the alkylene group or unsubstituted (free amine) or mono or disubstituted on the amine with a $C_1$-$C_4$ alkyl or alkanol group, an amino acid or amino ester residue wherein the amine of said amino acid or amino ester residue is
chemically bonded to the carbon of the

group, or a

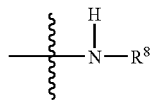

group
wherein $R^8$ is independently H, a $C_1$-$C_{10}$ alkyl or alkenyl group, an aryl, heterocycle, alkylene aryl or alkyleneheterocycle group, which may be unsubstituted or substituted or an alkylene ester group

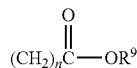

where n is 1-4 and said alkylene group of said alkylene ester may be substituted by a group $R^{10}$, where $R^9$ is a $C_1$-$C_6$ alkyl group and $R^{10}$ is a $C_1$-$C_8$ alkyl, alkenyl, ether or thioether group, an aryl, heterocycle, alkylenearyl, alkenylenearyl, alkyleneheterocycle or alkenylene heterocycle group, wherein said alkylene, alkenylene, aryl or heterocycle may be unsubstituted or substituted, wherein said alkylene or said alkenylene group preferably contains no more than 8 carbon atoms with the proviso that $R^3$, but not $R^1$, may further represent an amino acid or amino ester residue wherein the amine group of said amino acid or amino ester forms the amine in the position alpha to the ketone in the pyrazinone ring;

$R^2$, $R^4$ and $R^5$ are each independently H, a $C_1$-$C_{15}$ is (preferably, $C_5$-$C_{15}$) alkyl or alkenyl group, $CF_3$, F, Cl, Br, I, CN, $NO_2$, $NH_2$, $NHR_1$, $NR_1R_1$, COR (acyl group), $OR_1$ (hydroxyl or ether group), an aryl, heterocycle, alkylenearyl, alkenylenearyl, alkyleneheterocycle or alkenylene heterocycle group, preferably an alkylenephenyl group, most preferably a benzyl group, wherein said alkylene, alkenylene, aryl or heterocycle group may be unsubstituted or substituted, wherein said alkylene or alkenylene group preferably contains up to 8 carbon atoms, even more preferably no more than 4 carbon atoms, a $C_2$-$C_{10}$ ether or thioether group, a $CO_2R_1$, (carboxylic acid or ester group), or $COSR_1$, (thioester group) where $R_1$ is H, a $C_1$-$C_{10}$ alkyl or alkenyl group, an unsubstituted or substituted aryl (preferably, a phenyl) or heterocycle group, an alkylenearyl, alkenylene aryl, alkyleneheterocycle or alkenylene heterocycle group, wherein said alkylene, alkenylene, aryl or heterocycle group is unsubstituted or substituted, a thioether group containing from 2 to 8 carbon atoms, or a

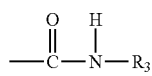

group, where $R_3$ is H, a $C_1$-$C_{10}$ (preferably a $C_1$-$C_4$) alkyl, alkenyl, ether or a thioether group, with the proviso that at least one, and preferably two of $R^2$, $R^4$ and $R^5$ is H (more preferably $R^5$ is H); including all isomeric mixtures, isolated stereoisomers, geometric isomers and optical isomers thereof, or a pharmaceutically acceptable salt thereof.

In preferred aspects of the present invention, $R^4$ and $R^5$ are H, $R^1$ and/or $R^3$ is an ester $CO_2R$, an alkylene aryl group, more preferably a benzyl group or a group

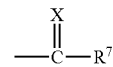

and $R^2$ is an alkylene aryl group, preferably an unsubstituted benzyl group.

Preferably, R is an alkylenearyl group or alkyleneheterocycle group, X is preferably O and $R^7$ is an amino acid residue, more preferably, a natural amino acid most preferably a leucine residue, or a

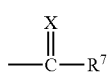

group, where $R^8$ is an alkylene ester where the alkylene group is a methylene group substituted with a thioether, alkyl, phenyl, benzyl, methylenecyclohexyl or methylene naphthalene group. More preferably, $R^1$ is a

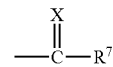

group where X is O and $R^7$ is an amino acid group bonded to the carbonyl at the amino group of the amino acid thus forming a urea moiety and $R^3$ is an alkylene aryl or alkylene heterocycle, preferably a methylene imidazole group which is alkyl, more preferably, methyl substituted or an unsubstituted benzyl group.

In preferred compound aspects of the present invention, $R^2$ is disposed in a configuration which is alpha (i.e., below the horizontal plane of the piperazinone moiety) to the piperazinone core moiety. Compounds according to the present invention preferably are represented by the chemical structures:

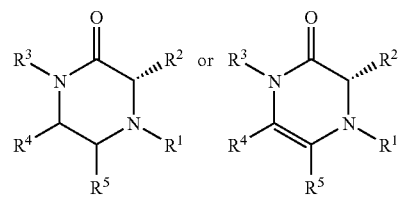

where the substituents $R^1$, $R^2$, $R^3$, $R^4$ and $R^5$ are described above. Preferably, $R^5$ is H and more preferably, both the $R^4$ and $R^5$ substituents are H. It is to be understood that $R^2$, $R^4$ and $R^5$ substituents may be disposed on the alpha (down) or beta (up) face of the pyrazinone moiety.

Compounds according to the present invention are preferably derived from amino acids such that one or more of $R^1$, $R^2$ or $R^3$ substituents is an amino acid residue or is derived from an amino acid residue.

Preferred embodiments according to the present invention relate to a compound according to the structure:

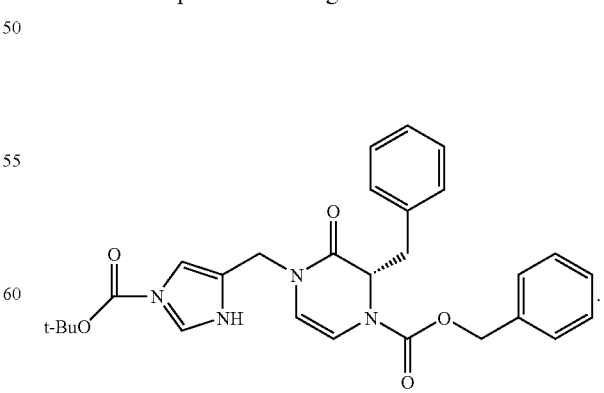

Other preferred embodiments according to the present invention relate to a compound according to the structure:

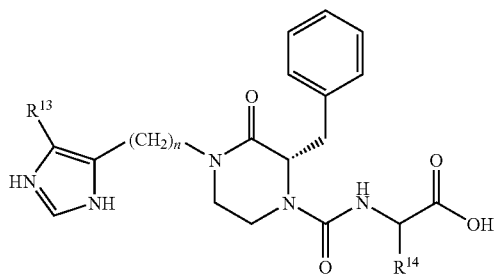

where n is 1-3;
R¹³ is H or CH₃; and
R¹⁴ is a group according to the structure:

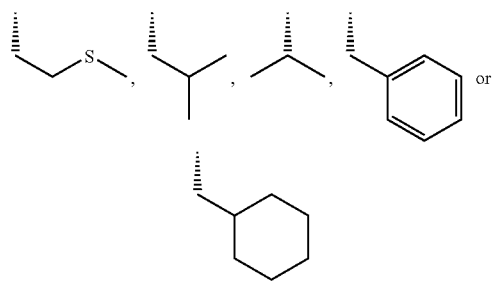

or

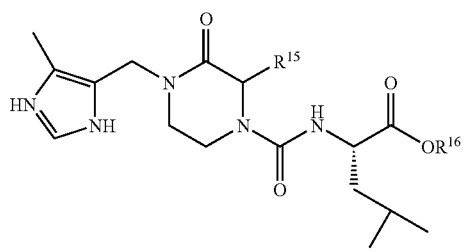

Still other preferred embodiments according to the present invention relate to compounds according to the structure:

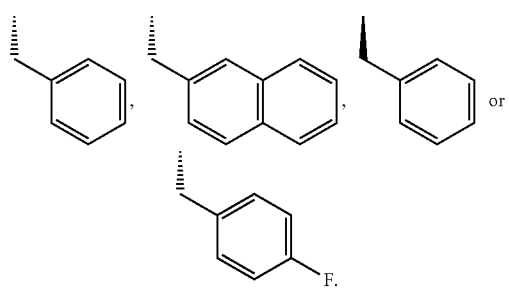

where $R^{16}$ is H or CH₃; and $R^{15}$ is

It is noted that the present invention contemplates all geometric and optical isomers of compounds according to the present invention, as mixtures or as separated isomers exhibiting high purity (i.e. preferably at least about 90% purity, even more preferably at least about 95% purity and even more preferably at least about 99% purity and in some cases as high as 100% purity).

The present invention also relates to pharmaceutical compositions comprising effective amounts of one or more compounds according to the present invention optionally in combination with a pharmaceutically acceptable additive, carrier or excipient.

In a method aspect, the present invention is directed to the inhibition of GGTase enzyme, in particular GGTaseI in patients comprising administering to said patient an effective amount of one or more compounds according to the present invention to the patient. The method of inhibiting GGTase, especially GGTaseI in a patient will result in a pharmacological effect consistent with such inhibition in the patient.

The present invention is also directed to a method for treating tumors and/or cancer in a patient in need of therapy comprising administering to such a patient an effective amount of one or more compounds according to the present invention, optionally in combination with a pharmaceutically acceptable additive, carrier or excipient.

The tumors and/or cancer to be treated with compounds of the present invention include benign and malignant neoplasia, including various cancers such as, stomach, colon, rectal, liver, pancreatic, lung, breast, cervix uteri, corpus uteri, ovary, prostate, testis, bladder, renal, brain/cns, head and neck, throat, Hodgkins disease, non-Hodgkins leukemia, multiple myeloma leukemias, skin melanoma, acute lymphocytic leukemia, acute mylogenous leukemia, Ewings Sarcoma, small cell lung cancer, choriocarcinoma, rhabdomyosarcoma, Wilms Tumor, neuroblastoma, hairy cell leukemia, mouth/pharynx, oesophagus, larynx, melanoma, kidney, lymphoma, among others. Compounds according to the present invention are particularly useful in the treatment of a number of cancers, including those which are drug resistant, including multiple drug resistant.

A method of treating hyperproliferative cell growth and psoriasis and related conditions using one or more of the disclosed compositions are other inventive aspects of the present invention. This method comprises administering to a patient in need of therapy an effective amount of one or more compounds according to the present invention to said patient, optionally in combination with an additive, carrier or excipient.

A method of treating arthritis and chronic inflammatory diseases, including rheumatoid arthritis and osteoarthritis, among others represent other inventive aspects of the present invention. This method comprises administering to a patient in need of therapy an effective amount of one or more compounds according to the present invention to said patient, optionally in combination with an additive, carrier or excipient.

DETAILED DESCRIPTION OF THE INVENTION

The following terms shall be used throughout the specification to describe the present invention.

The term "patient" is used throughout the specification to describe a subject animal, preferably a human, to whom treatment, including prophylactic treatment, with the compounds/compositions according to the present invention is provided. For treatment of those conditions or disease states which are specific for a specific animal such as a human patient, the term patient refers to that specific animal.

The term "neoplasia" is used to describe the pathological process that results in the formation and growth of a neoplasm, i.e., an abnormal tissue that grows by cellular proliferation more rapidly than normal tissue and continues to grow after the stimuli that initiated the new growth cease. Neoplasia exhibits partial or complete lack of structural organization and functional coordination with the normal tissue, and usually form a distinct mass of tissue which may be benign (benign tumor) or malignant (carcinoma). The term "cancer" is used as a general term to describe any of various types of malignant neoplasms, most of which invade surrounding tissues, may metastasize to several sites and are likely to recur after attempted removal and to cause death of the patient unless adequately treated. As used herein, the term cancer is subsumed under the term neoplasia. The term "tumor and/or cancer" is used to describe all types of neoplasia, including benign and malignant. The other conditions and/or disease states which are described herein use standard terms for their description which are well known in the art. Exemplary tumors and/or cancers which may be effectively treated by the present invention include, for example, stomach, colon, rectal, liver, pancreatic, lung, breast, cervix uteri, corpus uteri, ovary, prostate, testis, bladder, renal, brain/cns, head and neck, throat, Hodgkins disease, non-Hodgkins leukemia, multiple myeloma leukemias, skin melanoma, acute lymphocytic leukemia, acute mylogenous leukemia, Ewings Sarcoma, small cell lung cancer, choriocarcinoma, rhabdomyosarcoma, Wilms Tumor, neuroblastoma, hairy cell leukemia, mouth/pharynx, oesophagus, larynx, melanoma, kidney, lymphoma, among others.

The term "pharmaceutically acceptable salt" is used throughout the specification to describe a salt form of analogs of one or more of the compounds described herein which are presented to increase the solubility of the compound in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Additional salts include acid addition salts of amines such as, for example, HCl salts, carboxylic acid salts (malate, citrate, taurate, oxalate, etc.) and phosphate salts, among numerous others. Salt formulation is a function of the chemical formula of a given compound, as one of ordinary skill will readily understand.

The term "pharmaceutically acceptable derivative" is used throughout the specification to describe any pharmaceutically acceptable prodrug form (such as an ester or ether or other prodrug group) which, upon administration to a patient, provides directly or indirectly the present compound or an active metabolite of the present compound.

The term "alkyl" shall mean within its context a fully saturated $C_1$-$C_{10}$ hydrocarbon linear, branch-chained or cyclic radical, preferably a $C_1$-$C_4$, even more preferably a $C_1$-$C_3$ linear, branch-chained or cyclic fully saturated hydrocarbon radical. The term "alkenyl" is used to describe a hydrocarbon group, similar to an alkyl group which contains one double bond. The terms "alkylene" and "alkenylene" are used to describe alkyl and alkenyl divalent radicals.

The term "aryl" shall mean within its context a substituted or unsubstituted monovalent carbocyclic aromatic radical having a single ring (e.g., phenyl) or multiple condensed rings (e.g., naphthyl, anthracene, phenanthrene). Other examples include heterocyclic aromatic ring groups (heteroaryl) having one or more nitrogen, oxygen, or sulfur atoms in the ring, such as imidazolyl, furyl, pyrrolyl, pyridyl, thiazole, piperazinyl and indolyl, among numerous others. The preferred aryl group in compounds according to the present invention is a phenyl or substituted phenyl group (preferably substituted with at least one halogen).

The term "ether" or "thioether" shall mean an ether or thioether group, formed from an oxygen or sulfur and an alkyl/alkylene group at a position on phenyl moiety of compounds according to the present invention, or alternatively, may also contain at least one oxygen or sulfur within the alkyl chain or alkylene chain.

The term "heterocycle" shall mean a moiety which is cyclic and contains at least one atom other than a carbon atom, such as a nitrogen, sulfur, oxygen or other atom. Preferably, a heterocycle according to the present invention is a piperazine (including piperazinone), furan, pyrrole, imidazole, thiazole, oxazole or isoxazole group, which may be substituted or unsubstituted, preferably substituted with a $C_1$-$C_3$ alkyl group or a phenyl group which may be bonded at one or two carbon atoms of the heterocycle with the phenyl group (where the phenyl group is bonded to two positions on the heterocycle it forms a two membered ring structure with the phenyl group), the phenyl group being substituted or unsubstituted, preferably unsubstituted.

The term "unsubstituted" shall mean substituted with hydrogen atoms. The term "substituted" shall mean, within the chemical context of the compound defined, a substituent selected from an alkyl (generally, no greater than about 12 carbon units in length), aryl (which also may be heteroaryl), heterocycle, alkylenearyl, alkyleneheterocycle, $CF_3$, halogen, CN, nitro, amine or alkyleneamine (including monoalkyl and dialkyl amines) acyl, ester, alkyleneacyl (keto), alkylene ester, carboxylic acid, alkylene carboxylic acid, thioester, ether, thioether, amide, substituted amide or alkyleneamide, wherein the alkylene group is from 1 to 8 carbon units long and the alkyl group on an ester is from 1 to 8 carbon units long, preferably up to 4 carbon units long.

The term "amino acid" shall mean a compound which contains an amino group and a carboxylic acid. Amino acids are described as amino acids, β amino acids and γ amino acids, depending on the position of substitution of the amino group relative to the carboxylic acid group in the molecule. Preferred amino acids for use in the present invention include the naturally occurring α-L amino acids. These include alanine, valine, leucine, isoleucine, proline, phenylalanine, tryptophan, methionine, glycine, serine, threonine, cysteine, tyrosine, asparagine, glutamine, aspartic acid, glutamic acid, lysine, arginine and histidine, with valine, leucine, isoleucine, threonine, phenylalanine and methionine being preferred. α-D amino acids and other amino acids may also be used, but are generally less preferred. The term "amino acid residue" is used to describe a substituent on a pyrazinone compound according to the present invention which is derived from an amino acid by virtue of reaction of an amino acid with a molecule to incorporate the amino acid into the molecule. The term "amino ester" refers to an amino acid or amino acid residue wherein the carboxylic acid is in the form of a $C_1$-$C_8$, preferably a $C_1$-$C_4$ ester, rather than an acid.

The terms "alpha" and "beta", or their corresponding Greek letters α and β, used to represent alpha and beta, refer, within the context of their use, to the position of a moiety which is disposed below (alpha) or above (beta) a plane of reference of a molecule (generally, the piperazinone ring or moiety of the present compounds), or alternatively, to the bonding of a moiety at a carbon or other atom at a position next to an atom of reference (alpha) or at an atom in a position next to the alpha position.

The term "geometric isomer" shall be used to signify an isomer of a compound according to the present invention wherein a chemical group or atom occupies different spatial positions in relation to double bonds or in saturated ring systems having at least three members in the ring as well as in certain coordination compounds. Thus "cis" and "trans" isomers are geometric isomers as well as isomers of for example, cyclohexane and other cyclic systems. In the present invention all geometric isomers as mixtures (impure) or pure isomers are contemplated by the present invention. In preferred aspects, the present invention is directed to pure geometric isomers.

The term "optical isomer" is used to describe either of two kinds of optically active 3-dimensional isomers (stereoisomers). One kind is represented by mirror-image structures called enantiomers, which result from the presence of one or more asymmetric carbon atoms. The other kind is exemplified by diastereomers, which are not mirror images and which contain at least two asymmetric carbon atoms. Thus, such compounds have $2_n$ optical isomers, where n is the number of asymmetric carbon atoms. In the present invention all optical isomers in impure (i.e., as mixtures) or pure or substantially pure form (such as enantiomerically enriched or as separated diastereomers) are contemplated by the present invention.

The term "inhibitory effective concentration" or "inhibitory effective amount" is used throughout the specification to describe concentrations or amounts of compounds according to the present invention which substantially or significantly inhibit the growth of a tumor or cancer within the context of administration to a patient.

The term "therapeutic effective amount" or "therapeutically effective amount" is used throughout the specification to describe concentrations or amounts of compounds according to the present invention which are therapeutically effective in treating tumors/cancer or the various conditions or disease states including hyperproliferative cell growth, psoriasis and related conditions, as well as arthritis and chronic inflammatory diseases, including rheumatoid arthritis and osteoarthritis, among others.

The term "preventing effective amount" is used throughout the specification to describe concentrations or amounts of compounds according to the present invention which are prophylactically effective in preventing, reducing the likelihood of contracting or delaying the onset of one or more of the disease states according to the present invention. Within the context of the present invention, a preventing effective amount is that amount, for example, which may reduce the likelihood that a precancerous lesion may become a malignant tumor or that a non-malignant tumor will become malignant. This term is subsumed under the term "effective amount". Certain compounds according to the present invention are particularly useful as prophylactic agents because of the reduced toxicity these compounds exhibit to non-tumorigenic and/or non-cancerous cells.

The term "effective amount" shall mean an amount or concentration of a compound or composition according to the present invention which is effective within the context of its administration, which may be inhibitory, prophylactic and/or therapeutic. Compounds according to the present invention are particularly useful for providing favorable change in the disease or condition treated, whether that change is a remission, a decrease in growth or size of cancer or a tumor or other effect of the condition or disease to be treated, a favorable physiological result or a reduction in symptomology associated with the disease or condition treated.

Compounds according to the present invention may be synthesized by methods known in the art, or alternatively, by the preferred efficient synthetic methods presented in the present specification, either by following the specific syntheses or by analogy using well-known synthetic methods known. Compounds not specifically presented in the examples section of the present specification may be readily synthesized by analogy with those schemes specifically presented, or alternatively, by modifications using well-known synthetic steps.

In general, the compounds according to the present invention are synthesized by forming a piperazinone ring with substituents already present in the precursors or intermediates such that once the piperazinone moiety is formed, substituents may be added to the formed piperazinone moiety in order to produce the final compounds. Introduction of a substituent at a carbon position on the piperazinone ring alpha to the carbonyl group is preferably introduced into an intermediate or precursor molecule before formation of the heterocylic piperazinone ring. After formation of the piperazinone ring, other substituents may be added, for example, especially those on one or both of the amine groups in the piperazinone ring. Preferably, at least one of the two amine groups in the piperazinone ring is introduced in precursors prior to its formation is substituted; in certain instances both may be substituted. Preferably, the $R^3$ substituent of the present compounds (on the amine alpha to the ketone of the piperazinone moiety) is introduced prior to formation of the piperazinone moiety and the $R^1$ substituent is added after ring formation, although $R^1$ may be added prior to formation of the ring and $R^3$ may be added after formation of the ring. In preferred aspects of the present invention $R^3$ is a methylene imidazole group which is alkyl, preferably methyl substituted, or a benzyl group.

One or more of the carbon positions in the piperazinone precursors is favorably substituted, which upon formation of the piperazinone group, provides a substituent at any one of $R^2$, $R^4$ or $R^5$ of the piperazinone moiety. While substituents in the carbon positions of the piperazinone moiety may be added after formation of the piperazinone moiety, it is preferred that the carbon substituents be introduced into the precursors before formation of the piperazinone moiety for ease of synthesis.

It is generally easier to introduce the substituent $R^1$ onto the amine which is in the position beta to the carbonyl of the piperazinone moiety rather than to the amine in the alpha position, because the amine in the beta position is more nucleophilic than is the amine in the alpha position. Thus, in certain chemical syntheses, introduction of a substituent $R^1$ onto the beta amine occurs after formation of the piperazinone moiety.

Preferred compounds according to the present invention include a $R^1$ substituent which contains a urea or thiourea moiety which has been prepared by formation of an isocyanate or thioisocyanate at the amine in the position beta to the carbonyl group and then reacting the isocyanate or thioisocyanate with an amino acid to form a urea or thiourea. These are preferred compounds according to the present invention.

Other compounds which fall within the general description of the present invention may be synthesized by routine modification of the above-describe synthesis and as otherwise taught in this specification.

By way of specific description, a number of compounds embraced by the present invention were synthesized. The piperazin-2-one derivatives described in this paper were synthesized as represented in Schemes 1-6. In Scheme 1, substitution on the N-1 position of the piperazinone ring was introduced by reductive amination of aminoacetaldehyde dimethyl acetal with p-fluorobenzaldehyde in the presence of NaBH(OAc)$_3$. Coupling of the resulting secondary amine 1 with N-Cbz-L-leucine using EDCI afforded compound 2, which cyclized in 70% TFA/H$_2$O[19] with good yield to produce the piperazin-2-one scaffold as a Cbz-protected enamine 3. The crystal structure of 3 obtained at −90° C. showed a single conformation corresponding to the Z-isomer about the Cbz-carbamate group. However, the NMR spectrum of 3 in methanol clearly showed two sets of signals representing the two distinct Z- and E-conformers.[20] Deprotection and saturation of the double bond were accomplished in one step by hydrogenation using 10% Pd/C catalyst to give the piperazin-2-one scaffold 4. Reaction of L-leucine methyl ester with phosgene or thiophosgene gave the corresponding isocyanate 5a or isothiocyanate 5b, which could then be coupled with 4 to give GGTI-2364 and GGTI-2411, respectively. The methyl esters were hydrolyzed under basic condition to give acids GGTI-2365 and GGTI-2412.

Figure 2:
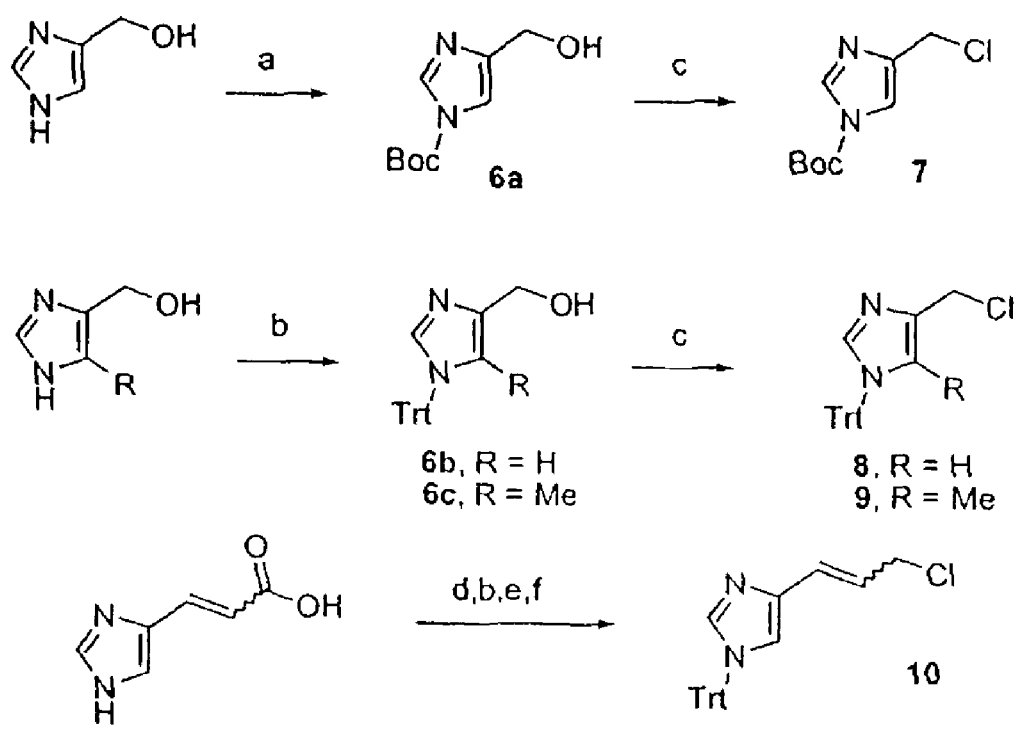
FIG. 2 shows the chemical synthesis of a trityl-protected vinyl chloride substituted imidazole intermediate used to make compounds according to the present invention. $^a$Reagents and conditions: (a) (Boc)$_2$O, DMF, overnight, 80%; (b) TrtCl, Et$_3$N, DMF, overnight; 85-95%; (c) SOCl$_2$, DMF, CH$_2$Cl$_2$, 0° C., 15 min, 80% (d) SOCl$_2$, MeOH, 98%; (e) LiAlH$_4$, THF, 75%; (f) SOCl$_2$, THF, 1 h, 75%.

Protected imidazole chloride derivatives (7-10) were prepared using previously reported procedures[21-23] as outlined in FIG. 2, Scheme 2. Compounds with the imidazole group substituted on the N-1 position of piperazinone ring were prepared by alkylation of the amide nitrogen in compounds 12a-12d (See FIG. 3, Scheme 3). Protected scaffolds 12a-12d were synthesized using procedures similar to that of scaffold 3, except that the reductive amination step was omitted to leave the N-1 position open for further substitution. The acid-catalyzed cyclization went smoothly for most of the scaffolds in 85%-88% yield, except for 12b (30% yield) which has a bulky naphthyl group. Allylation of 12 with Boc-protected chlorometihylimidazole 7 went to completion within 1 h at room temperature. However, the yield of the N-1 alkylation was only about 10%, while the major products resulted from C-5 alkylation. Compounds 13a2-13a4 were synthesized by reacting scaffold 12a with NaH and trityl-protected chloromethylimidazoles 8-10 in THF at 60° C. for 2 h with 35-70% yield. The temperature and reaction time were monitored carefully to prevent racemization at the C-3 chiral center. Compounds 13b-13d were synthesized from scaffolds 12b-12d, respectively, under similar conditions using 4-chloromethyl-5-methyl-1-tritylimidazole (9). Hydrogenation at atmospheric pressure using 10% Pd/C removed the Cbz protective group and the double bond, while leaving the trityl group intact. Coupling of the piperazinone scaffold 14 with commercially available isocyanates or isocyanates generated from the corresponding amino acid methyl ester afforded protected inhibitors 15. Deprotection of the trityl group using 40% TFA/CH$_2$Cl$_2$ and triethylsilane gave the methyl esters, which were then sponificated to give the corresponding acids.

Figure 4:
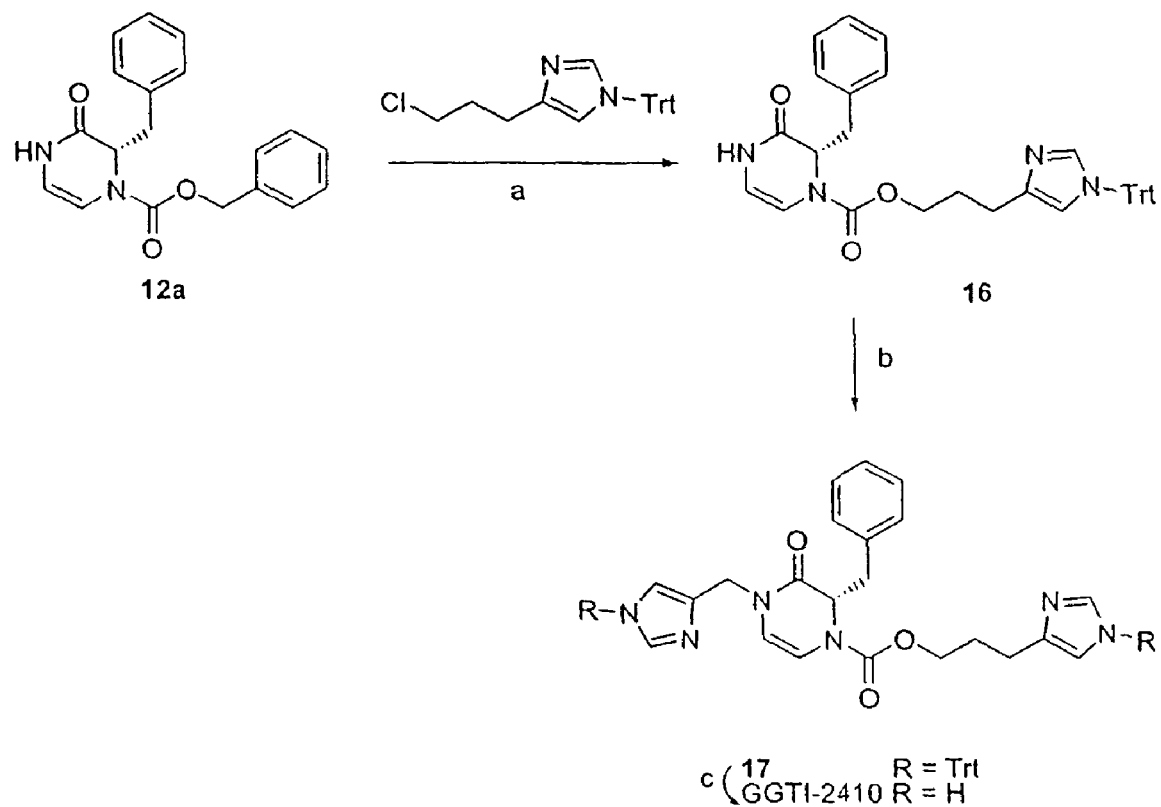
FIG. 4 shows the chemical synthesis of GGTI-2410, a compound according to the present invention. $^a$Reagents and conditions: (a) NaH, Bu$_4$NI, THF, reflux, 4 h, 40%; (b) NaH, THF, 60° C., 2 h, 70%; (c) 40% TFA/CH$_2$Cl$_2$, triethylsilane, 90%.

Initial attempts to synthesize compound 13a4 using 4-(3-chloro-propyl)-1-tritylimidazole and NaH in THF were unsuccessful. Instead, As shown in FIG. 4, Scheme 4, compound 16 was obtained using catalytic amount of Bu$_4$NI under reflux in THF. Reaction of compound 16 with NaH and 8 gave 17, which, after deprotection, generated GGTI-2410 with two imidazole substituents.

Figure 5:
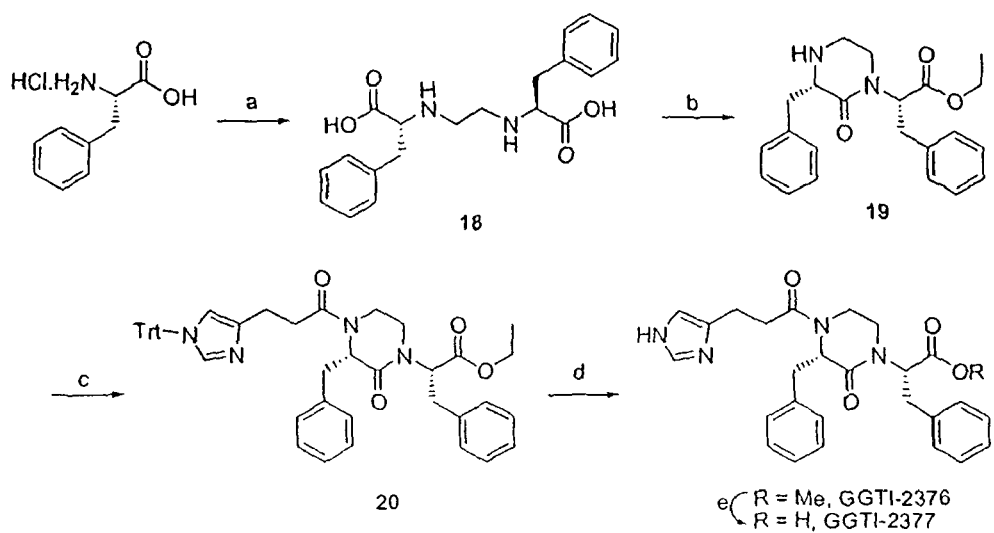
FIG. 5 shows the chemical synthesis of GGTI-2376 and GGTI-2377, compounds according to the present invention.

As shown in FIG. 5, Scheme 5, GGTI-2376 and GGTI-2377 were synthesized using Yamashita's method[24] which is useful in synthesizing constrained dipeptide mimics composed of two identical amino acids. Compound 19 was synthesized in two steps (75% and 85% yields, respectively) from L-phenylalanine via ethylene-bridged compound 18. Coupling of scaffold 19 with N-1-trityl-deaminohistidine gave compound 20, which after removal of the trityl group and saponification gave the desired products.

As shown in FIG. 6, Scheme 6, compound 21 was synthesized in 40% yield by coupling of L-leucine methyl ester with N-Cbz-L-phethylalanine using EDCI, followed by DIBAL-H reduction in CH$_2$Cl$_2$ at −78° C. Cyclization of 21 in 70% TFA/H$_2$O generated compound 22 in 87% yield. Reaction of compound 22 with NaH and trityl-protected imidazole chloride 9 gave compound 23 in poor yield (15%), presumably due to the steric hindrance between the isobutyl group at 6-position and the bulky trityl substitution on the imidazole ring. Hydrogenation of compound 23 removed the Cbz group 3 and saturated the double bond, resulting in predominately one isomer with a d.e. of 80% based on signals in the NMR spectrum. The newly generated stereocenter was predicted to be in a 6S configuration, due to the approach of the catalyst-bound hydrogen from the top face to avoid steric clash with the 3S benzyl group. The crude deprotected scaffold was coupled to L-leucine methyl ester isocyanate to give compound 24, which after purification, deprotection of the trityl group, and saponification gave methyl ester 25 and acid GGTI-2435, respectively.

The 6S stereochemistry was confirmed by 2D NMR experiments, including $^1$H—$^1$H COSEY and NOESY, of compound 25.[25] In NMR experiments, an NOE was observed between axial-H-5 and one of the H-7 protons confirming the pseudoaxial orientation of the 3S benzyl group (also as seen in the crystal structures of compounds 3 and 12a), and the axial, β orientation of H-6 (6S configuration). This is consistent with earlier studies which showed that acylation of an amino group induces an allylic (1,3)-strain-enforced pseudo-axial position of the C$_α$ side chain substituent.[26]

The amino acid urea compounds of the present invention are prepared by first forming the amino acid ester isocyanates followed by subsequent urea formation. These syntheses are described pictorially in FIG. 7, Scheme 7 and FIG. 8, Scheme 8. Pursuant to these syntheses, the piperazinone scaffold is first synthesized and R$^3$ as a methyl-substituted methylene-imidazole is introduced on the amine alpha to the ketone after piperazinone formation. The amine beta to the ketone of the piperazinone is thereafter converted to an isocyanate and then reacted with an amino acid to form the amino acid urea compound. The same procedure was employed for attaching different amino acid methyl esters to the piperazinone scaffolds through a urea linkage with 85-88% yields.

The specific synthetic steps for numerous compounds according to the present invention are detailed in the examples section of the specification which follows.

Pharmaceutical compositions based upon these novel chemical compounds comprise the above-described compounds in a therapeutically effective amount for treating one or more of a tumor and/or cancer, psoriasis, arthritis, atherosclerosis, intimal hyperplasia and chronic inflammatory diseases, including rheumatoid arthritis and osteoarthritis, among others, optionally in combination with a pharmaceutically acceptable additive, carrier or excipient. One of ordinary skill in the art will recognize that a therapeutically effective amount will vary with the infection or condition to be treated, its severity, the treatment regimen to be employed, the pharmacokinetics of the agent used, as well as the patient (animal or human) treated.

In the pharmaceutical aspect according to the present invention, the compound according to the present invention is formulated preferably in admixture with a pharmaceutically acceptable carrier. In general, it is preferable to administer the pharmaceutical composition in orally-administrable form, but certain formulations may be administered via a parenteral, intravenous, intramuscular, transdermal, buccal, subcutaneous, suppository or other route. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect in patients.

In certain pharmaceutical dosage forms, the pro-drug form of the compounds, especially including acylated (acetylated or other) and ether (alkyl and related) derivatives, phosphate esters and various salt forms of the present compounds, are preferred. One of ordinary skill in the art will recognize how to readily modify the present compounds to pro-drug forms to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound.

The amount of compound included within therapeutically active formulations according to the present invention is an effective amount for treating tumor and/or cancer, psoriasis, arthritis, atherosclerosis, intimal hyperplasia and chronic inflammatory diseases, including rheumatoid arthritis and osteoarthritis. In general, a therapeutically effective amount of the present compound in pharmaceutical dosage form usually ranges from about 0.05 mg/kg to about 100 mg/kg per day or more, more preferably, less than about 1 mg/kg. to about 25 mg/kg per day of the patient or considerably more, depending upon the compound used, the condition or infection treated and the route of administration. In the case of tumors and/or cancer, the active compound is preferably administered in amounts ranging from about 0.5 mg/kg to about 25 mg/kg per day of the patient, depending upon the pharmacokinetics of the agent in the patient. This dosage range generally produces effective blood level concentrations of active compound. For purposes of the present invention, in many instances, a prophylactically or preventive effective amount of the compositions according to the present invention falls within the same concentration range as set forth above for therapeutically effective amount and is usually the same as a therapeutically effective amount.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester pro-drug forms of the nucleoside compounds according to the present invention.

In particularly preferred embodiments according to the present invention, the compounds and compositions are used to treat, prevent or delay the onset of any one or more of tumors and/or cancer, psoriasis, arthritis, atherosclerosis, intimal hyperplasia and chronic inflammatory diseases, including rheumatoid arthritis and osteoarthritis in mammals, especially humans. In its preferred embodiments, the compounds are used to treat tumors and/cancers such as in humans. Preferably, to treat, prevent or delay the onset of one or more of these infections, the compositions will be administered in oral dosage form in amounts ranging from about 250 micrograms up to about 500 mg or more at least once a day, preferably, up to four times a day. The present compounds are preferably administered orally, but may be administered parenterally, topically or in suppository form.

The compounds according to the present invention, because of their low toxicity to host cells, may advantageously be employed prophylactically to prevent tumor and/or cancer, psoriasis, arthritis, atherosclerosis, and chronic inflammatory diseases, including rheumatoid arthritis and osteoarthritis, or to prevent the occurrence of clinical symptoms associated with the viral infection. Thus, the present invention also encompasses methods for the prophylactic treatment of tumors and/or cancer, and in particular, benign and malignant neoplasia, including various cancers such as, stomach, colon, rectal, liver, pancreatic, lung, breast, cervix uteri, corpus uteri, ovary, prostate, testis, bladder, renal, brain/cns, head and neck, throat, Hodgkins disease, non-Hodgkins leukemia, multiple myeloma leukemias, skin melanoma, acute lymphocytic leukemia, acute mylogenous leukemia, Ewings Sarcoma, small cell lung cancer, choriocarcinoma, rhabdomyosarcoma, Wilms Tumor, neuroblastoma, hairy cell leukemia, mouth/pharynx, oesophagus, larynx, melanoma, kidney, lymphoma, among others. In this aspect according to the present invention, the present compositions are used to prevent reduce the likelihood of or delay the onset of tumors and/or cancer. This prophylactic method comprises administering to a patient in need of such treatment or who is at risk for the development of one or more tumors and/or cancer, psoriasis, arthritis, atherosclerosis, intimal hyperplasia and chronic inflammatory diseases, including rheumatoid arthritis and osteoarthritis, among others, an amount of a compound according to the present invention effective for alleviating, preventing or delaying the onset of the infection. In the prophylactic treatment according to the present invention, it is preferred that the compound utilized should be as low in toxicity and preferably non-toxic to the patient. It is particularly preferred in this aspect of the present invention that the compound which is used should be maximally effective against the tumors and/or cancer and should exhibit a minimum of toxicity to the patient. In the case of compounds of the present invention for the prophylactic treatment of any one or more of the treated conditions or disease states, the present compounds may be administered within the same dosage range for therapeutic treatment (i.e., about 250 micrograms up to about 500 mg, or more from one to four times per day for an oral dosage form) as a prophylactic agent to prevent the proliferation of the disease state or alternatively, to prolong the onset of or reduce the likelihood of a patient contracting a condition or a disease state which manifests itself in clinical symptoms.

In addition, compounds according to the present invention may be administered alone or in combination with other agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

As indicated, compounds according to the present invention may be administered alone or in combination with other agents, especially including other compounds of the present invention or compounds which are otherwise disclosed as being useful for the treatment of tumor and/or cancer, psoriasis, arthritis, atherosclerosis, intimal hyperplasia and chronic inflammatory diseases, including rheumatoid arthritis and osteoarthritis, among others, including those presently used to treat one or more of these disease states.

Compounds used in the art may be used in combination with the present compounds for their additive activity or treatment profile against tumor and/or cancer, psoriasis, arthritis, atherosclerosis, intimal hyperplasia and chronic inflammatory diseases, including rheumatoid arthritis and osteoarthritis, among others and in certain instances, for their synergistic effects in combination with compounds of the present invention. Preferred secondary or additional compounds for use with the present compounds are those which do not inhibit tumor and/or cancer, psoriasis, arthritis, atherosclerosis, and chronic inflammatory diseases, including rheumatoid arthritis and osteoarthritis, among others by the same mechanism as those of the present invention. Certain compounds according to the present invention may be effective for enhancing the biological activity of certain agents according to the present invention by reducing the metabolism or inactivation of other compounds and as such, are co-administered for this intended effect.

In a particularly preferred pharmaceutical composition and method aspect of the present invention for treating tumors, especially including malignant cancer, an inhibitory effective amount of the present compound is administered to a patient suffering from such a condition to treat the condition and alleviate the symptoms of such disease state.

The present invention is now described, purely by way of illustration, in the following examples. It will be understood by one of ordinary skill in the art that these examples are in no way limiting and that variations of detail can be made without departing from the spirit and scope of the present invention.

EXAMPLES

Nuclear magnetic resonance spectra ($^1$H, 400 or 500 MHz), ($^{13}$C, 100 or 125 MHz) were acquired using Bruker-500 or Bruker-400 spectrometers, and are reported in δ (ppm) with TMS as the internal reference. The homogeneity of all the compounds was routinely checked by TLC on silica gel plates, and all synthesized final products were checked for purity by HPLC using a Rainin 250×4.6 mm, 5 μm Microsorb C18 column. High-resolution mass spectra (EI or FAB) were recorded on a Micro-mass VSE and Micro-mass 70-4F mass spectrometers, respectively. Melting points were obtained on an Electrochem melting point apparatus and are uncorrected.

General Procedure for the Syntheses of Amino Acid Ester Isocyanates and Subsequent Urea Formation.

Amino acid methyl ester hydrochloride (0.6 mmol) was suspended in 2.0 mL of $CH_2Cl_2$, and to the solution was added 0.2 mL of pyridine (2.4 mmol). The resulting suspension was cooled at 0° C. for 15 min. Then a solution of phosgene (20% in toluene, 0.4 mL, 0.72 mmol) (CAUTION: USE HOOD) was added by syringe. The resulting mixture was stirred at 0° C. under $N_2$ for 2 h. The solution was then diluted to a volume of 8 mL with $CH_2Cl_2$, extracted with 10 mL of cold 0.1 N HCl, and ca. 7 mL of crushed ice. Each aqueous phases was re-extracted with 4 mL of $CH_2Cl_2$. The combined organic phases were extracted with cold brine, dried over $Na_2SO_4$. The resulting isocyanate solution was used for the subsequent urea formation reaction without further purification.

To a 25 mL round flask charged with piperazinone scaffold (0.25 mmol) was added a fraction of the above solution (ca. 0.30 mmol, assuming 90% yield according to the literature[29]). The mixture was stirred under $N_2$ at 0° C. for 1 h, and at rt for 4 h. Then the solvent was removed under reduced pressure and the resulting residue was subjected to silica gel column chromatography using 1-5% MeOH/$CH_2Cl_2$ as eluant to afford the urea. The same procedure was employed for attaching different amino acid methyl esters to the piperazinone scaffolds through a urea linkage with 85-88% yields.

Figure 1:
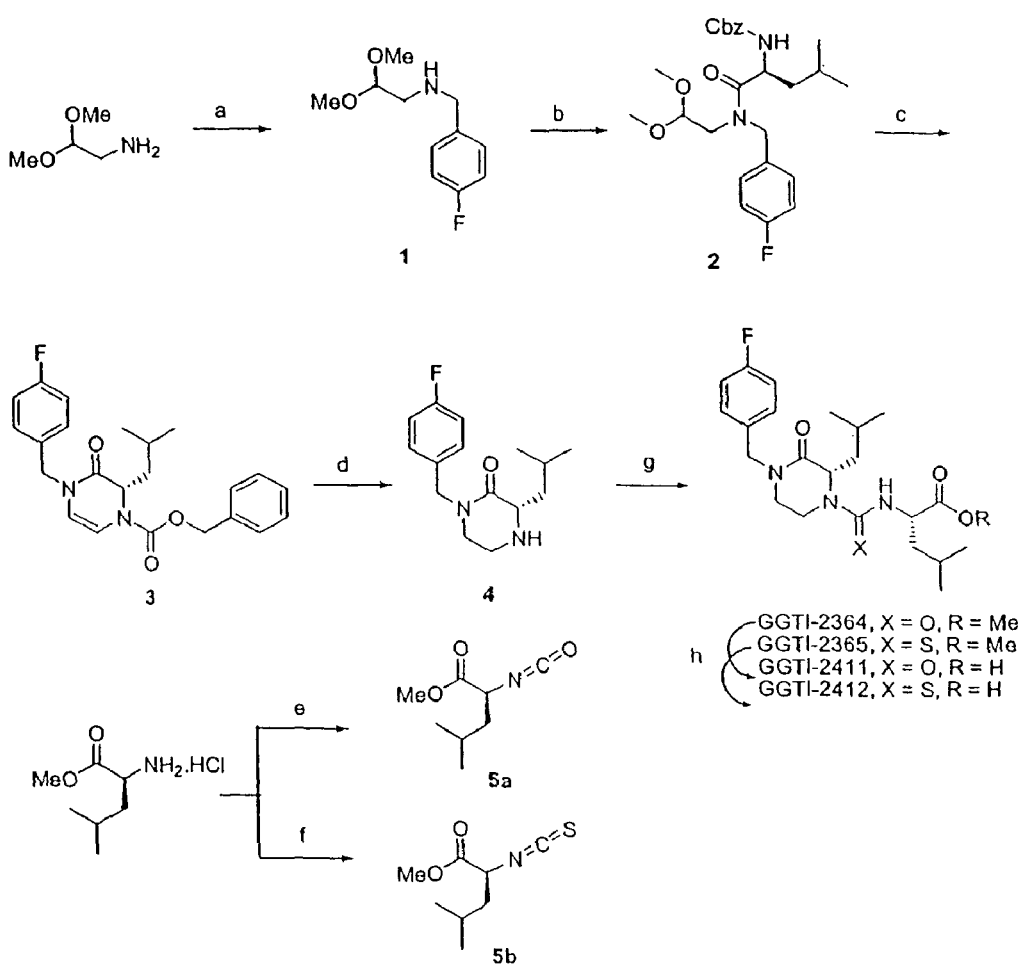
FIG. 1 shows the chemical synthesis of certain GGTI analogs 2364, 2365, 2411 and 2412 according to the present invention. $^a$Reagents and conditions: (a) p-fluorobenzaldehyde, NaBH(OAc)$_3$, DCE, 24 h, 95%; (b) N-Cbz-L-Leu, EDCI, DIEA, CH$_2$Cl$_2$, 3 h, 98%; (c) 70% TFA/H$_2$O, 2 h, 90%; (d) H$_2$, 10% Pd/C, EtOAc/MeOH, 4 h, 98%; (e) COCl$_2$, CH$_2$Cl$_2$, pyridine, 2 h, 90%; (f) CSCl$_2$, H$_2$O, Na$_2$CO$_3$, 0.5 h, yield 65%; (g) 5a or 5b, CH$_2$Cl$_2$, 0° C.-rt, 5 h; 85-90% (h) NaOH/H$_2$O, MeOH, 90%.

Syntheses of GGTI-2364, GGTI-2365, GGTI-2411, GGTI-2412 (Scheme 1, FIG. 1)

To a solution of aminoacetaldehyde dimethyl acetal (1.1 mL, 10 mmol) in dichlorolethane was added 4-fluorobenzaldhyde (1.07 mL, 10 mmol) and glacial acetic acid 0.5 mL. The reaction mixture was stirred at rt for 0.5 h, then sodium triacetoxyboron hydride (2.6 g, 13 mmol) was added at one time. The reaction mixture was stirred under $N_2$ for 3 h, then an additional 400 mg of sodium triacetoxyboron hydride was added and the mixture was stirred at rt for another 5-7 h. The reaction was stopped by quenching with 1N NaOH in an ice bath. The mixture was extracted with methylene chloride. The combined organic phases were dried over sodium carbonate, filtered and the solvent was removed under vacuo to give compound 1 as a colorless oil (2.1 g, 92%), which was used without further purification.

A mixture of crude 1 (1.2 g, 5.6 mmol), Cbz-L-leucine (1.2 g, 0.55 mmol), EDCI (1.07 g, 5.6 mmol), DIEA (0.9 mL, 5.6 mmol) in 20 mL anhydrous methylene chloride was stirred at rt for 5 h. The reaction mixture was diluted with 80 mL methylene chloride, and the solution was washed with 1N HCl (20 mL), sat. sodium bicarbonate solution (20 mL), and brine (20 mL). The organic phase was dried over sodium sulfate and the solvent was removed under reduced pressure to give a crude oil, which was purified by silica gel column chromatography with hexanes/EtOAc (5:1) as eluant to afford compound 2 as a colorless oil (2.2 g, 95%): $^1$H NMR (MeOH, 500 MHz) δ 0.73 (d, J=6.5 Hz, 1.27H), 0.84 (d, J=7.0 Hz, 1.45H), 0.95 (d, J=7.0 Hz, 3.3H), 1.17-1.77 (m, 3H), 3.07-3.27 (m, 1H), 3.48 (dd, J=14.0, 5.5 Hz, 0.5H), 3.73 (dd, J=15.5, 6.5 Hz, 0.5 H), 4.52 (dd, J=11.0, 5.5 Hz, 1H), 4.57-4.82 (m, 3H), 5.06 (d, J=12.5 Hz, 1H), 5.11 (d, J=12.5 Hz, 1H), 7.00 (t, J=8.5 Hz, 1H), 7.07 (t, J=9.0 Hz, 1H), 7.21 (dd, J=8.5, 5.5 Hz, 1H), 7.27 (dd, J=8.5, 5.5 Hz, 1H), 7.32 (m, 5H);

Compound 2 (2.0 g, 4.33 mmol) was dissolved in 20 mL 70% TFA/H$_2$O and the solution was stirred at rt for 2 h. The solvent was removed on a rotovap to give a yellowish oil, which was dissolved in 100 mL ethyl acetate and washed with saturated aqueous NaHCO$_3$ solution and brine. The organic phase was dried over anhydrous Na$_2$SO$_4$, and the solvent was removed to give compound 3 as a white solid (1.55 g, 91%). Single crystal was obtained by slow evaporation a chloroform solution of compound 3: m.p. 91-92° C.; $^1$H NMR (MeOH, 500 MHz) δ 0.78 (d, J=6.0 Hz, 1H), 0.83 (d, J=6.0 Hz, 1H), 0.91 (d, J=6.0 Hz, 2H), 0.94 (d, J=6.0 Hz, 2H), 1.40-1.53 (m, 3H), 4.65 (d, J=7.0 Hz, 2H), 4.72 (m, 0.5H), 4.83 (m, 0.5H), 5.09-5.26 (m, 2H), 5.80 (d, J=6.0 Hz, 0.5 H), 5.90 (d, J=6.0 Hz, 0.5H), 6.32 (d, J=5.5 Hz, 0.5H), 6.29 (d, J=5.5 Hz, 0.5 H), 7.02 (d, J=8.5 Hz, 1H), 7.04 (d, J=8.5 Hz, 1H), 7.26 (d, J=8.5, 6.0 Hz, 2H), 7.32 (m, 5H); HRMS (FAB, m/z) calcd. for C$_{23}$H$_{26}$FN$_2$O$_3$(M$^+$+1) 397.1927, observed 397.1926.

Compound 3 (1.5 g, 3.78 mmol) was dissolved in 40 mL MeOH/EtOAc (1:1), and to the solution was added 10% Pd/C. The solution was hydrogenated at atmospheric pressure for 4 h. The solution was filtered and the solvent removed to give compound 4 as a colorless oil (0.98 g, 99%): $^1$H NMR (CDCl$_3$, 500 MHz) δ0.88 (d, J=6.5 Hz, 3H), 0.91 (d, J=6.5 Hz, 3H), 1.51 (ddd, J=14.0, 10.5, 4.5 Hz, 1H), 1.72 (m, 1H), 1.86 (ddd, J=14.0, 10.5, 4.0 Hz, 1H), 2.89 (ddd, J=13.5, 10.5, 4.5 Hz, 1H), 3.08 (m, 2H), 3.23 (m, 1H), 3.42 (dd, J=10.0, 3.5 Hz, 1H), 4.40 (d, J=15.0 Hz, 1H), 4.55 (d, J=15.0 Hz, 1H), 6.93 (d, J=8.5 Hz, 1H), 6.95 (d, J=8.5 Hz, 1H), 7.17 (dd, J=8.5, 5.5 Hz, 2H); HRMS (FAB, m/z) calcd. for C$_{15}$H$_{22}$FN$_2$O (M$^+$+1) 265.1716, observed 265.1716.

Reaction of compound 4 with the isocyanate generated from L-leucine methyl ester (general procedure) afford GGTI-2364 as a colorless oil in 85% yield: $^1$H NMR (MeOH, 500 MHz) δ0.87 (d, J=6.5 Hz, 3H), 0.93 (d, J=6.5 Hz, 3H), 0.95 (d, J=6.5 Hz, 3H), 0.96 (d, J=6.6 Hz, 3H), 1.53-1.80 (m, 6H), 3.18 (m, 1H), 3.39 (m, 2H), 3.67 (s, 3H), 3.98 (m, 1H), 4.27 (dd, J=10.0, 4.5 Hz, 1H), 4.57 (d, J=4.5 Hz, 2H), 4.83 (m, 1H), 7.04 (d, J=9.0 Hz, 1H), 7.06 (d, J=9.0 Hz, 1H), 7.27 (dd, J=9.0, 5.5 Hz, 2H); HRMS (FAB, m/z) calcd. for C$_{23}$H$_{35}$N$_3$O$_4$F (M$^+$+1) 436.2612, observed 436.2612.

To a solution of GGTI-2364 (100 mg, mmol) in 0.5 mL methanol was added 1 mL 1N NaOH solution. The resulting mixture was stirred at rt for 1 h, then the solvent was removed under reduced pressure. The residue was suspended in 2 mL of 30% MeOH/CH$_2$Cl$_2$, and the suspension was passed through a pad of silica gel (500 mg). The solid phase was further eluted with 30%-50% MeOH/CH$_2$Cl$_2$ solution. The factions containing the pure product were combined and the solvent was removed to afford GGTI-2365 as a colorless oil in 80% yield: $^1$H NMR (MeOH, 500 MHz) δ0.78 (d, J=6.0 Hz, 3H), 0.82 (d, J=6.0 Hz, 3H), 0.85 (d, J=6.0 Hz, 3H), 0.88 (d, J=6.0 Hz, 3H), 1.50-1.60 (m, 6H), 3.08 (m, 1H), 3.33 (m, 2H), 3.90 (brd, J=4.5 Hz, 1H), 4.18 (dd, J=10.5, 5.0 Hz, 1H), 4.47 (brs, 2H), 4.75 (dd, J=9.5, 2,5 Hz, 1H), 6.94 (d, J=8.5 Hz, 1H), 6.96 (d, J=8.5 Hz, 1H), 7.17 (dd, J=8.5, 5.0 Hz, 2H); HRMS (FAB, m/z) calcd. for C$_{22}$H$_{33}$N$_3$O$_4$F (M$^+$+1) 422.2455, observed 422.2455.

Syntheses of L-leucine methyl ester isothiocyanate. L-leucine methyl ester hydrochloride (110 mg, 0.6 mmol) was dissolved in 0.3 mL of water and stirred with 1 mL of chloroform at 0° C. The pH was adjusted to 9.0 with aqueous sodium carbonate solution. Then a solution of thiophlosgene 70 μL (1.0 mmol) in 150 μL CHCl$_3$ was added dropwise with stirring while the pH was kept at 9.0 with sodium carbonate solution. After 30 min stirring at 0° C., the organic phase was separated, and diluted to a volume of 8 mL with CHCl$_3$. The solution was extracted with 10 mL of cold 0.1 N HCl, and ca. 7 mL of crushed ice. Each aqueous phases was re-extracted with 4 mL of CHCl$_3$. The combined organic phases were extracted with cold brine, and dried over Na$_2$SO$_4$. The resulting isothiocyanate solution was used for the subsequent urea formation reaction without further purification.

To a 25 mL round flask charged with piperazinone scaffold 4 (100 mg, 0.38 mmol) was added a fraction (1.2 equiv.) of the above solution. The mixture was stirred under N$_2$ at 0° C. for 1 h, and at rt for 4 h. Then the solvent was removed under reduced pressure and the resulting residue was subjected to silica gel column chromatography using 0.5-2.5% MeOH/CH$_2$Cl$_2$ as eluant to afford the thiourea GGTI-2411 (140 mg, 83% yield) as colorless oil: $^1$H NMR (CDCl$_3$, 500 MHz) δ 0.94 (d, J=6.2 Hz, 6H), 1.01 (d, J=6.7 Hz, 6H), 1.65 (m, 2H), 1.72 (m, 2H), 1.81 (m, 1H), 1.90 (m, 1H), 3.15 (m, 1H), 3.45 (m, 2H), 3.73 (s, 3H), 4.30 (d, J=14.5 Hz, 1H), 4.73 (d, J=14.5 Hz, 1H), 4.79 (m, 1H), 4.93 (m, 1H), 5.18 (dd, J=13.2, 7.0 Hz, 1H), 5.91 (d, J=7.5 Hz, 1H), 7.00 (t, J=8.5 Hz, 2H), 7.20 (dd, J=8.5, 5.5 Hz, 2H); MS (FAB, m/z) 452, M$^+$+1−SH$_2$.

Saponification of GGTI-2411 in a manner similar to that described for the synthesis of GGTI-2365, afforded GGTI-2412 as colorless oil in 80% yield: $^1$H NMR (CDCl$_3$, 400 MHz) δ 0.93 (d, J=6.5 Hz, 3H), 0.98 (m, 12H), 1.61-1.83 (m, 6H), 3.12 (brd, J=12.5 Hz, 1H), 3.40 (m, 2H), 4.16 (d, J=14.5 Hz, 1H),4.83 (d, J=14.5 Hz, 1H), 5.37 (m, 2H), 5.47 (brd, J=14.0 Hz, 1H), 6.63 (d, J=7.0 Hz, 1H), 7.01 (t, J=8.5 Hz, 2H), 7.18 (dd, J=8.5, 5.5 Hz, 2H); MS (FAB, m/z) 438, M$^+$+1−SH$_2$.

Figure 3:
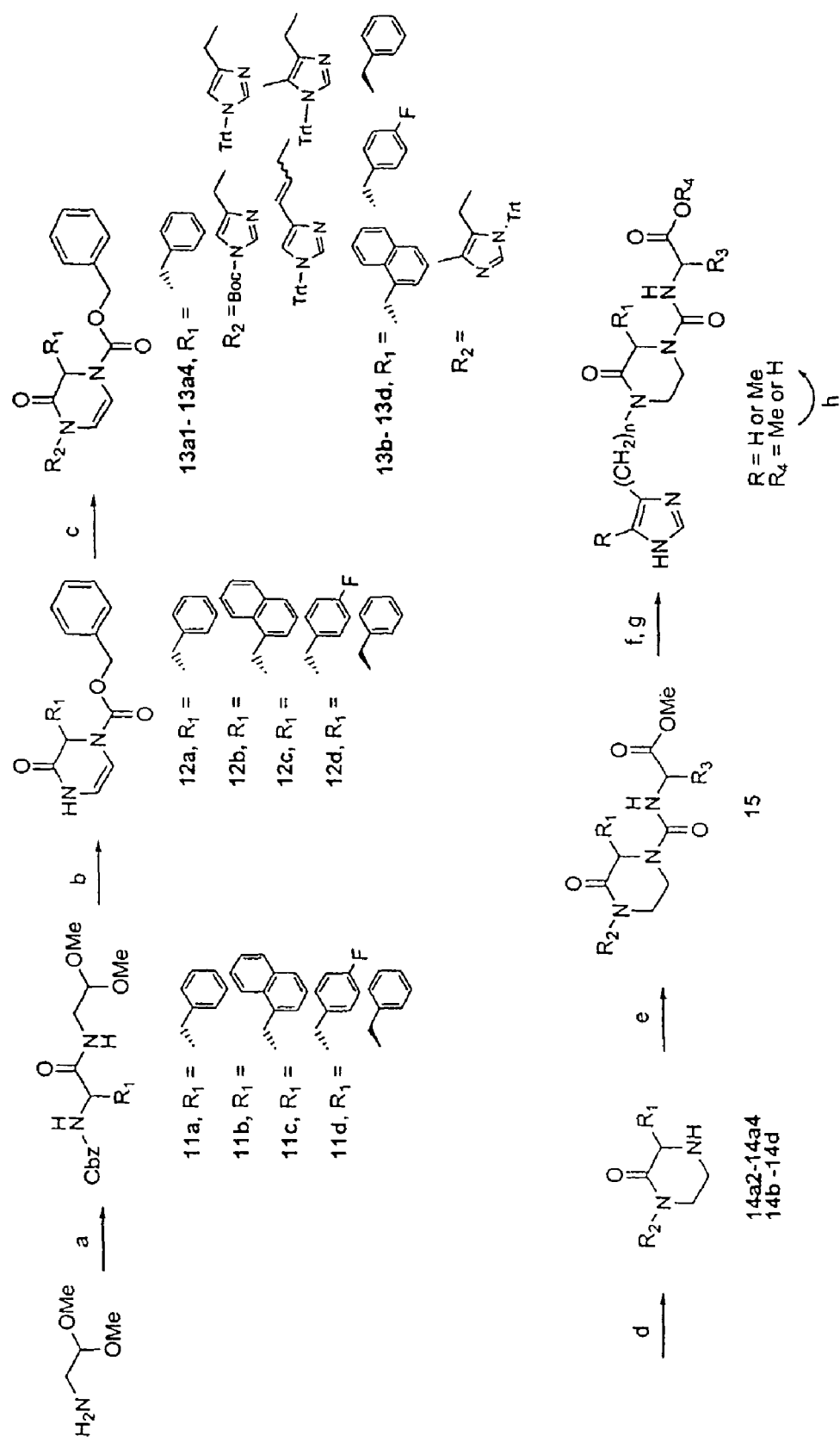
FIG. 3 shows the chemical synthesis of certain chemical analogs according to the present invention, as described. $^a$Reagents and conditions: (a) N-Cbz-amino acid, EDCI, DIEA, CH$_2$Cl$_2$, 90-95%; (b) 70% TFA/H$_2$O, 30-88%; (c) NaH, 7-10, THF, 60° C., 2 h, 15-70%; (d) H$_2$, 10% Pd/C, EtOAc/MeOH, 98%; (f) amino acid methyl ester isocyanates, CH$_2$Cl$_2$, 0° C.-rt, 4 h, 85-88%; (g) 40% TFA/CH$_2$Cl$_2$, triethylsilane, 90-95%; (h)1N NaOH/H$_2$O, MeOH, 90%.

Synthesis of GGTI-2421, GGTI-2422 (Following Scheme 3, FIG. 3)

A mixture of aminoacetaldlhyde dimethyl acetal (1.1 mL, 10 mmol), Cbz-L-leucine (2.99 g, 10 mmol), EDCI (1.92 g, 10 mmol), in 20 mL anhydrous methylene chloride was stirred at rt for 5 h. The reaction mixture was diluted with 80 mL methylene chloride, and the solution was washed with 1N HCl (20 mL), saturated sodium bicarbonate solution (20 mL), and brine (20 mL). The organic phase was dried over sodium sulfate, and passed through a pad of silica gel, and the solid phase was washed with 1-2.5% MeOH/CH$_2$Cl$_2$. Fractions were combined and the solvent was removed to afford compound 11a as a white solid (3.3 g, 86%): m.p. 123-124° C.; $^1$H NMR (MeOH, 500 MHz) δ2.72 (dd, J=14.0, 9.0 Hz, 1H), 2.95 (dd, J=14.0, 6.0 Hz, 1H), 3.13 (m, 2H), 3.18 (s, 6H), 4.17 (t, J=6.0 Hz, 1H), 4.23 (dd, J=9.0, 6.0 Hz, 1H), 4.87 (d, J=13.0, Hz, 1H), 4.91 (d, J=13.0 Hz, 1H), 7.06-7.20 (m, 10H); HRMS (FAB, m/z) calcd. for C$_{21}$H$_{27}$N$_2$O$_5$ (M$^+$+1) 387.1920, observed 387.1917.

Compound 11a (3.0 g, 7.8 mmol) was dissolved in 30 mL 70% TFA/H$_2$O and the solution was stirred at rt for 2 h. The solvent was removed on a rotovap to give a yellow oil, which was dissolved in 150 mL ethyl acetate and washed with saturated NaHCO$_3$ and brine. The organic phase was dried over anhydrous Na$_2$SO$_4$, and the solvent removed to give compound 12a as a white solid (2.1 g, 84%). Single crystal was obtained by slow evaporation of a hexanes/EtOAc solution of 12a: m.p. 141-142° C.; $^1$H NMR (MeOH, 500 MHz)

δ 2.77-2.85 (m, 2H), 4.41 (d, J=12.5 Hz, 0.5H), 4.66 (ddd, J=9.0, 5.0, 1.5 Hz, 0.5H), 4.77 (m, 0.5H), 4.80 (d, J=12.0 Hz, 0.5H), 4.88 (d, J=12.5 Hz, 0.5H), 4.99 (d, J=12.5 Hz, 0.5H), 5.44 (d, J=6.0 Hz, 0.5H), 5.67 (d, J=6.0 Hz, 0.5H), 6.08 (dd, J=6.0, 1.5 Hz, 0.5H), 6.19 (dd, J=6.0, 1.5 Hz, 0.5H), 6.95-7.24 (m, 10H); HRMS (FAB, m/z) calcd. for $C_{19}H_{19}N_2O_3$ ($M^+ + 1$) 323.1396, observed 323.1396.

To a stirred solution of compound 12a (966 mg, 3.0 mmol) in 12 mL anhydrous THF was added 60% NaH (120 mg, 3.0 mmol) at 0° C. The solution was stirred at rt for 0.5 h. Then 4-chloromethyl-1-Boc-imidazole (7, 700 mg, 3.2 mmol) was added, and the solution was stirred at rt for 0.5 h. The reaction mixture was then cooled to room temperature and the solvent was removed on a rotovap. The resulting residue was dissolved in EtOAc, washed with aqueous $NH_4Cl$ solution and brine. The organic phase was dried over $Na_2SO_4$ and concentrated to give a yellow oil, which was subjected to silica gel column chromatography using hexanes/EtOAc (3:1-1:1) to afford GGTI-2421 (13a1) as a colorless oil (150 mg, 10%): $^1H$ NMR ($CDCl_3$, 400 MHz) δ 1.53 (s, 9H), 2.86 (m, 2H), 4.35-4.60 (m, 2.5 H), 4.84-5.04 (m, 2.5 H), 5.58 (d, J=6.0 Hz, 0.5 H), 5.79 (d, J=6.0 Hz, 0.5 H), 6.10 (d, J=6.0 Hz, 0.5H), 6.31 (d, J=6.0 Hz, 0.5 H), 6.96-7.30 (m, 11H), 7.95 (s, 1H); HRMS (FAB, m/z) calcd. for $C_{28}H_{31}N_4O_5$ ($M^+ + 1$) 503.2294, observed 503.2294.

GGTI-2421 (100 mg, 0.2 mmol) was treated with 2 mL 20% $TFA/CH_2Cl_2$ at rt for 1 h. After removal of the solvent, CGTI-2422 was obtained as a colorless oil (78 mg, 97%): $^1H$ NMR ($CDCl_3$, 500 MHz) δ 2.82 (m, 2H), 4.48 (m, 1.5 H), 4.73 (m, 1H), 4.83-5.05 (m, 2.5H), 5.49 (d, J=6.0 Hz, 0.5 H), 5.70 (d, J=6.0 Hz, 0.5 H), 6.19 (d, J=6.0 Hz, 0.5 H), 6.34 (d, J=6.0 Hz, 0.5 H), 6.88-7.28 (m, 11H), 8.38 (s, 11H); HRMS (FAB, m/z) calcd. for $C_{23}H_{23}N_4O_3$ ($M^+ + 1$) 403.1770, observed 403.1770.

Syntheses of GGTI-2413, GGTI-2414, GGTI-2415, GGTI-2416 (Scheme 3, FIG. 3)

To a stirred solution of compound 12a (1 g, 3.1 mmol) in 14 mL anhydrous THF was added 60% NaH (124 mg, 3.1 mmol) at 0° C. The solution was stirred at rt for 0.5 h. Then 4-chloromethyl-1-tritylimidazole[21] (8, 850 mg, 3.1 mmol) was added, and the solution was stirred at 60° C. for 2 h. The reaction mixture was then cooled to room temperature and the solvent was removed on a rotovap. The residue obtained was subjected to silica gel column chromatography using hexanes/EtOAc (3:1-1:1) to afford compound 13a2 as a colorless oil (1.2 g, 60%): $^1H$ NMR (MeOH, 500 MHz) δ 2.71 (m, 2H), 4.43 (m, 1.5H), 4.54 (d, J=15.0 Hz, 0.5H), 4.57 (d, J=15.0 Hz, 0.5H), 4.70 (m, 0.5H), 4.75 (m, 0.5H), 4.80 (d, J=12.0 Hz, 0.5H), 4.87 (d, J=12.0 Hz, 0.5H), 4.96 (d, J=12.5 Hz, 0.5H), 5.55 (d, J=6.0 Hz, 0.5H), 5.76 (d, J=6.0 Hz, 0.5H), 6.10 (dd, J=6.0, 1.5 Hz, 0.5H), 6.22 (dd, J=6.0, 1.5 Hz, 0.5H), 6.76 (s, 1H), 6.85-7.28 (m, 20H), 7.30 (s, 1H); HRMS (FAB, m/z) calcd. for $C_{42}H_{37}N_5O_4$ ($M^+ + 1$) 645.2866, observed 645.2865.

Compound 13a2 (1.2 g, 1.86 mmol) was dissolved in 30 ml MeOH/EtOAc (2:1) and to the solution was added 10% Pd/C. The mixture was hydrogenated at atmospheric pressure overnight. Then the solution vas filtered, and the solvent was removed to give compound 14a2 as a colorless oil (0.92 g, 97%): $^1H$ NMR ($CDCl_3$, 500 MHz) δ 2.50 (m, 2H), 3.00 (m, 2H), 3.22 (t, J=5.0 Hz, 1H), 2.26 (dd, J=8.0, 5.0 Hz, 1H), 3.60 (dd, J=11.5, 5.0 Hz, 1H), 4.39-4.57 (m, 3H), 6.90 (s, 1H), 7.07-7.39 (m, 20H), 7.42 (s, 1H); HRMS (FAB, m/z) calcd. for $C_{34}H_{33}N_7O$ ($M^+ + 1$) 513.2654, observed 513.2653.

Reaction of scaffold 14a2 with L-methionine methyl ester isocyanate following previously described general procedures gave trityl-protected GGTI-2413 as a colorless oil (160 mg, 81%): $^1H$ NMR ($CDCl_3$, 500 MHz) δ 1.52 (m, 1H), 1.79 (m, 1H), 2.02 (m, 3H), 2.18 (m, 2H), 2.87 (ddd, J=14.2, 11.0, 3.5 Hz, 1H), 3.01 (dd, J=14.0, 9.0 Hz, 1H), 3.14 (brd, J=12.0 Hz, 1H), 3.32 (dd, J=13.5, 3.5 Hz, 1H), 3.40 (ddd, J=12.0, 12.0, 4.0 Hz, 1H), 3.67 (s, 3H), 4.03 (brd, J=13.0 Hz, 1H), 4.28-4.40 (m, 2H), 4.33 (d, J=14.5 Hz, 1H), 4.43 (dd, J=8.5, 3.0 Hz, 1H), 4.65 (d, J=14.5 Hz, 1H), 6.78 (s, 1H), 7.06-7.12 (m, 6H), 7.16-7.25 (m, 5H), 7.28-7.34 (m, 9H), 7.38 (s, 1H); HRMS (FAB, m/z) calcd. for $C_{41}H_{44}N_5O_4S$ ($M^+ + 1$) 702.3114, observed 702.3116.

General Procedure for Deprotection and Hydrolysis.

Trityl-protected compound 15 (0.2 mmol), was dissolved in 2 mL of 40% $TFA/CH_2Cl_2$. Triethylsilane was added dropwise until the deep yellow color disappeared. The mixture was stirred at rt for 1 h. The solvent was removed and the resulting residue was dried under reduced pressure to give a yellow solid. After washing with hexanes, the residue was subjected to silica gel column chromatography using $CH_2Cl_2$ followed by 5-10% $MeOH/CH_2Cl_2$ as eluant. The fractions were combined and concentrated to afford a colorless oil. The deprotected product (0.2 mmol) was then dissolved in a 0.5 mL of MeOH, and then 1 mL of 1N NaOH. The mixture was stirred at rt for 1 h. The solvent was removed under reduced pressure, and the resulting residue was suspended in 2 mL of 30% $MeOH/CH_2Cl_2$, and the suspension was passed through a pad of silica gel. The solid phase was further eluted with 30%-50% $MeOH/CH_2Cl_2$ solution. The fractions containing the product were combined and the solvent was removed to afford the target molecules in 80-85% yields.

Deprotection of the trityl-protected GGTI-2413 following the general procedure described above afforded GGTI-2413 as a colorless oil in 85% yield: $^1H$ NMR ($CDCl_3$, 500 MHz) δ 1.56 (m, 1H), 1.79 (m, 1H), 1.96 (m, 3H), 2.18 (t, J=7.2 Hz, 2H), 2.94 (m, 1H), 3.02 (m, 2H), 3.20 (brd, J=12.0 Hz, 1H), 3.39 (m, 1H), 3.59 (s, 3H), 4.02 (brd, J=13.0 Hz, 1H), 4.25 (dd, J=12.5, 7.0 Hz, 1H), 4.42 (d, J=15.4 Hz, 1H), 4.63 (m, 2H), 5.02 (brs, 1H), 7.06-7.30 (m, 6H), 8.58 (s, 1H); $^{13}C$ NMR ($CDCl_3$, 125 MHz) δ 15.68, 30.42, 31.80, 37.88, 37.48, 41.52, 47.09, 52.73, 53.34, 60.28, 118.54, 126.66, 127.74, 129.26, 129.27, 129.82, 129.95, 134.55, 137.47, 156.64, 168.80, 173.60; HRMS (FAB, m/z) calcd. for $C_{22}H_{30}N_5O_4S$ ($M^+ + 1$) 460.2019, observed 460.2018.

Saponification of GGTI-2413 following the general procedure afforded GGTI-2414 as a colorless oil in 88% yield: $^1H$ NMR ($CDCl_3$, 500 MHz) δ 1.66 (m, 1H), 1.88 (m, 1H), 1.92 (m, 3H), 2.20 (m, 2H), 2.75 (ddd, J=14.0, 10.5, 3.5, 1H), 2.86 (brd, J=12.3 Hz, 1H), 3.10-3.15 (m, 2H), 3.20 (m, 1H), 3.75 (brd, J=13.0 Hz, 1H), 4.04 (dd, J=8.0, 4.5 Hz, I R), 4.35 (d, J=14.8 Hz, 1H), 4.48 (d, J=14.8 Hz, 1H), 4.65 (t, J=5.2 Hz, 1H), 6.92 (s, 1H), 7.04-7.14 (m, 5H), 7.58 (s, 1H); $^{13}C$ NMR ($CDCl_3$, 125 MHz) δ 15.71, 31.84, 34.15, 38.79, 39.58, 44.50, 47.19, 56.77, 60.46, 119.20, 128.44, 130.02, 130.02, 131.34, 131.35, 134.96, 137.13, 139.14, 158.62, 170.08, 179.07; HRMS (FAB, m/z) calcd. for $C_{21}H_{28}N_5O_4S$ ($M^+ + 1$) 446.1862, observed 446.1862.

Reaction of scaffold 14a2 with L-leucine methyl ester isocyanate following the previously described general procedures gave trityl-protected GGTI-2415 as a colorless oil in 80% yield: $^1H$ NMR ($CDCl_3$, 500 MHz) δ 0.81 (d, J=6.5 Hz, 3H), 0.82 (d, J=6.5 Hz, 3H), 1.02 (m, 1H), 1.26 (m, 2H), 2.83 (ddd, J=14.0, 11.0, 4.0 Hz, 1H), 3.01 (dd, J=13.5, 9.0 Hz, 1H), 3.12 (dt, J=12.2, 3.0 Hz, 1H), 3.31 (dd, J=13.5, 3.8 Hz, 1H), 3.40 (ddd, J=11.7, 11.7, 4.0 Hz, 1H), 3.64 (s, 3H), 4.03 (m, 2H), 4.21 (dt, J=8.3, 5.2 Hz, 1H), 4.31 (d, J=14.5 Hz, 1H), 4.41 (brs, 1H), 4.65 (d, J=14.5 Hz, 1H), 6.78 (s, 1H), 7.05-

7.34 (m, 20H), 7.36 (s, 1H); HRMS (FAB, m/z) calcd. for $C_{43}H_{46}N_5O_4$ ($M^+$+1) 684.3550, observed 684.3552.

Deprotection of the above compound following the general procedure described previously afforded GGTI-2415 as a colorless oil in 88% yield: $^1$H NMR (CDCl$_3$, 500 MHz) δ 0.83 (d, J=6.5 Hz, 3H), 0.84 (d, J=6.5 Hz, 3H), 1.20 (m, 1H), 1.36 (m, 2H), 2.97 (m, 1H), 3.10 (m, 2H), 3.25 (dt, J=13.5, 3.5 Hz, 1H), 3.45 (m, 1H), 3.64 (s, 3H), 4.10 (brd, J=12.0 Hz, 1H), 4.21 (m, 1H), 4.46 (d, J=15.5 Hz, 1H), 4.73 (m, 2H), 4.90 (brs, 1H), 7.10-7.34 (m, 6H), 8.67 (s, 1H); $^{13}$C NMR (CDCl$_3$, 125 MHz) δ 22.13, 23.04, 24.94, 37.72, 37.88, 41.48, 41.56, 47.09, 52.49, 52.60, 60.20, 118.52, 127.62, 129.20, 129.21, 129.26, 129.94, 129.95, 134.61, 137.49, 156.76, 168.83, 174.86; HRMS (FAB, m/z) calcd. for $C_{23}H_{32}N_5O_4$ ($M^+$+1) 442.2454, observed 442.2455.

Saponification of GGTI-2415 following the general procedure described previously afforded GGTI-2416 as a colorless oil in 85% yield: $^1$H NMR (MeOH, 500 MHz) δ 0.68 (d, J=6.0 Hz, 3H), 0.69 (d, J=6.0 Hz, 3H), 1.23 (m, 1H), 1.31 (m, 2H), 2.61 (ddd, J=14.0, 10.5, 3.8 Hz, 1H), 2.76 (dt, J=12.3, 3.2 Hz, 1H), 3.03-3.13 (m, 3H), 3.66 (brd, J=13.5 Hz, 1H), 3.96 (dd, J=9.8, 4.4 Hz, 1H), 4.25 (d, J=15.0 Hz, 1H), 4.43 (d, J=15.0 Hz, 1H), 4.61 (t, J=5.5 Hz, 1H), 6.84 (s, 1H), 6.95-7.03 (m, 5H), 7.51 (s, 1H); $^{13}$C NMR (CDCl$_3$, 125 MHz) δ 22.57, 24.12, 26.39, 38.80, 39.68, 43.30, 44.51, 47.16, 55.87, 60.34, 119.12, 128.36, 129.98, 129.99, 131.36, 131.36, 135.00, 137.15, 139.14, 158.87, 170.14, 180.67; HRMS (FAB, m/z) calcd. for $C_{22}H_{30}N_5O_4$ ($M^+$+1) 428.2298, observed 428.2297.

Syntheses of GGTI-2395 and GGTI-2396

To a stirred solution of compound 12a (450 mg, 1.4 mmol) in 5 mL anhydrous THF was added 60% NaH (56 mg, 1.4 mmol) at 0° C. The solution was stirred at rt for 0.5 h. Then 4-chloroallyl-1-tritylimidazole$^{22}$ (10, 540 mg, 1.4 mmol, prepared as set forth in Scheme 2, FIG. 2) was added, and the solution was stirred at 60° C. for 2 h. Then the reaction mixture was cooled to room temperature and the solvent was removed under reduced pressure. The residue obtained was subjected to silica gel column chromatography using hexanes/EtOAc (3:1-1:1) to afford compound 13a3 as a colorless oil (200 mg, 21%): $^1$H NMR (MeOH, 500 MHz) δ 2.80 (m, 2H), 4.08 (m, 2H), 4.48 (d, J=12.0 Hz, 0.5H), 4.78 (m, 0.5H), 4.84 (m, 0.5H), 4.85 (d, J=12.0 Hz, 0.5H), 4.93 (d, J=12.0 Hz, 0.5H), 5.04 (d, J=12.0 Hz, 0.5 H), 5.49 (d, J=6.0 Hz, 0.5H), 5.73 (d, J=6.0 Hz, 0.5H), 6.05 (m, 1H), 6.16 (d, J=6.0 Hz, 0.5H), 6.27 (m, 1.5H), 6.86 (s, 0.5H), 6.87 (s, 0.5H), 6.90-7.32 (m, 25H), 7.41 (s, 1H); HRMS (FAB, m/z) calcd. for $C_{44}H_{39}N_4O_3$ ($M^+$+1) 671.3022, observed 670.3024.

Compound 13a3 (200 mg, 0.3 mmol) was dissolved in 10 mL MeOH/EtOAc (2:1) and to the solution was added 10% Pd/C. The mixture was hydrogenated at atmospheric pressure overnight. Then the solution was filtered, and the solvent was removed to give compound 14a3 as a colorless oil (160 mg, 99%): $^1$H NMR (CDCl$_3$, 500 MHz) δ 1.81 (m, 2H), 2.47 (t, J=8.0 Hz, 2H), 2.78 (m, 2H), 2.98 (dt, J=12.3, 3.5 Hz, 1H), 3.06 (dt, J=11.6, 3.5 Hz, 1H), 3.29 (m, 2H), 3.35 (m, 1H), 3.51 (dd, J=10.0, 3.5 Hz, 1H), 6.48 (s, 1H), 7.00-7.28 (m, 20H), 7.29 (s, 1H); HRMS (FAB, m/z) calcd. for $C_{36}H_{37}N_4O$ ($M^+$+1) 541.2967, observed 541.2966.

Scaffold 14a3 was coupled to the L-leucine methyl ester isocyanate following the previously described general procedures to give trityl-protected GGTI-2395 as a colorless oil in 85% yield: $^1$H NMR (CDCl3, 500 MHz) δ 0.76 (d, J=6.0 Hz, 3H), 0.77 (d, J=6.0 Hz, 3H), 1.00 (m, 1H), 1.23 (m, 2H), 1.80 (m, 2H), 2.46 (t, J=7.5 Hz, 2H), 2.85 (m, 2H), 3.01 (dd, J=13.5, 8.5 Hz, 1H), 3.16 (ddd, J=13.5, 8.8, 6.0 Hz, 1H), 3.30 (m, 2H), 3.45 (m, 1H), 3.59 (s, 3H), 4.02 (brd, J=13.5 Hz, 1H), 4.07 (d, J=8.0 Hz, 1H), 4.18 (m, 1H), 4.36 (brs, 1H), 6.48 (s, 1H), 7.03-7.28 (m, 20H), 7.29 (s, 1H); HRMS (FAB, m/z) calcd. for $C_{44}H_{50}N_5O_4$ ($M^+$+1) 712.3863, observed 712.3861.

Deprotection of the above mentioned compound following the general procedure described previously afforded GGTI-2395 as colorless oil in 90% yield: $^1$H NMR (CDCl$_3$, 500 MHz) δ 0.77 (d, J=5.0 Hz, 3H), 0.78 (d, J=5.0 Hz, 3H), 1.12 (m, 1H), 1.29 (m, 2H), 1.82 (m, 2H), 2.61 (m, 2H), 2.89 (m, 2H), 3.03 (dd, J=13.5, 8.0 Hz, 1H), 3.26 (m, 3H), 3.40 (m, 1H), 3.59 (s, 3H), 4.04 (brd, J=13.5 Hz, 1H), 4.15 (m, 1H), 4.55 (m, 1H), 4.66 (d, J=7.5 Hz, 1H), 7.04 (s, 1H), 7.10-7.23 (m, 5H), 8.46 (s, 1H); $^{13}$C NMR (CDCl3, 125 MHz) δ 21.95, 22.14, 23.04, 24.94, 26.02, 37.82, 37.97, 41.60, 46.54, 46.62, 52.50, 52.55, 60.31, 116.06, 127.58, 129.23, 129.24, 130.03, 130.04, 133.46, 133.51, 137.74, 156.75, 168.53, 174.92; HRMS (FAB, m/z) calcd. for $C_{25}H_{36}N_5O_4$ ($M^+$+1) 470.2767, observed 470.2766.

Saponification of GGTI-2395 following the general procedure described previously afforded GGTI-2396 as a colorless oil in 85% yield: $^1$H NMR (MeOH, 500 MHz) δ 0.76 (d, J=6.5 Hz, 3H), 0.77 (d, J=6.5 Hz, 3H), 1.27 (m, 1H), 1.38 (m, 2H), 1.76 (m, 2H), 2.49 (t, J=7.5 Hz, 2H), 2.70 (ddd, J=14.0. 11.0, 4.0 Hz, 1H), 2.80 (dt, J=12.5, 3.2 Hz, 1H), 3.10 (d, J=6.0 Hz, 2H), 3.18 (m, 1H), 3.31 (m, 2H), 3.78 (brd, J=13.2 Hz, 1H), 4.03 (dd, J=10.0, 4.5 Hz, 1H), 4.60 (t, J=5.5 Hz, 1H), 6.80 (s, 1H), 7.04-7.16 (m, 5H), 7.70 (s, 1H); $^{13}$C NMR (CDCl3, 125 MHz) δ 22.56, 24.17, 24.89, 26.41, 27.76, 38.76, 39.52, 43.56, 47.61, 48.38, 56.17, 60.44, 117.89, 128.42, 130.03, 130.04, 131.35, 131.36, 136.02, 137.45, 139.21, 158.82, 170.23, 181.17; HRMS (FAB, m/z) calcd. for $C_{24}H_{34}N_5O_4$ ($M^+$+1) 456.2611, observed 456.2612.

Synthesis of GGCTI-2410 (FIG. 4, Scheme 4)

To a stirred solution of compound 12a (400 mg, 1.2 mmol) in 6 mL anhydrous THF was added 60% NaH (50 mg, 1.2 mmol) at 0° C. The solution was stirred at rt for 0.5 h. Then 4-(3-chloro-propyl)-1-tritylimidazole (480 mg, 1.2 mmol) in 4 mL anhydrous THF and catalytic amounts of Bu$_4$NI were added. The mixture was stirred at reflux for 4 h, cooled and quenched with Sat. NH$_4$Cl aqueous solution. The mixture was extracted with dichloromethane. The organic layer was washed with brine, dried over Na$_2$SO$_4$ and the solvent was removed under reduced pressure. The residue obtained was a mixture of unreacted starting materials and compound 16. The mixture was subjected to silica gel column chromatography using MeOH/CH$_2$Cl$_2$ (0.5-5%) to afford compound 16 as a colorless oil (210 mg, 30%): $^1$H NMR (CDCl$_3$, 400 MHz) δ 1.60 (m, 1H), 1.92 (m, 1H), 2.42 (t, J=7.6 Hz, 1H), 2.58 (t, J=7.6 Hz, 1H), 2.92-3.06 (m, 2H), 3.58 (m, 0.5H), 3.89 (m, 0.5H), 4.03 (m, 0.5H), 4.10 (m, 0.5H), 4.85 (t, J=7.2 Hz, 0.5H), 5.03 (t, J=7.2 Hz, 0.5H), 5.43 (dd, J=6.0, 2.8 Hz, 0.5H), 5.68 (dd, J=5.6, 3.2 Hz, 0.5H), 6.16 (d, J=6.0 Hz, 0.5H), 6.38 (d, J=6.0 Hz, 0.5H), 6.50 (s, 0.5H), 6.53 (s, 0.5H), 7.10-7.35 (m, 21H), 8.30 (d, J=4.0 Hz, 0.5H), 8.36 (d, J=4.0 Hz, 0.5H); HRMS (FAB, m/z) calcd. for $C_{37}H_{35}N_4O_3$ ($M^+$+1) 583.2709, observed 583.2710.

To a stirred solution of compound 16 (200 mg, 0.36 mmol) in 5 mL anhydrous THF was added 60% NaH (16 mg, 0.4 mmol) at 0° C. The solution was stirred at rt for 0.5 h. Then 4-chloromethyl-tritylimidazole$^{21}$ (8, 133 mg, 0.37 mmol) was added, and the solution was stirred at 60° C. for 2 h. The reaction mixture was then cooled to room temperature and the solvent was removed under reduced pressure. The residue obtained was subjected to silica gel column chromatography using hexanes/EtOAc (3:1-1:1) to afford compound 17 as a colorless oil (270 mg, 80%): $^1$H NMR (CDCl$_3$, 400 MHz) δ 1.39 (m, 1H), 1.67 (m, 1H), 2.18 (t, J=7.5 Hz, 1H), 2.35 (m, 1H), 2.50-2.68 (m, 2H), 3.28 (dt, J=10.5, 6.5 Hz, 0.5 H), 3.60 (dt, J=10.5, 6.5 Hz, 0.5 H), 3.73 (dt, J=10.5, 6.5 Hz, 0.5 H), 3.84 (dt, J=10.5, 6.5 Hz, 0.5 H), 4.22 (d, J=15.0 Hz, 0.5 H), 4.25 (d, J=15.0 Hz, 0.5 H), 4.46 (d, J=15.0 Hz, 0.5 H), 4.51 (d, J=15.0 Hz, 0.5 H), 4.60 (t, J=7.0 Hz, 0.5 H), 4.77 (t, J=7.0 Hz, 1H), 5.45 (d, J=6.0 Hz, 0.5 Hz), 5.65 (d, J=6.0 Hz, 0.5 Hz), 5.89 (d, J=6.0 Hz, 0.5 Hz), 6.12 (d, J=6.0 Hz, 0.5 Hz), 6.28 (s, 0.5 H), 6.32 (s, 0.5H), 6.56 (s, 0.5H), 6.57 (s, 0.5H), 6.78-7.20 (m, 37H), 7.28 (d, J=7.0 Hz, 1H); HRMS (FAB, m/z) calcd. for C$_{60}$H$_{53}$N$_6$O$_3$ (M$^+$+1) 905.4179, observed 905.4183.

Deprotection of compound 17 following the general procedure described previously, using 40% TFA/triethylsilane, afforded GGTI-2410 as a colorless oil in 85% yield: $^1$H NMR (CDCl$_3$, 400 MHz) δ 1.68 (m, 1H), 1.90 (m, 1H), 2.53 (t, J=7.5 Hz, 1H), 2.68 (t, J=7.5 Hz, 1H), 2.79-2.95 (m, 2H), 3.55 (dt, J=10.0, 6.0 Hz, 0.5 H), 3.86 (dt, J=10.5, 6.5 Hz, 0.5 H), 4.05 (m, 1H), 4.64-4.85 (m, 3H), 5.73 (d, J=6.0 Hz, 0.5 Hz), 5.95 (d, J=6.0 Hz, 0.5 Hz), 6.25 (d, J=6.0 Hz, 0.5 Hz), 6.36 (d, J=6.0 Hz, 0.5 Hz), 6.98-7.20 (m, 5H), 7.24 (s, 1H); 7.42 (s, 0.5H), 7.45 (s, 1H), 8.74 (s, 1H), 8.76 (s, 1H); HRMS (FAB, m/z) calcd. for C$_{22}$H$_{25}$N$_6$O$_3$ (M$^+$+1) 421.1988, observed 421.1987.

Syntheses of GGTI-2417-GGTI-2420

Alkylation of compound 12a with 4-chloromethyl-5-methlyl-1-tritylimidazole[23] (9, FIG. 2, Scheme 2) using conditions similar to that described for the synthesis of compound 13a2 (FIG. 3, Scheme 3), afforded compound 13a4 (FIG. 3, Scheme 3) as a colorless oil in 70% yield: $^1$H NMR (MeOH, 500 MHz) δ 1.40 (s, δ2.76 (m, 2H), 4.44 (m, 1.5H), 4.55 (d, J=15.0 Hz, 0.5H), 4.59 (d, J=15.0 Hz, 0.5 H), 4.77 (m, 0.5H), 4.84 (d, J=12.0 Hz, 0.5H), 4.87 (m, 0.5H), 4.93 (d, J=15.0 Hz, 0.5 H), 5.02 (d, J=15.0 Hz, 0.5 H), 5.63 (d, J=5.8 Hz, 0.5H), 5.83 (d, J=5.8 Hz, 0.5H), 6.19 (d, J=5.8 Hz, 0.5H), 6.31 (d, J=5.8 Hz, 0.5H), 6.76 (s, 1H), 6.96-7.40 (m, 21H); HRMS (FAB, m/z) calcd. for C$_{43}$H$_{39}$N$_4$O$_3$ (M$^+$+1) 659.3022, observed 659.3025.

Compound 14a4 was obtained as a colorless oil in 98% yield by hydrogenation of compound 14a3, using similar conditions described previously: $^1$H NMR (CDCl$_3$, 500 MHz) δ1.42 (s, 3H), 2.10 (br, 1H), 2.77 (m, 2H), 3.00 (dt, J=12.5, 4.0 Hz, 1H), 3.32 (m, 2H), 3.38 (dd, J=13.5, 3.2 Hz, 1H), 3.53 (dd, J=10.0, 3.3 Hz, 1H), 4.35 (d, J=14.5 Hz, 1H), 4.60 (d, J=14.5 Hz, 1H), 7.00-7.34 (m, 21H); HRMS (FAB, m/z) calcd. for C$_3$H$_{35}$N$_4$O (M$^+$+1) 527.2811, observed 527.2812.

Scaffold 14a4 was coupled to the L-leucine methyl ester isocyanate following the previously described general procedures to give trityl-protected GGTI-2417 as a colorless oil in 85% yield: $^1$H NMR (CDCl$_3$, 500 MHz) δ0.81 (d, J=6.0 Hz, 3H), 0.82 (d, J=6.0 Hz, 3H), 1.02 (m, 1H), 1.27 (m, 2H), 1.46 (s, 3H), 2.91 (ddd, J=13.5, 10.5, 3.5 Hz, 1H), 3.03 (dd, J=14.0, 8.8 Hz, 1H), 3.15 (dt, J=12.0, 3.0 Hz, 1H), 3.33 (dd, J=13.5, 3.5 Hz, 1H), 3.39 (ddd, J=11.7, 11.7, 4.0 Hz, 1H), 3.64 (s, 3H), 4.00 (brd, J=8.0 Hz, 1H), 4.04 (brd, J=13.5 Hz, 1H), 4.22 (dt, J=8.3, 5.0 Hz, 1H), 4.41 (d, J=14.5 Hz, 1H), 4.42 (brs, 1H), 4.58 (d, J=14.5 Hz, 1H), 7.06-7.35 (m, 21H); HRMS (FAB, m/z) calcd. for C$_{43}$H$_{48}$N$_5$O$_4$ (M$^+$+1) 698.3706, observed 698.3706.

Deprotection of the above mentioned compound following the general procedure described previously afforded GGTI-2417 as a colorless oil in 88% yield: $^1$H NMR (CDCl$_3$, 500 MHz) δ0.81 (d, J=6.0 Hz, 3H), 0.82 (d, J=6.0 Hz, 3H), 1.10 (m, 1H), 1.30 (m, 2H), 2.36 (s, 3H), 3.06 (m, 2H), 3.28 (dd, J=13.5, 3.8 Hz, 1H), 3.45 (ddd, J=12.0, 12.0, 4.5 Hz, 1H), 3.63 (s, 3H), 4.08 (brd, J=13.5 Hz, 1H), 4.20 (m, 1H), 4.54 (m, 4H), 7.13-7.25 (m, 5H), 8.43 (s, 1H); $^{13}$C NMR (CDCl$_3$, 125 MHz) δ9.51, 22.19, 23.01, 24.87, 37.71, 37.91, 40.45, 41.78, 47.03, 52.46, 52.50, 60.69, 124.65, 127.63, 128.66, 129.29, 129.29, 129.92, 129.92, 132.83, 137.67, 156.75, 168.51, 174.65; HRMS (FAB, m/z) calcd. for C$_{24}$H$_{34}$N$_5$O$_4$ (M$^+$+1) 456.2611, observed 456.2612.

Saponification of GGTI-2417 following the general procedure described previously afforded GGTI-2418 as a colorless oil in 85% yield: $^1$H NMR (MeOH, 500 MHz) δ0.68 (d, J=6.0 Hz, 3H), 0.70 (d, J=6.0 Hz, 3H), 1.21 (m, 1H), 1.31 (m, 2H), 2.08 (s, 3H), 2.66 (ddd, J=13.5, 10.0, 3.7 Hz, 1H), 2.75 (dd, J=12.3, 3.2 Hz, 1H), 3.00-3.15 (m, 3H), 3.66 (brd, J=13.5 Hz, 1H), 3.95 (dd, J=10.0, 4.5 Hz, 1H), 4.28 (d, J=14.8 Hz, 2H), 4.38 (d, J=14.8 Hz, 1H), 4.60 (t, J=5.5 Hz, 1H), 6.95-7.04 (m, 5H), 7.42 (s, 1H); $^{13}$C NMR (MeOH, 125 MHz) δ10.40, 22.64, 24.16, 26.38, 38.85, 39.58, 42.96, 43.64, 46.87, 56.16, 60.39, 128.32, 129.15, 129.68, 129.96, 129.96, 131.29, 131.30, 135.45, 139.16, 158.79, 169.98, 181.11; HRMS (FAB, m/z) calcd. for C$_{23}$H$_{32}$N$_5$O$_4$ (M$^+$+1) 442.2454, observed 442.2455.

Scaffold 14a4 was coupled to the L-methionine methyl ester isocyanate following the previously described general procedures to give trityl-protected GGTI-2419 as a colorless oil in 86% yield: $^1$H NMR (CDCl$_3$, 500 MHz) δ 1.42 (s, 3H), 1.48 (m, 1H), 1.75 (m, 1H), 1.99 (s, 1H), 2.14 (m, 2H), 2.90 (ddd, J=14.5, 11.0, 3.2 Hz, 1H), 2.99 (dd, J=13.5, 9.0 Hz, 1H), 3.15 (brd, J=12.0 Hz, 1H), 3.30 (dd, J=13.5, 3.5 Hz, 1H), 3.36 (dt, J=12.0, 12.0, 4.0 Hz, 1H), 3.62 (s, 3H), 4.00 (brd, J=13.0 Hz, 1H), 4.20-4.34 (m, 1H), 4.38 (d, J=14.5 Hz, 1H), 4.40-4.42 (m, 2H), 4.54 (d, J=14.5 Hz, 1H), 7.00-7.35 (m, 21H); HRMS (FAB, m/z) calcd. for C$_{42}$H$_{46}$N$_5$O$_4$S (M$^+$+1) 716.3270, observed 716.3269.

Deprotection of the above mentioned compound following the general procedure described previously afforded GGTI-2419 as a colorless oil in 88% yield: $^1$H NMR (CDCl$_3$, 500 MHz) δ1.62 (m, 1H), 1.79 (m, 1H), 2.06 (s, 3H), 2.24 (t, J=7.2 Hz, 2H), 2.40 (s, 3H), 3.12 (m, 3H), 3.31 (brd, J=12.0 Hz, 1H), 3.48 (m, 1H), 3.68 (s, 3H), 4.11 (brd, J=12.0 Hz, 1H), 4.33 (dd, J=12.5, 7.2 Hz, 1H), 4.59 (brs, 2H), 4.63 (m, 1H), 4.88 (brs, 1H), 7.15-7.35 (m, 5H), 8.46 (s, 1H); $^{13}$C NMR (CDCl$_3$, 125 MHz) δ 9.53, 15.70, 30.36, 31.92, 37.80, 37.91, 40.42, 47.00, 52.72, 53.27, 60.58, 124.67, 127.73, 128.70, 129.29, 129.30, 129.93, 129.94, 132.78, 137.65, 156.58, 168.40, 173.46; HRMS (FAB, m/z) calcd. for C$_{23}$H$_{32}$N$_5$O$_4$S (M$^+$+1) 474.2175, observed 474.2173.

Saponification of GGTI-2419 following the general procedure described previously afforded GGTI-2420 as a colorless oil in 85% yield: $^1$H NMR (MeOH, 500 MHz) δ1.62 (m, 1H), 1.82 (m, 1H), 1.89 (s, 3H), 2.12 (s, 3H), 2.15 (t, J=7.0 Hz, 2H), 2.78 (m, 2H), 3.06-3.18 (m, 3H), 3.72 (brd, J=12.0 Hz, 1H), 3.98 (dd, J=8.0, 4.8 Hz, 1H), 4.34 (d J=14.8 Hz, 1H), 4.42 (d J=14.8 Hz, 1H), 4.61 (t, J=5.6 Hz, 1H), 7.00-7.10 (m, 5H), 7.47 (s, 1H); $^{13}$C NMR (MeOH, 125 MHz) δ10.36, 15.74, 31.83, 34.36, 38.84, 39.46, 42.94, 46.91, 57.05, 60.52, 128.42, 129.14, 129.63, 130.00, 130.01, 131.28, 131.29, 135.45, 138.15, 158.57, 169.94, 179.46; HRMS (FAB, m/z) calcd. for C$_{22}$H$_{30}$N$_5$O$_4$S (M$^+$+1) 460.2019, observed 460.2019.

Syntheses of GGTI-2399-GGTI-2406

Scaffold 14a4 was coupled to the D-leucine methyl ester isocyanate following the previously described general procedures to give trityl-protected GGTI-2399 as a colorless oil in 85% yield: $^1$H NMR (MeOH, 500 MHz) δ 0.81 (d, J=6.2 Hz, 3H), 0.85 (d, J=6.2 Hz, 3H), 1.39 (s, 3H), 1.40-1.60 (m, 3H), 2.55 (m, 1H), 2.86 (brd, J=12.0 Hz, 1H), 3.17 (m, 3H), 3.59 (s, 3H), 3.68 (brd, J=13.0 Hz, 1H), 4.23 (m, 1H), 4.40 (m, 2H), 4.67 (m, 1H), 6.30 (brs, 1H), 7.00-7.14 (m, 11H), 7.16 (s, 1H), 7.25-7.36 (m, 9H); HRMS (FAB, m/z) calcd. for $C_{43}H_{49}N_5O_4$ (M$^+$+1) 498.3706, observed 498.3706.

Deprotection of the above mentioned compound following the general procedure described previously afforded CGTI-2399 as a colorless oil in 88% yield: $^1$H NMR (MeOH, 500 MHz) δ 0.84 (d, J=6.2 Hz, 3H), 0.88 (d, J=6.2 Hz, 3H), 1.50 (m, 3H), 2.32 (s, 3H), 2.76 (m, 1H), 2.86 (dt, J=11.5, 4.5 Hz, 1H), 3.21 (m, 1H), 3.39 (m, 2H), 3.63 (s, 3H), 3.78 (brd, J=14.0 Hz, 1H), 4.24 (dd, J=10.0, 5.0 Hz, 1H), 4.55 (m, 2H), 4.77 (m, 1H), 7.02-7.20 (m, 5H), 8.72 (s, 1H); HRMS (FAB, m/z) calcd. for $C_{24}H_{34}N_5O_4$ (M$^+$+1) 456.2611, observed 456.2612.

Saponification of GGTI-2399 following the general procedure described previously afforded GGTI-2400 as a colorless oil in 85% yield: $^1$H NMR (MeOH, 500 MHz) δ 0.82 (d, J=4.5 Hz, 3H), 0.84 (d, J=4.5 Hz, 3H), 1.50 (m, 3H), 2.16 (s, 3H), 2.61 (ddd, J=13.5, 10.0, 4.0 Hz, 1H), 2.73 (dt, J=12.5, 4.0 Hz, 1H), 3.17 (m, 2H), 3.20 (m, 1H), 3.56 (dt, J=13.5, 4.0 Hz, 1H), 4.13 (dd, J=10.0, 4.5 Hz, 1H), 4.34 (d, J=14.5 Hz, 1H), 4.46 (d, J=14.5 Hz, 1H), 4.71 (t, J=5.5 Hz, 1H), 6.98-7.07 (m, 5H), 7.44 (s, 1H); HRMS (FAB, m/z) calcd. for $C_{23}H_{32}N_5O_4$ (M$^+$+1) 442.2454, observed 442.2455.

Scaffold 14a4 was coupled to the L-valine methyl ester isocyanate following the previously described general procedures to give trityl-protected GGTI-2401 as a colorless oil in 80% yield: $^1$H NMR (MeOH, 500 MHz) δ 0.76 (d, J=7.0 Hz, 6H), 1.39 (s, 3H), 1.89 (m, 1H), 2.75 (ddd, J=14.0, 10.5, 4.0, 1H), 2.89 (dt, J=12.5, 3.5 Hz, 1H), 3.09-3.20 (m, 3H), 3.59 (s, 3H), 3.76 (brd, J=14.0 Hz, 1H), 3.92 (m, 1H), 4.41 (brs, 2H), 4.68 (t, J=5.6 Hz, 1H), 5.94 (brs, 1H), 7.00-7.18 (m, 1H), 7.20 (s, 1H), 7.26-7.40 (m, 9H); HRMS (FAB, m/z) calcd. for $C_{42}H_{46}N_5O_4$ (M$^+$+1) 484.3550, observed 484.3552.

Deprotection of the above mentioned compound following the general procedure described previously afforded GGTI-2401 as a colorless oil in 88% yield: $^1$H NM R (MeOH, 500 MHz) δ 0.74 (d, J=7.0 Hz, 6H), 1.85 (m, 1H), 2.27 (s, 3H), 2.85 (ddd, J=14.0, 10.5, 3.5, 1H), 2.93 (dt, J=12.0, 3.5 Hz, 1H), 3.11 (m, 2H), 3.30 (ddd, J=12.0, 11.0, 4.5 Hz, 1H), 3.59 (s, 3H), 3.80 (brd, J=14.0 Hz, 1H), 3.86 (d, J=7.2 Hz, 1H), 4.48 (d, J=15.8, 1H), 4.52 (d, J=15.8, 1H), 4.70 (t, J=5.7 Hz, 1H), 7.00-7.05 (m, 2H), 7.08-7.13 (m, 3H), 8.65 (s, 1H); HRMS (FAB, m/z) calcd. for $C_{23}H_{32}N_5O_4$ (M$^+$+1) 442.2454, observed 442.2455.

Saponification of GGTI-2401 following the general procedure described previously afforded GGTI-2402 as a colorless oil in 85% yield: $^1$H NMR (MeOH, 500 MHz) δ0.67 (d, J=7.0 Hz, 3H), 0.72 (d, J=6.6 Hz, 3H), 1.90 (m, 1H), 2.15 (s, 3H), 2.80 (m, 2H), 3.13 (d, J=5.7 Hz, 2H), 3.17 (m, 1H), 3.59 (s, 3H), 3.80 (brd, J=14.0 Hz, 1H), 3.86 (d, J=7.2 Hz, 1H), 4.48 (d, J=15.8, 1H), 4.52 (d, J=15.8, 1H), 4.70 (t, J=5.7 Hz, 1H), 7.00-7.05 (m, 2H), 7.08-7.13 (m, 3H), 7.49 (s, 1H); HRMS (FAB, m/z) calcd. for $C_{22}H_{29}N_5O_4$ (M$^+$+1) 428.2298, observed 428.2297.

Scaffold 14a4 was coupled to the L-phenylalanine methyl ester isocyanate following the previously described general procedures to give trityl-protected GGTI-2403 as a colorless oil in 85% yield: $^1$H NMR (MeOH, 500 MHz) δ 1.36 (s, 3H), 2.42 (m, 1H), 2.78 (m, 2H), 2.90 (dd, J=13.5, 5.5 Hz, 1H), 3.07 (m, 3H), 3.56 (m, 1H), 3.60 (s, 3H), 4.36 (m, 2H), 4.40 (m, 1H), 4.61 (t, J=5.2 Hz, 1H), 6.87 (brs, 1H), 7.00-7.40 (m, 25H); HRMS (FAB, m/z) calcd. for $C_{46}H_{46}N_5O_4$ (M$^+$+1) 732.3550, observed 732.3547.

Deprotection of the above mentioned compound following the general procedure described previously afforded GGTI-2403 as a colorless oil in 86% yield: $^1$H NMR (MeOH, 500 MHz) δ 2.26 (s, 3H), 2.53 (m, 1H), 2.79 (m, 2H), 2.92 (dd, J=13.5, 5.0 Hz, 1H), 3.09 (m, 3H), 3.59 (s, 3H), 3.64 (m, 1H), 4.37 (dd, J=10.2, 5.5 Hz, 1H), 4.47 (brs, 2H), 4.65 (t, J=5.2 Hz, 1H), 6.84 (brs, 1H), 7.01-7.22 (m, 10H), 8.69 (s, 1H); HRMS (FAB, m/z) calcd. for $C_{27}H_{32}N_5O_4$ (M$^+$+1) 490.2454, observed 490.2456.

Saponification of GGTI-2403 following the general procedure described previously afforded GGTI-2404 as a colorless oil in 85% yield: $^1$H NMR (MeOH, 500 MHz) δ 2.14 (s, 3H), 2.40 (m, 1H), 2.67 (dt, J=12.5, 3.7 Hz, 1H), 2.84 (dd, J=13.5, 8.0 Hz, 1H), 2.89 (m, 1H), 2.99 (ddd, J=12.5, 10.0, 4.5 Hz, 1H), 3.09 (m, 2H), 3.44 (brd, J=13.0 Hz, 1H), 4.33 (m, 1H), 4.37 (m, 2H), 4.64 (t, J=5.0 Hz, 1H), 6.84 (brs, 1H), 6.98-7.20 (m, 10H), 7.46 (s, 1H); $^{13}$C NMR (MeOH, 125 MHz) 8, 10.40, 38.65, 39.92, 40.10, 42.91, 46.74, 58.78, 59.50, 127.74, 128.23, 129.60, 129.61, 129.70, 129.77, 129.78, 130.97, 130.98, 131.30, 131.31, 135.42, 138.82, 140.34, 145.83, 158.30, 169.93, 179.61; HRMS (FAB, m/z) calcd. for $C_{26}H_{30}N_5O_4$ (M$^+$+1) 476.2298, observed 476.2298.

Scaffold 14a4 was coupled to the α-cyclohexyl-L-alanine methyl ester isocyanate following the previously described general procedures to give trityl-protected GGTI-2405 as colorless oil in 87% yield: $^1$H NMR (MeOH, 500 MHz) δ 0.79 (m, 1H), 0.87 (m, 1H), 1.11 (m, 2H), 1.19 (m, 2H), 1.40 (s, 3H), 1.45 (m, 2H), 1.61 (m, 4H), 2.63 (ddd, J=14.0, 10.8, 3.5 Hz, 1H), 2.85 (dt, J=12.1, 3.5 Hz, 1H), 3.09 (dd, J=13.5, 5.0 Hz, 1H), 3.16 (m, 2H), 3.59 (s, 3H), 3.72 (brd, J=14.0 Hz, 1H), 4.18 (m, 1H), 4.41 (brs, 2H), 4.70 (t, J=5.5 Hz, 1H), 6.31 (brs, 1H), 7.00-7.19 (m, 1H), 7.21 (s, 1H), 7.23-7.39 (m, 9H); HRMS (FAB, m/z) calcd. for $C_{46}H_{52}N_5O_4$ (M$^+$+1) 738.4019, observed 738.4021.

Deprotection of the above mentioned compound following the general procedure described previously afforded GGTI-2405 as a colorless oil in 89% yield: $^1$H NMR (MeOH, 500 MHz) δ 0.78 (m, 1H), 0.86 (m, 1H), 1.10 (m, 2H), 1.17 (m, 2H), 1.43 (m, 2H), 1.60 (m, 4H), 2.27 (s, 3H), 2.72 (ddd, J=14.0, 10.5, 3.5 Hz, 1H), 2.88 (dt, J=12.0, 3.5 Hz, 1H), 3.13 (m, 2H), 3.28 (ddd, J=12.5, 10.5, 4.0 Hz, 1H), 3.58 (s, 3H), 3.76 (brd, J=14.0 Hz, 1H), 4.14 (dd, J=10.0, 5.5 Hz, 1H), 4.48 (d, J=15.5 Hz, 1H), 4.52 (d, J=15.5 Hz, 1H), 4.71 (t, J=5.2 Hz, 1H), 6.98-7.22 (m, 5H), 8.68 (s, 1H); HRMS (FAB, m/z) calcd. for $C_{27}H_{38}N_5O_4$ (M$^+$+1) 496.2924, observed 496.2922.

Saponification of GGTI-2405 following the general procedure described previously afforded GGTI-2406 as a colorless oil in 85% yield: $^1$H NMR (MeOH, 500 MHz) δ 0.78 (m, 2H), 1.05 (m, 2H), 1.13 (m, 2H), 1.27 (m, 1H), 1.43 (m, 1H), 1.56 (m, 3H), 1.69 (m I H), 2.14 (s, 3H), 2.64 (ddd, J=14.0, 10.5, 3.5 Hz, 1H), 2.78 (m, 2H), 3.09-3.16 (m, 3H), 3.68 (brd, J=14.0 Hz, 1H), 4.07 (dd, J=10.0, 4.5 Hz, 1H), 4.35 (d, J=15.0 Hz, 1H), 4.42 (d, J=15.0 Hz, 1H), 4.66 (t, J=5.0 Hz, 1H), 7.00-7.06 (m, 5H), 7.46 (s, 1H); $^{13}$C NMR (MeOH, 125 MHz) δ 10.37, 27.71, 27.87, 28.11, 33.93, 35.47, 35.94, 38.82, 39.71, 41.99, 42.92, 46.93, 55.41, 60.28, 128.41, 129.07, 129.61, 129.96, 129.97, 131.32, 131.32, 135.43, 139.10, 158.80, 169.96, 181.28; HRMS (FAB, m/z) calcd. for $C_{26}H_{36}N_5O_4$ (M$^+$+1) 482.2767, observed 482.2766.

Syntheses of GGTI-2398 and GGTI-2407

Scaffold 14a4 was coupled to commercial available tert-butyl isocyanate following the previously described general procedures to give trityl-protected GGTI-2398 as a colorless oil in 90% yield: $^1$H NMR (MeOH, 500 MHz) δ 1.02 (s, 9H), 1.39 (s, 3H), 2.88 (dd, J=14.0, 11.0, 3.5 Hz, 1H), 2.97 (m, 1H), 2.99 (dd, J=13.5, 8.5 Hz, 1H), 3.13 (dd, J=13.5, 4.5 Hz, 1H), 3.18 (m, 1H), 3.84 (brd, J=14.0 Hz, 1H), 4.40 (d, J=14.8 Hz, 1H), 4.45 (d, J=14.8 Hz, 1H), 4.49 (dd, J=8.5, 4.0 Hz, 1H), 7.00-7.32 (m, 21H); HRMS (FAB, m/z) calcd. for $C_{40}H_{44}N_5O_2$ ($M^+$+1) 626.3495, observed 626.3492.

Deprotection of the above mentioned compound following the general procedure described previously afforded GGTI-2398 as a colorless oil in 88% yield: $^1$H NMR (MeOH, 500 MHz) δ 1.25 (s, 9H), 2.54 (s, 3H), 2.88 (ddd, J=14.5, 11.0, 4.5 Hz, 1H), 3.27 (m, 2H), 3.40 (dd, J=13.5, 3.8 Hz, 1H), 3.58 (ddd, J=11.6, 10.8, 4.2 Hz, 1H), 4.13 (brd, J=14.0 Hz, 1H), 4.78 (brs, 2H), 4.79 (m, 1H), 7.32-7.44 (m, 5H), 8.91 (s, 1H); HRMS (FAB, m/z) calcd. for $C_{21}H_{30}N_5O_2$ ($M^+$+1) 384.2400, observed 384.2401.

Scaffold 14a4 was coupled to commercial available p-tolyl isocyanate following the previously described general procedures to give trityl-protected GGTI-2407 as colorless oil in 90% yield: $^1$H NMR (MeOH, 500 MHz) δ 1.40 (s, 3H), 2.17 (s, 3H), 2.90 (ddd, J=14.5, 10.0, 3.2 Hz, 1H), 2.98 (dd, J=12.0, 3.2 Hz, 1H), 3.15 (d, J=5.5 Hz, 2H), 3.26 (m, 2H), 3.90 (brd, J=13.0 Hz, 1H), 4.40 (d, J=14.5 Hz, 1H), 4.48 (d, J=14.5 Hz, 1H), 6.90-7.40 (m, 21H); HRMS (FAB, m/z) calcd. for $C_{43}H_{42}N_5O_2$ ($M^+$+1) 660.3339, observed 660.3342.

Deprotection of the above mentioned compound following the general procedure described previously afforded GGTI-2407 as colorless oil in 88% yield: $^1$H NMR (MeOH, 400 MHz) δ 2.16 (s, 3H), 2.29 (s, 3H), 3.01 (m, 2H), 3.17 (m, 2H), 3.38 (ddd, J=12.0, 12.0, 4.0 Hz, 1H), 3.94 (brd, J=13.0 Hz, 1H), 4.54 (m, 2H), 4.84 (m, 2H), 6.92 (m, 4H), 7.10 (m, 5H), 8.66 (s, 1H); HRMS (FAB, 171/z) calcd. for $C_{24}H_{28}N_5O_2$ ($M^+$+1) 418.2243, observed 418.2242.

Syntheses of GGTI-2429-GGTI-2434

Compounds 11b-11d were synthesized using conditions similar to that described for the synthesis of compound 11a, and were purified using the same chromatographic condition. Using Cbz-α-(1-naphthyl)-L-alanine, compound 11b was obtained as a white solid in 80% yield: m.p. 131-132° C.; $^1$H NMR (CDCl$_3$, 500 MHz) δ 3.10 (s, 3H), 3.15 (s, 3H), 3.39 (m, 1H), 3.61 (m, 1H), 3.82 (t, J=5.5 Hz, 1H), 4.50 (m, 1H), 5.10 (brs, 2H), 5.28 (m, 1H), 5.59 (m, 1H), 7.28-7.38 (m, 7H), 7.48 (t, J=7.5 Hz, 1H), 7.54 (t, J=7.5 Hz, 1H), 7.75 (d, J=8.0 Hz, 1H), 7.84 (d, J=8.0 Hz, 1H), 8.21 (d, J=8.5 Hz, 1H); HRMS (FAB, m/z) calcd. for $C_{25}H_{29}N_2O_5$ ($M^+$+1) 437.2076, observed 437.2075.

Using Cbz-p-fluoro-L-phenylalaine, compound 11c was obtained as a white solid in 95% yield: m.p. 118-119° C.; $^1$H NMR (CDCl$_3$, 500 MHz) δ 3.01 (m, 2H), 3.28 (s, 1H), 3.29 (s, 1H), 4.19 (t, J=5.0 Hz, 1H), 4.33 (m, 1H), 5.07 (brs, 2H), 5.29 (m, 1H), 5.78 (m, 1H), 6.95 (t, J=8.7 Hz, 2H), 7.13 (m, 2H), 7.28-7.36 (m, 5H); HRMS (FAB, m/z) calcd. for $C_{21}H_{26}N_2O_5F$ ($M^+$+1) 405.1826, observed 405.1825.

Using Cbz-D-phenylalanine, compound 11d was obtained as a white solid in 99% yield: m.p. 123-124° C.; $^1$H NMR (CDCl$_3$, 500 MHz) δ 2.99 (m, 1H), 3.09 (m, 1H), 3.26 (s, 3H), 3.27 (s, 3H), 4.16 (t, J=5.5 Hz, 1H), 4.35 (m, 1H), 5.07 (brs, 2H), 5.31 (m, 1H), 5.74 (m, 1H), 7.15-7.36 (m, 10H); HRMS (FAB, m/z) calcd. for $C_{21}H_{27}N_2O_5$ ($M^+$+1) 387.1920, observed 387.1921.

The naphthyl-derived scaffold 12b was synthesized using conditions slightly different from that described for the synthesis of compound 12a. Compound 11b (3.1 g, 7.1 mmol) was dissolved in 100 mL 70% TFA/H$_2$O and the solution was stirred at rt overnight. The solvent was removed under reduced pressure to give a yellow oil, which was dissolved in 150 mL ethyl acetate and washed with saturated NaHCO$_3$ and brine. The organic phase was dried over anhydrous Na$_2$SO$_4$, and the solvent was removed to give a mixture of the uncyclized aldehyde and the desired product. The mixture was subjected to silica gel column chromatography using hexanes/ EtOAc (2:1-1:1) as eluant to afford compound 12b as a yellowish oil (700 mg, 25%): $^1$H NMR (CDCl$_3$, 500 MHz) δ 3.23 (dd, J=14.0, 10.2 Hz, 0.6H), 3.23 (dd, J=14.0, 7.3 Hz, 0.4H), 3.56 (m, 1H), 3.82 (d, J=12.0 Hz, 0.6H), 4.72 (d, J=12.0 Hz, 0.6H), 4.97 (d, J=12.0 Hz, 0.4H), 5.03 (d, J=12.0 Hz, 0.6H), 5.08 (dd, J=9.5, 3.5 Hz, 0.6H), 5.25 (t, J=6.5 Hz, 0.4H), 5.35 (d, J=5.5 Hz, 0.2H), 5.36 (d, J=5.5 Hz, 0.2H), 5.75 (d, J=5.5 Hz, 0.3H), 5.76 (d, J=5.5 Hz, 0.3H), 6.05 (d, J=6.0 Hz, 0.41H), 6.43 (d, J=6.0 Hz, 0.6H), 6.61 (d, J=7.5 Hz, 1H), 7.10-8.15 (m, 11H); HRMS (FAB, m/z) calcd. for $C_{23}H_{21}N_2O_3$ ($M^+$+1) 373.1552, observed 373.1551.

Compounds 12c and 12d were synthesized using conditions similar to that described for the synthesis of compound 12a. Compound 12c was obtained with 85% yield as a colorless solid: $^1$H NMR (CDCl$_3$, 500 MHz) δ 2.85-3.06 (m, 2H), 4.65 (d, J=12.0 Hz, 0.5H), 4.87 (t, J=6.5 Hz, 0.5H), 4.96 (d, J=12.0 Hz, 0.5H), 5.03 (m, 1.0H), 5.14 (d, J=12.0 Hz, 0.5H), 5.40 (d, J=5.5 Hz, 0.25H), 5.41 (d, J=5.5 Hz, 0.25H), 5.64 (d, J=5.5 Hz, 0.25H), 5.65 (d, J=5.5 Hz, 0.25H), 6.16 (d, J=6.0 Hz, 0.5H), 6.37 (d, J=6.0 Hz, 0.5H), 6.83-7.40 (m, 10H); HRMS (FAB, m/z) calcd. for $C_{19}H_{18}N_2O_3F$ ($M^+$+1) 341.1301, observed 341.1302.

Compound 12d was obtained in 88% yield as a colorless solid: m.p. 141-142° C.; $^1$H NMR (CDCl$_3$, 500 MHz) δ 2.91-3.07 (m, 2H), 4.48 (d, J=12.0 Hz, 0.5H), 4.66 (t, J=6.8 Hz, 0.5H), 4.95 (d, J=12.0 Hz, 0.5 H), 5.03 (d, J=12.0 Hz, 0.5H), 5.05 (t, J=6.8 Hz, 0.5H), 5.11 (d, J=12.0 Hz, 0.5H), 5.40 (d, J=5.0 Hz, 0.25H), 5.41 (d, J=5.0 Hz, 0.25H), 5.65 (d, J=5.0 Hz, 0.25H), 5.66 (d, J=5.0 Hz, 0.25H), 6.16 (d, J=5.5 Hz, 0.5H), 6.38 (d, J=5.5 Hz, 0.5H), 7.07-7.36 (m, 10H), 7.56 (s, 1H); HRMS (FAB, m/z) calcd. for $C_{19}H_{19}N_2O_3$ ($M^+$+1) 323.1396, observed 323.1396.

Alkylation of compounds 12b-12d with 4-chloromethyl-5-methyl-1-tritylimidazole[23] (9) using conditions similar to that described for the synthesis of compound 13a2, afforded compounds 13b-13d as colorless oils with 65-70% yields.

Compound 13b $^1$H NMR (CDCl$_3$, 500 MHz) δ1.45 (s, 1.2H), 1.46 (s, 1.8H), 3.08-3.48 (m, 2H), 3.72 (d, J=12.0 Hz, 0.5H), 4.51 (d, J=14.5 Hz, 0.5H), 4.53 (m, 1H), 4.67 (d, J=12.0 Hz, 0.5H), 4.76 (d, J=14.5 Hz, 0.5H), 4.91 (d, J=12.5 Hz, 0.5H), 4.95 (d, J=12.5 Hz, 0.5H), 5.08 (m, 0.5H), 5.22 (m, 0.5H), 5.73 (d, J=6.0 Hz, 0.4H), 6.03 (d, J=6.0 Hz, 0.6H), 6.07 (d, J=6.0 Hz, 0.4H), 6.42 (d, J=6.0 Hz, 0.6H), 6.56 (d, J=7.0 Hz, 1H), 7.07-8.14 (m, 28H); HRMS (FAB, m/z) calcd. for $C_{47}H_{41}N_4O_3$ ($M^+$+1) 709.3179, observed 709.3181.

Compound 13c $^1$H NMR (CDCl$_3$, 500 MHz) δ1.44 (s, 1.51H), 1.45 (s, 1.5H), 2.75-2.92 (m, 2H), 4.46 (d, J=12.0 Hz, 0.5H), 4.48 (d, J=12.0 Hz, 0.5H), 4.58 (d, J=12.0 Hz, 0.5H), 4.64 (d, J=14.5 Hz, 0.5H), 4.73 (d, J=14.5 Hz, 0.5H), 4.85 (t, J=6.5 Hz, 0.5H), 4.91 (d, J=12.0 Hz, 0.5H), 4.98 (d, J=12.0 Hz, 0.5H), 5.00 (t, J=6.5 Hz, 0.5H), 5.10 (d, J=12.0 Hz, 0.5H), 5.76 (d, J=6.0 Hz, 0.5H), 5.91 (d, J=6.0 Hz, 0.5H), 6.14 (d, J=6.0 Hz, 0.5H), 6.34 (d, J=6.0 Hz, 0.5H), 7.04-7.35 (m, 25H); HRMS (FAB, m/z) calcd. for $C_{43}H_{38}N_4O_3F$ ($M^+$+1) 677.2928, observed 677.2928.

Compound 13d $^1$H NMR (CDCl$_3$, 500 MHz) δ0.44 (s, 1.5H), 1.48 (s, 1.5H), 2.77-2.95 (m, 2H), 4.39 (d, J=12.0 Hz, 0.5H), 4.47 (d, J=15.0 Hz, 0.5H), 4.49 (d, J=15.0 Hz, 0.5H), 4.62 (d, J=14.5 Hz, 0.5H), 4.73 (d, J=14.5 Hz, 0.5H), 4.88 (t, J=7.0 Hz, 0.5H), 5.06 (d, J=12.0 Hz, 0.5H), 4.90 (d, J=12.0 Hz, 0.5H), 4.98 (d, J=12.0 Hz, 0.5H), 5.03 (t, J=7.0 Hz, 0.5H), 5.75 (d, J=6.0 Hz, 0.5H), 5.92 (d, J=6.0 Hz, 0.5H), 6.14 (d, J=6.0 Hz, 0.5H), 6.36 (d, J=6.0 Hz, 0.5H), 7.04-7.35 (m, 26H); HRMS (FAB, m/z) calcd. for $C_{43}H_{39}N_4O_3$ ($M^+$+1) 659.3022, observed 659.3025.

Compounds 14b-14d were obtained as colorless oils in 95-99% yields by hydrogenation of compounds 13b-13d, using similar conditions described previously. Compound 14b: $^1$H NMR (CDCl$_3$, 500 MHz) δ 1.45 (s, 3H), 2.71 (m, 1H), 2.90-3.01 (m, 2H), 3.27 (dt, J=12.0, 3.5 Hz, 1H), 3.39 (m, 1H), 3.67 (dd, J=11.0, 3.0 Hz, 1H), 3.52 (dd, J=14.0, 2.5 Hz, 1H), 4.42 (d, J=14.5 Hz, 1H), 4.63 (d, J=14.5 Hz, 1H), 7.04-7.35 (m, 17H), 7.39-7.48 (m, 3H), 7.68 (d, J=7.5, 1.5 Hz, 1H), 7.78 (d, J=7.5 Hz, 1H), 8.17 (d, J=7.5 Hz, 1H); HRMS (FAB, m/z) calcd. for C$_{39}$H$_{37}$N$_4$O (M$^+$+1) 577.2967, observed 577.2968.

Compound 14c: $^1$H NMR (CDCl$_3$, 500 MHz) δ1.41 (s, 3H), 2.80 (m, 2H), 3.00 (dt, J=12.5, 4.0 Hz, 1H), 3.28-3.33 (m, 3H), 3.50 (dd, J=10.0, 3.5 Hz, 1H), 4.36 (d, J=14.5 Hz, 1H), 4.58 (d, J=14.5 Hz, 1H), 6.86-7.40 (m, 20H); HRMS (FAB, m/z) calcd. for C$_{35}$H$_{34}$N$_4$OF (M$^+$+1) 545.2717, observed 545.2717.

Compound 14d: $^1$H NMR (CDCl$_3$, 500 MHz) δ 1.41 (s, 3H), 2.42 (br, 1H), 2.76 (m, 2H), 2.98 (dt, J=12.5, 4.0 Hz, 1H), 3.29 (m, 2H), 3.38 (dd, J=13.7, 3.5 Hz, 1H), 3.52 (dd, J=10.0, 3.5 Hz, 1H), 4.33 (d, J=14.5 Hz, 1H), 4.61 (d, J=14.5 Hz, 1H), 7.04-7.26 (m, 21H); HRMS (FAB, m/z) calcd. for C$_{35}$H$_{35}$N$_4$O (M$^+$+1) 527.2811, observed 527.2812.

Scaffold 14b was coupled to L-leucine methyl ester isocyanate following the previously described general procedures to give trityl-protected GGTI-2429 as a colorless oil in 88% yield: $^1$H NMR (CDCl$_3$, 500 MHz) δ0.58 (d, J=6.0 Hz, 3H), 0.60 (d, J=6.0 Hz, 3H), 1.43 (s, 3H), 3.07-3.26 (m, 4H), 3.36 (m, 1H), 3.43 (s, 3H), 3.81 (dd, J=14.0, 7.0 Hz, 1H), 4.00 (dd, J=14.0, 3.0 Hz, 1H), 4.16 (brd, J=13.5 Hz, 1H), 4.37 (d, J=14.7 Hz, 1H), 4.55 (brd, J=9.3 Hz, 1H), 4.60 (d, J=14.7 Hz, 1H), 7.03-7.32 (m, 19H); 7.45 (t, J=7.5 Hz, 1H), 7.55 (t, J=7.5 Hz, 1H), 7.69 (d, J=8.0 Hz, 1H), 7.79 (d, J=8.0 Hz, 1H); HRMS (FAB, m/z) calcd. for C$_{47}$H$_{50}$N$_5$O$_4$ (M$^+$+1) 748.3863, observed 748.3861.

Deprotection of the above mentioned compound following the general procedure described previously afforded GGTI-2429 as a colorless oil in 88% yield: $^1$H NMR (CDCl$_3$, 500 MHz) δ 0.43 (m, 1H), 0.61 (d, J=6.5 Hz, 3H), 0.63 (d, J=6.5 Hz, 3H), 0.81 (m, 1H), 0.89 (m, 1H), 2.28 (s, 3H), 3.11 (m, 1H), 3.18-3.33 (m, 2H), 3.43 (m, 1H), 3.47 (s, 3H), 3.87 (m, 2H), 4.02 (m, 1H), 4.16 (brd, J=11.0 Hz, 1H), 4.40 (d, J=15.0 Hz, 1H), 4.53 (d, J=15.0 Hz, 1H), 4.82 (m, 1H), 7.18 (d, J=7.0 Hz, 1H), 7.29 (t, J=7.5 Hz, 1H), 7.45 (t, J=7.5 Hz, 1H), 7.51 (t, J=7.5 Hz, 1H), 7.70 (d, J=8.5 Hz, 1H), 7.79 (d, J=8.5 Hz, 1H), 8.13 (d, J=8.5 Hz, 1H), 8.31 (s, 1H); $^{13}$C NMR (CDCl$_3$, 125 MHz) δ9.23, 22.07, 22.61, 24.48, 35.12, 37.10, 40.48, 41.10, 47.06, 52.38, 54.70, 69.68, 123.34, 124.32, 126.05, 126.55, 127.38, 128.61, 128.73, 128.92, 129.53, 131.76, 132.94, 132.94, 134.27, 156.86, 168.97, 174.06; HRMS (FAB, m/z) calcd. for C$_{28}$H$_{36}$N$_5$O$_4$ (M$^+$+1) 506.2767, observed 506.2767.

Saponification of GGTI-2429 following the general procedure described previously afforded GGTI-2430 as a colorless oil in 85% yield: $^1$H NMR (MeOH, 500 MHz) δ0.61 (d, J=6.5 Hz, 3H), 0.63 (d, J=6.5 Hz, 3H), 0.80 (m, 1H), 0.89 (m, 1H), 1.12 (m, 1H), 2.15 (s, 3H), 2.89 (m, 2H), 3.16 (m, 1H), 3.40 (dd, J=14.0, 8.5 Hz, 1H), 3.78 (m, 3H), 4.40 (s, 2H), 7.16 (d, J=7.0 Hz, 1H), 7.20 (t, J=7.8 Hz, 1H), 7.36 (t, J=7.8 Hz, 1H), 7.43 (t, J=7.5 Hz, 1H), 7.60 (s, 1H), 7.63 (d, J=8.0 Hz, 1H), 7.73 (d, J=8.0 Hz, 1H), 8.12 (d, J=8.0 Hz, 1H); $^{13}$C NMR (MeOH, 125 MHz) δ 10.28, 22.49, 23.98, 25.97, 35.67, 38.89, 42.77, 43.00, 46.99, 55.62, 60.40, 125.17, 126.95, 127.26, 128.00, 129.16, 129.25, 129.25, 129.94, 130.35, 133.98, 135.22, 135.35, 135.78, 158.78, 170.10, 180.51; HRMS (FAB, m/z) calcd. for C$_{27}$H$_{34}$N$_5$O$_4$ (M$^+$+1) 492.2611, observed 492.2613.

Scaffold 14b was coupled to L-leucine methyl ester isocyanate following the previously described general procedures to give trityl-protected GGTI-2431 as colorless oil in 87% yield: $^1$H NMR (CDCl$_3$, 500 MHz) δ0.80 (d, J=6.0 Hz, 6H), 1.09 (m, 1H), 1.30 (m, 2H), 1.49 (s, 3H), 2.78 (ddd, J=13.5, 10.5, 3.5 Hz, 1H), 3.01 (dd, J=14.0, 8.5 Hz, 1H), 3.08 (dt, J=12.0, 3.0 Hz, 1H), 3.22 (dd, J=14.0, 4.0 Hz, 1H), 3.33 (ddd, J=12.5, 11.0, 4.5 Hz, 1H), 3.61 (s, 3H), 3.94 (brd, J=14.0 Hz, 1H), 4.11 (brd, J=8.0 Hz, 1H), 4.24 (m, 1H), 4.34 (d, J=14.5 Hz, 1H), 4.39 (m, 1H), 4.55 (d, J=14.5 Hz, 1H), 6.85-7.34 (m, 20H); HRMS (FAB, m/z) calcd. for C$_{43}$H$_{47}$N$_5$O$_4$F (M$^+$+1) 716.3612, observed 716.3609.

Deprotection of the above mentioned compound following the general procedure described previously afforded GGTI-2431 as a colorless oil in 85% yield: $^1$H NMR (CDCl$_3$, 500 MHz) δ0.79 (d, J=6.2 Hz, 3H), 0.82 (d, J=6.2 Hz, 3H), 1.17 (m, 1H), 1.28 (m, 1H), 1.34 (m, 1H), 2.31 (s, 3H), 3.03 (m, 2H), 3.20 (brd, J=10.0 Hz, 1H), 3.42 (m, 1H), 3.61 (s, 3H), 4.06 (brd, J=11.5 Hz, 1H), 4.18 (m, 1H), 4.47 (d, J=15.0 Hz, 1H), 4.55 (d, J=15.0 Hz, 1H), 4, 63 (brs, 1H), 4.74 (brs, 1H), 6.89 (t, J=8.0 Hz, 2H), 7.08 (dd, J=7.5, 5.5 Hz, 2H), 8.44 (s, 1H); $^{13}$C NMR (CDCl$_3$, 125 MHz) δ9.30, 22.04, 22.86, 24.96, 36.89, 37.80, 40.43, 41.63, 47.03, 52.54, 52.64, 60.07, 115.96, 116.13, 124.40, 128.69, 131.44, 131.50, 133.09, 133.15, 156.72, 161.48, 163.43, 168.77, 174.77; HRMS (FAB, m/z) calcd. for C$_{24}$H$_{33}$N$_5$O$_4$F (M$^+$+1) 474.2517, observed 474.2517.

Saponification of GGTI-2431 following the general procedure described previously afforded GGTI-2432 as a colorless oil in 85% yield: $^1$H NMR (MeOH, 500 MHz) δ0.76 (d, J=6.0 Hz, 3H), 0.78 (d, J=6.0 Hz, 3H), 1.28-1.44 (m, 3H), 2.17 (s, 3H), 2.82 (ddd, J=14.0, 10.0, 3.5 Hz, 1H), 2.90 (dt, J=12.0, 3.5 Hz, 1H), 3.10 (m, 2H), 3.21 (m, 2H), 3.78 (brd, J=13.0 Hz, 1H), 4.03 (dd, J=10.0, 4.5 Hz, 1H), 4.36 (d, J=14.8 Hz, 1H), 4.48 (d, J=14.8 Hz, 1H), 4.65 (t, J=5.5 Hz, 1H), 6.82 (t, J=8.5 Hz, 2H), 7.06 (dd, J=8.5, 5.5 Hz, 2H), 7.57 (s, 1H); $^{13}$C NMR (MeOH, 125 MHz) δ10.29, 22.45, 24.05, 26.39, 37.88, 39.58, 42.85, 43.22, 47.06, 55.77, 60.21, 116.49, 116.66, 129.14, 129.50, 132.94, 133.00, 133.00, 135.08, 135.38, 135.38, 158.85, 169.90, 180.51; HRMS (FAB, m/z) calcd. for C$_{23}$H$_{31}$N$_5$O$_4$F (M$^+$+1) 460.2360, observed 460.2359.

Scaffold 14b was coupled to L-leucine methyl ester isocyanate following the previously described general procedures to give trityl-protected GGTI-2433 as colorless oil in 87% yield: $^1$H NMR (CDCl$_3$, 500 MHz) δ 0.82 (d, J=6.5 Hz, 3H), 0.85 (d, J=6.5 Hz, 3H), 1.11 (m, 1H), 1.33 (m, 1H), 1.44 (s, 3H), 1.47 (m, 1H), 2.84 (ddd, J=13.5, 10.0, 3.0 Hz, 1H), 3.05 (dd, J=14.0, 8.5 Hz, 1H), 3.10 (dt, J=12.0, 3.0 Hz, 1H), 3.38 (m, 2H), 3.64 (s, 3H), 3.82 (brd, J=8.5 Hz, 1H), 3.98 (brd, J=14.0 Hz, 1H), 4.06 (m, 1H), 4.38 (m, 1H), 4.41 (d, J=14.5 Hz, 1H), 4.60 (d, J=14.5 Hz, 1H), 7.07-7.37 (m, 21H); HRMS (FAB, m/z) calcd. for C$_{43}$H$_{48}$N$_5$O$_4$ (M$^+$+1) 698.3706, observed 698.3706; HRMS (FAB, m/z) calcd. for C$_{43}$H$_{48}$N$_5$O$_4$ (M$^+$+1) 698.3706, observed 698.3706.

Deprotection of the above mentioned compound following the general procedure described previously afforded GGTI-2433 as a colorless oil in 86% yield: $^1$H NMR (CDCl$_3$, 500 MHz) δ0.80 (d, J=6.7 Hz, 3H), 0.83 (d, J=6.7 Hz, 3H), 1.20 (m, 1H), 1.34 (m, 1H), 1.47 (m, 1H), 2.34 (s, 3H), 2.94 (ddd, J=14.0, 10.5, 3.5 Hz, 1H), 3.05 (m, 1H), 3.30 (dd, J=13.5, 3.5 Hz, 1H), 3.44 (ddd, J=12.0, 12.0, 4.0 Hz, 1H), 3.59 (s, 3H), 3.93 (brd, J=13.0 Hz, 1H), 4.05 (m, 1H), 4.41 (m, 1H), 4.51 (m, 1H), 4.53 (s, 2H), 7.12-7.24 (m, 5H), 8.39 (s, 1H); $^{13}$C NMR (CDCl$_3$, 125 MHz) δ 9.50, 22.07, 23.12, 25.11, 38.18, 38.27, 40.41, 41.14, 46.85, 52.41, 52.88, 60.77, 124.70, 127.63, 128.70, 129.32, 129.32, 129.86, 129.86, 132.74, 137.69, 157.31, 168.46, 174.65; HRMS (FAB, m/z) calcd. for C$_{24}$H$_{34}$N$_5$O$_4$ (M$^+$+1) 456.2611, observed 456.2612.

Saponification of GGTI-2433 following the general procedure described previously afforded GGTI-2434 as a colorless oil in 85% yield: $^1$H NMR (MeOH, 500 MHz) δ0.82 (d, J=6.5 Hz, 3H), 0.83 (d, J=6.0 Hz, 3H), 1.42-1.60 (m, 3H), 2.17 (s, 3H), 2.61 (ddd, J=13.5, 10.0, 3.5 Hz, 1H), 2.75 (dd, J=12.5, 3.5 Hz, 1H), 3.15-3.26 (m, 2H), 3.57 (dt, J=13.5, 4.0 Hz, 1H), 4.12 (dd, J=10.0, 4.8 Hz, 1H), 4.35 (d, J=14.8 Hz, 1H), 4.47 (d, J=14.8 Hz, 1H), 4.71 (t, J=5.5 Hz, 1H), 6.97-7.10 (m, 5H), 7.53 (s, 1H); $^{13}$C NMR (MeOH, 125 MHz) δ10.37, 22.67, 24.15, 26.56, 38.98, 40.32, 42.81, 43.42, 46.81, 55.80, 59.52, 128.21, 129.18, 129.57, 129.76, 129.76, 131.29, 131.29, 135.39, 139.04, 158.74, 170.35, 180.53; HRMS (FAB, m/z) calcd. for $C_{23}H_{32}N_5O_4$ (M$^+$+1) 442.2454, observed 442.2455.

Synthesis of GGTI-2435 (FIG. 6, Scheme 6)

A mixture of L-leucine methyl ester hydrochloride (1.83, 10 mmol), Cbz-L-leucine (2.99 g, 10 mmol), DIEA (1.8 mL, 10 mmol), EDCI (1.92 g, 10 mmol), in 20 mL anhydrous methylene chloride was stirred at rt for 5 h. The reaction mixture was diluted with 80 mL methylene chloride, and the solution was washed with 1N HCl, saturated sodium bicarbonate solution, and brine. The organic phase was dried over sodium sulfate, and passed through a pad of silica gel, and the solid phase was washed with 1-2.5% MeOH/CH$_2$Cl$_2$. Fractions were combined and the solvent was removed to afford compound 21a (3.7 g, 87%) as a colorless oil: $^1$H NMR (CDCl$_3$, 500 MHz) δ 0.80 (d, J=6.5 Hz, 3H), 0.81 (d, J=6.5 Hz, 3H), 1.38 (m, 1H), 1.43 (m, 1H), 1.49 (m, 1H), 2.95-3.08 (m, 2H), 3.62 (s, 3H), 4.36 (m, 1H), 4.48 (m, 1H), 5.01 (d, J=14.8 Hz, 1H), 5.03 (d, J=14.8 Hz, 1H), 5.22 (brs, 1H), 6.04 (m, 1H), 7.11-7.32 (m, 10H).

To a solution of compound 21a (1 g, 2.35 mmol) in 15 mL anhydrous dichloromethane was added DIBAL-H (1.5 M in toluene) (3.2 mL, 4.8 mmol) at −78° C. The reaction was stirred at this temperature for 1 h before being quenched by adding 1 mL of methanol and 7 mL of water. After warming to rt, the reaction mixture was extracted with dichloromethane. The organic layer was separated and dried over Na$_2$SO$_4$ and concentrated to give a yellow solid, which was a mixture of unreacted methyl ester and the desired aldehyde. The mixture was subjected to silica gel column chromatography using hexanes/EtOAc (2:1) as eluant to afford aldehyde 21b (380 mg, 40%) as a colorless oil: $^1$H NMR (CDCl$_3$, 500 MHz) δ 0.88 (m, 6H), 1.24 (m, 1H), 1.31 (m, 1H), 1.42 (m, 1H), 3.06 (m, 1H), 3.14 (m, 1H), 4.43 (m, 2H), 5.11 (brs, 2H), 5.30 (m, 1H), 6.11 (m, 1H), 7.10-7.40 (m, 10H), 9.40 (s, 0.5H), 9.47 (s, 0.5H); HRMS (FAB, m/z) calcd. for $C_{23}H_{29}N_2O_4$ (M$^+$+1) 397.2127, observed 397.2127.

Compound 21b (300 mg, 0.76 mmol) was dissolved in 5 mL 70% TFA/H$_2$O, and the solution was stirred at rt for 2 h. The solvent was removed in vacuo to give a yellowish oil, which was dissolved in ethyl acetate and washed with saturated NaHCO$_3$ aqueous solution and brine. The organic phase was dried over anhydrous Na$_2$SO$_4$, and the solvent removed to give scaffold 22 (250 mg, 87%) as a colorless oil: $^1$H NMR (CDCl$_3$, 500 MHz) δ 0.86-1.00 (m, 6H), 1.68-2.08 (m, 3H), 2.89-3.10 (m, 2H), 4.51 (d, J=12.0 Hz, 0.5H), 4.90 (dd, J=9.0, 5.0 Hz, 0.5H), 4.97 (d, J=12.0 Hz, 0.5H), 5.05 (d, J=12.5 Hz, 0.5H), 5.07 (m 0.5H), 5.15 (d, J=12.5 Hz, 0.5H), 5.97 (s, 0.5H), 6.15 (s, 1H), 7.10-7.50 (m, 10H), 7.69 (brs, 1H); HRMS (FAB, m/z) calcd. for $C_{23}H_{27}N_2O_3$ (M$^+$+1) 379.2022, observed 379.2023.

Alkylation of scaffold 22 (250 mg, 0.78 mmol) with 4-chloromethyl-5-methyl-1-tritylimidazole[23] (9), using conditions similar to that described for the synthesis of compound 13a2, afforded compound 23 in 15% yield after chromatographed on silica gel column using hexanes/EtOAc (3:1-1:1) as eluant. Unreacted starting materials were recovered. Compound 23 was obtained as a colorless oil (80 mg, 15%): $^1$H NMR (CDCl$_3$, 500 MHz) δ 0.89-1.01 (m, 6H), 1.36 and 1.39 (s, 3H), 1.66 (m, 2H), 1.80 and 1.88 (dd, J=15.0, 10.0 Hz, 1H), 2.75-2.94 (m, 2H), 4.15-4.25 (m, 1.5H), 4.77-4.84 (m, 1.5H), 4.94-5.00 (m, 1H), 5.10-5.16 (m, 1H), 6.00 and 6.20 (s, 1H), 6.93-7.27 (m, 21H); HRMS (FAB, m/z) calcd. for $C_{47}H_{47}N_4O_3$ (M$^+$+1) 715.3648, observed 715.3651.

Compound 23 was hydrogenated, using conditions similar to those described previously, to generate predominantly the 6S isomer in 90% yield: $^1$H NMR (CDCl$_3$, 500 MHz) δ0.79 (d, J=6.5 Hz, 3H), 0.80 (d, J=6.5 Hz, 3H), 1.14 (m, 1H), 1.48 (s, 3H), 1.52 (m, 2H), 2.83 (m, 2H); 3.08 (dd, J=13.5, 8.0 Hz, 1H), 3.22 (dd, J=13.5, 4.0 Hz, 1H), 3.38 (m, 1H), 3.66 (dd, J=7.5, 4.0 Hz, 1H), 3.87 (d, J=15.0 Hz, 1H), 5.19 (d, J=15.0 Hz, 1H), 7.07-7.35 (m, 21H); HRMS (FAB, m/z) calcd. for $C_{39}H_{43}N_4O$ (M$^+$+1) 583.3437, observed 583.3437. Without further purification, the crude product (60 mg) was coupled to L-leucine methyl ester isocyanate following previously described general procedures. The product was purified by silica gel column chromatography using MeOH/CH$_2$Cl$_2$ (0.5%-5%) as eluant to afford compound 24 (63 mg, 80%) as a colorless oil: $^1$H NMR (CDCl$_3$, 500 MHz) δ 0.79 (d, J=6.5 Hz, 3H), 0.80 (d, J=6.5 Hz, 3H), 0.82 (d, J=6.5 Hz, 3H), 0.86 (m, 1H), 0.92 (d, J=6.5 Hz, 3H), 0.93 (m, 1H), 1.16 (m, 2H), 1.33 (s, 3H), 1.63 (m, 1H), 1.84 (m, 1H), 2.82 (m, J=13.0, 10.0 Hz, 1H), 3.04 (dd, J=14.0, 10.0 Hz, 1H), 3.42 (dd, J=14.0, 3.0 Hz, 1H), 3.46 (m, 1H), 3.49 (s, 3H), 3.88 (d, J=12.5 Hz, 1H), 4.08 (d, J=15.5 Hz, 1H), 4.19 (m, 1H), 4.28 (dd, J=14.0, 3.0 Hz, 1H), 4.37 (dd, J=10.0, 2.5 Hz, 1H), 5.37 (d, J=15.5 Hz, 1H), 7.06-7.35 (m, 21H); HRMS (FAB, m/z) calcd. for $C_{47}H_{56}N_5O_4$ (M$^+$+1) 754.4332, observed 754.4335.

Deprotection of compound 24 following the general procedure described previously afforded compound 25 as a colorless oil (35 mg, 85% yield): $^1$H NMR (CDCl$_3$, 500 MHz) δ0.78 (d, J=6.5 Hz, 3H), 0.79 (d, J=6.5 Hz, 3H), 0.84 (d, J=6.5 Hz, 3H), 0.87 (d, J=6.5 Hz, 3H), 1.06 (m, 1H), 1.15 (m 2H), 1.28 (m, 1H), 1.39 (m, 1H), 1.60 (m, 1H), 2.30 (s, 1H), 2.82 (dd, J=14.0, 10.0 Hz, 1H), 3.08 (dd, J=13.0, 10.0 Hz, 1H), 3.33 (brd, J=13.0 Hz, 1H), 3.52 (m, 1H), 3.63 (s, 3H), 4.17 (dd, J=14.0, 7.5 Hz, 1H), 4.34 (dd, J=14.0, 3.5 Hz, 1H), 4.46 (brd, J=7.5 Hz, 1H), 4.54 (brs, 2H), 4.68 (brs, 1H), 7.15-7.30 (m, 5H), 8.51 (s, 1H); $^{13}$C NMR (CDCl$_3$, 125 MHz) δ 9.56, 21.45, 22.05, 23.01, 24.39, 24.74, 24.91, 37.21, 38.25, 41.16, 41.56, 41.97, 52.32, 52.50, 55.75, 61.26, 125.25, 126.86, 127.67, 129.37, 129.37, 129.90, 129.90, 133.44, 137.61, 156.94, 168.95, 174.89; HRMS (FAB, m/z) calcd. for $C_{28}H_{42}N_5O_4$ (M$^+$+1) 512.3237, observed 512.3238.

Saponification of compound 25 following the general procedure described previously afforded GGTI-2435 as a colorless oil (27 mg, 85% yield): $^1$H NMR (MeOH, 500 MHz) δ; $^{13}$C NMR (MeOH, 125 MHz) δ 10.70, 21.58, 22.38, 24.10, 24.89, 25.91, 26.26, 38.29, 39.23, 41.36, 43.10, 43.81, 54.44, 55.54, 61.12, 128.36, 129.22, 129.85, 130.07, 130.07, 131.22, 131.22, 135.37, 139.40, 159.35, 171.70, 180.54; HRMS (FAB, m/z) calcd. for $C_{27}H_{40}N_5O_4$ (M$^+$+1) 498.3080, observed 498.3079.

Syntheses of GGTI-2376 and GGTI-2377 (FIG. 5, Scheme 5)

1,2-Dibromoethane (0.94 g, 5 mmol) and a solution of K$_2$CO$_3$ (0.7 g, 5 mmol) in 10 mL water were alternately added dropwise to a solution of L-phenylalanine (1.65 g, 10 mmol) and NaOH (0.4 g, 10 mmol) in water with stirring at 90° C. After 5 h, the reaction mixture was cooled and neutralized with concentrated HCl. The resulting precipitate was filtered off and dried under reduced pressure to give crude 18 (1 g, 4 mmol), which without further purification was refluxed with concentrated $H_2SO_4$ (0.79 g, 8 mmol) in 25 mL anhydrous methanol for 24 h to afford the piperazinone scaffold 19 as its $H_2SO_4$ salt after removal of the solvent. The solid was treated with saturated $NaHCO_3$ solution and the mixture was extracted with $CH_2Cl_2$ to afford compound 18 as a colorless oil (1.07 g, 75%): $^1H$ NMR (CDCl3, 500 MHz) δ 1.16 (t, J=7.0 Hz, 3H), 2.49 (dd, J=13.5, 9.7 Hz, 1H), 2.66 (ddd, J=13.5, 10.0, 3.5 Hz, 1H), 2.82 (m, 2H), 3.01 (dd, J=14.5, 11.0 Hz, 1H), 3.23 (m, 3H), 3.52 (dd, J=10.0, 3.5 Hz, 1H), 4.41 (m, 2H), 5.00 (dd, J=10.5, 5.5 Hz, 1H), 7.05-7.28 (m, 10H); $^{13}C$ NMR (CDCl3, 500 MHz) δ14.60, 34.69, 38.69, 42.22, 47.00, 59.00, 60.95, 61.73, 126.99, 127.19, 128.94, 128.95, 129.02 129.03, 129.29, 129.30, 129.67, 129.68, 137.51, 138.70, 170.16, 170.97; HRMS (FAB, m/z) calcd. for $C_{22}1H_{27}N_2O$ ($M^+$+1) 367.2022, observed 367.2021.

A mixture of compound 19 (146 mg, 0.4 mmol), N-1-trityl-deaminohistidine (150 mg, 0.4 mmol), EDCI (85 mg, 0.44 mmol), DIEA (0.09 mL, 0.44 mmol) in 3 mL anhydrous methylene chloride was stirred at rt for 5 h. The reaction mixture was diluted with 20 mL methylene chloride, and the solution was washed with 1N HCl, saturated sodium bicarbonate solution, and brine. The organic phase was dried over sodium sulfate and the solvent was removed on a rotovap to give an oil, which was purified by silica gel column chromatography with 2.5-5% $MeOH/CH_2Cl_2$ as eluant to afford the trityl-protected compound (20) as a colorless oil (124 mg, 85%): $^1H$ NMR (CDCl$_3$, 500 MHz) δ1.23 (t, J=7.0 Hz, 3H), 1.42 (m, 0.5H), 2.14 (m, 0.5H), 2.32 (m, 0.5H), 2.50-2.72 (m, 2.5H), 2.75-2.86 (m, 1.5H), 2.95-3.12 (m, 2.5H), 3.17 (m, 0.5H), 3.26 (dd, J=14.0, 6.5 Hz, 0.5H), 3.37 (dd, J=14.0, 6.5 Hz, 0.5H), 3.51 (brd, J=13.5 Hz, 0.5H), 4.17 (q, J=7.0 Hz, 2H), 4.40 (m, 0.5H), 4.49 (m, 0.5H), 5.11 (m, 0.5H), 5.25 (m, 0.5H), 6.28 (m, 0.5H), 6.60 (m, 0.5H), 6.90-7.40 (m, 26H); HRMS (FAB, m/z) calcd. for $C_{47}H_{47}N_4O_4$ ($M^+$+1) 731.3597, observed 731.3600.

Deprotection of the above mentioned compound following the general procedure described previously afforded GGTI-2376 as a colorless oil in 88% yield: $^1H$ NMR (MeOH, 500 MHz) δ1.23 (1, J=7.0 Hz, 3H), 1.36 (m, 0.5H), 2.33 (m, 0.5H), 2.55 (m, 3H), 2.76-3.20 (m, 8H), 3.56 (brd, J=12.5 Hz, 0.5H), 4.17 (q, J=7.0 Hz, 2H), 4.31 (m, 0.5H), 4.36 (m, 0.5H), 4.94 (m, 0.5H), 5.02 (m, 0.5H), 6.86 (s, 0.5H), 6.90 (s, 0.5H), 7.00-7.30 (m, 10H), 8.67 (s, 0.5H), 8.63 (s, 0.5H); HRMS (FAB, m/z) calcd. for $C_{28}H_{33}N_4O_4$ ($M^+$+1) 489.2502, observed 489.2502.

Saponification of GGTI-2376 following general procedure described previously afforded GGTI-2377 as a colorless oil in 85% yield: $^1H$ NMR (MeOH, 500 MHz) δ 1.33 (m, 0.5H), 2.10 (m, 0.5H), 2.26 (m, 0.5H), 2.34 (m, 0.5H), 2.47 (m, 1.5H), 2.60-2.84 (m, 3.5H), 2.92 (m, 1H), 3.07 (dt, J=13.0, 3.5 Hz, 0.5H), 3.23-3.40 (m, 3H), 3.62 (brd, J=13.2 Hz, 0.5H), 4.17 (dd, J=10.0, 3.3 Hz, 0.5H), 4.35 (brd, J=13.5 Hz, 0.5H), 4.91 (t, J=6.5 Hz, 0.5H), 5.21 (dd, J=11.3, 5.0 Hz, 0.5H), 5.26 (dd, J=12.0, 5.0 Hz, 0.5H), 6.40 (s, 0.5H), 6.63 (s, 0.5H), 6.72-7.25 (m, 10H), 7.38 (s, 0.5H), 7.45 (s, 0.5); HRMS (FAB, m/z) calcd. for $C_{26}H_{29}N_4O_4$ ($M^+$+1) 461.2189, observed 461.2187.

Syntheses of CHP343 (FIG. 7, Scheme 7)

A mixture of aminoacetaldehyde dimethyl acetal (0.55 mL, 5 mmol), Cbz-L-homophenylalanine (1.56 g, 5 mmol), EDCI (0.96 g, 5 mmol), in 10 mL anhydrous methylene chloride was stirred at rt for 5 h. The reaction mixture was diluted with 40 mL methylene chloride, and the solution was washed with 1N HCl (10 mL), saturated sodium bicarbonate solution (10 mL), and brine (10 mL). The organic phase was dried over sodium sulfate, and passed through a pad of silica gel, and the solid phase was washed with 1-2.5% MeOH/ $CH_2Cl_2$. Fractions were combined and the solvent was removed to afford compound CHP337 as colorless oil (1.75 g, 90%): HRMS (FAB, m/z) calcd. for $C_{22}H_{29}N_2O_5$ ($M^+$+1) 401.2076, observed 41.2075. Compound CHP337 (1.75 g, 4.38 mmol) was dissolved in 18 mL 70% $TFA/H_2O$ and the solution was stirred at rt for 2 h. The solvent was removed under reduced pressure to give a yellow oil, which was dissolved in 100 mL ethyl acetate and washed with saturated aqueous $NaHCO_3$ solution and brine. The organic phase was dried over anhydrous $Na_2SO_4$, and the solvent removed to give compound CHP338 as a colorless oil (1.4 g, 95%): $^1H$ NMR (CDCl$_3$, 500 MHz) δ 1.90-2.10 (m, 2H), 2.57-2.78 (m, 2H), 4.76 (t, J=6.5 Hz, 0.5H), 4.89 (t, J=7.0 Hz, 0.5H), 5.19 (d, J=12.0 Hz, 2H), 5.59 (t, J=5.0 Hz, 0.5H), 5.69 (t, J=5.0 Hz, 0.5H), 6.22 (d, J=5.5 Hz, 0.5H), 6.37 (d, J=5.5 Hz, 0.5H), 7.08-7.38 (m, 10H), 7.78 (brs, 0.5H), 7.92 (brs, 0.5H); HRMS (FAB, m/z) calcd. for $C_{20}H_{21}N_2O_3$ ($M^+$+1) 337.1552, observed 337.1551.

To a stirred solution of compound CHP338 (700 mg, 2.08 mmol) in 10 mL anhydrous THF was added 60% NaH (80 mg, 2.1 mmol) at 0° C. The solution was stirred at rt for 0.5 h. Then 4-chloromethyl-5-methyl-1-tritylimidazole (9, 1 g, 2.6 mmol) was added, and the solution was stirred at 60° C. for 2 h. The reaction mixture was then cooled to room temperature and the solvent was removed on a rotovap. The residue obtained was subjected to silica gel column chromatography using hexanes/EtOAc (3:1-1:1) to afford compound CHP339 as a colorless oil (260 mg, 18%): $^1H$ NMR (MeOH, 500 MHz) δ1.44 (s, 1.5H), 1.45 (s, 1.5H), 1.91 (m, 2H), 2.48-2.73 (m, 2H), 4.37 (d, J=15.0 Hz, 1H), 4.80 (t, J=6.5 Hz, 0.5H), 4.84 (d, J=14.5 Hz, 0.5H), 4.86 (d, J=14.5 Hz, 0.5H), 4.91 (t, J=6.5 Hz, 0.5H), 5.20 (d, J=14.0 Hz, 2H), 5.90 (d, J=6.0 Hz, 0.5H), 5.96 (d, J=6.0 Hz, 0.5H), 6.22 (d, J=6.0 Hz, 0.5H), 6.37 (d, J=6.0 Hz, 0.5H), 7.00-7.39 (m, 26H); HRMS (FAB, m/z) calcd. for $C_{44}H_{41}N_4O_3$ ($M^+$+1) 673.3179, observed 673.3178.

Compound CHP339 (250 g, 0.37 mmol) was dissolved in 10 mL MeOH, and to the solution was added catalytic amount of 10% Pd/C. The mixture was hydrogenated at atmospheric pressure overnight. Then the solution was filtered, and the solvent was removed to give compound CHP340 as a colorless oil (200 mg, 100%): $^1H$ NMR (CDCl$_3$, 500 MHz) δ 1.47 (s, 3H), 1.95 (m, 1H), 2.25 (m, 1H), 2.70 (m, 2H), 2.94 (m, 1H), 3.10 (m, 1H), 3.35-3.45 (m, 3H), 4.50 (d, J=14.5 Hz, 1H), 4.55 (d, J=14.5 Hz, 1H), 7.09-7.33 (m, 21H); HRMS (FAB, m/z) calcd. for $C_{36}H_{37}N_4O$ ($M^+$+1) 541.2967, observed 541.2966.

Reaction of scaffold CHP340 (200 mg, 0.37 mmol) with L-leucine methyl ester isocyanate following previously described general procedures gave trityl-protected CHP341 as a colorless oil (220 mg, 84%): $^1H$ NMR (CDCl$_3$, 500 MHz) δ 0.95 (d, J=6.7 Hz, 6H), 1.45 (m, 1H), 1.48 (s, 3H), 1.58 (m, 1H), 1.66 (m, 1H), 2.00 (m, 1H), 2.28 (m, 1H), 2.75 (m, 2H), 3.26 (ddd, J=13.5, 10.0, 4.0 Hz, 1H), 3.42 (dt, J=12.8, 3.8 Hz, 1H), 3.52 (m, 1H), 3.71 (s, 3H), 4.05 (dt, J=13.2, 3.5 Hz, 1H), 4.34 (d, J=14.5 Hz, 1H), 4.43 (t, J=6.8 Hz, 1H), 4.48 (m, 1H), 4.66 (d, J=7.2 Hz, 1H), 4.77 (d, J=14.5 Hz, 1H), 6.78 (s, 1H), 7.11-7.34 (m, 21H); HRMS (FAB, m/z) calcd. for $C_{44}H_{50}N_5O_4$ ($M^+$+1) 712.3863, observed 712.3861.

General Procedure for Deprotection and Hydrolysis.

Trityl-protected compound CHP341 (0.2 mmol), was dissolved in 2 mL of 40% $TFA/CH_2Cl_2$. Triethylsilane was added dropwise until the deep yellow color disappeared. The mixture was stirred at rt for 1 h. The solvent was removed and the resulting residue was dried under reduced pressure to give a yellow solid. After washing with hexanes, the residue was subjected to silica gel column chromatography using $CH_2Cl_2$ followed by 5-10% $MeOH/CH_2Cl_2$ as eluant. The fractions were combined and concentrated to afford a colorless oil. The deprotected product (0.2 mmol) was then dissolved in a 0.5 mL of MeOH, and then 1 mL of 1N NaOH. The mixture was stirred at rt for 1 h. The solvent was removed under reduced pressure, and the resulting residue was suspended in 2 mL of 30% $MeOH/CH_2Cl_2$, and the suspension was passed through a pad of silica gel. The solid phase was further eluted with 30%-50% $MeOH/CH_2Cl_2$ solution. The fractions containing the product were combined and the solvent was removed to afford the target molecules in 80-85% yields.

Deprotection of CHP341 following the general procedure described above afforded CHP342 as a colorless oil in 85% yield: $^1$H NMR ($CDCl_3$, 500 MHz) δ 0.91 (d, J=6.5 Hz, 3H), 0.92 (d, J=6.5 Hz, 3H), 1.48 (m, 1H), 1.54 (m, 1H), 1.65 (m, 1H), 1.97 (m, 1H), 2.20 (m, 1H), 2.32 (s, 3H), 2.69 (m, 2H), 3.59 (s, 3H), 3.17 (brd, 12.0 Hz, 1H), 3.23 (m, 1H), 3.36 (m, 1H), 3.68 (s, 3H), 4.08 (d, J=15.0 Hz, 1H), 4.20 (d, J=11.0 Hz, 1H), 4.41 (m, 1H), 4.62 (d, J=15.0 Hz, 1H), 4.67 (m, 1H), 5.44 (d, J=8.0 Hz, 1H), 7.12-7.28 (m, 6H), 8.54 (s, 1H); $^{13}$C NMR ($CDCl_3$, 125 MHz) 9.42, 22.16, 23.18, 25.34, 32.33, 33.88, 37.19, 39.90, 41.55, 46.75, 52.58, 52.98, 57.08, 124.27, 126.60, 128.56, 128.83, 128.84, 128.94, 128.95, 133.55, 141.19, 156.87, 169.80, 175.16; HRMS (FAB, m/z) calcd. for $C_{25}H_{36}N_5O_4$ ($M^+$+1) 470.2767, observed 470.2767.

Saponification of CHP342 following the general procedure afforded CHP343 as a colorless oil in 88% yield: $^1$H NMR (MeOH, 500 MHz) δ 0.80 (d, J=6.5 Hz, 3H), 0.82 (d, J=6.5 Hz, 1H), 1.50 (m, 2H), 1.58 (m, 1H), 1.95 (m, 1H), 2.09 (m, 1H), 2.14 (s, 3H), 2.57 (m, 2H), 3.17 (m, 1H), 3.20 (m, 1H), 3.29 (m, 2H), 3.94 (brd, J=11.0 Hz, 1H), 4.15 (dd, J=8.5, 5.5 Hz, 1H), 4.41 (d, J=15.0 Hz, 1H), 4.47 (d, J=15.0 Hz, 1H), 4.65 (dd, J=8.5, 4.5 Hz, 1H), 7.00-7.14 (m, 6H); $^{13}$C NMR (MeOH, 125 MHz) δ 10.23, 22.57, 24.17, 26.70, 33.88, 35.54, 39.39, 42.67, 43.33, 47.04, 56.15, 58.40, 127.38, 129.03, 129.05, 129.78, 129.79, 129.85, 129.86, 135.43, 143.31, 159.21, 171.02, 180.90; HRMS (FAB, m/z) calcd. for $C_{24}H_{34}N_5O_4$ ($M^+$+1) 456.2611, observed 456.2612.

Synthesis of CHP356 (Scheme 8, FIG. 8)

A mixture of L-alanine ethyl ester hydrochloride (770 mg, 5 mmol), Cbz-L-phenylalanine (1.5 g, 5 mmol), DIEA (0.85 mL, 5 mmol), EDCI (0.96 g, 5 mmol), in 10 mL anhydrous methylene chloride was stirred at rt for 5 h. The reaction mixture was diluted with 40 mL methylene chloride, and the solution was washed with 1N HCl, saturated sodium bicarbonate solution, and brine. The organic phase was dried over sodium sulfate, and passed through a pad of silica gel, and the solid phase was washed with 1-2.5% $MeOH/CH_2Cl_2$. Fractions were combined and the solvent was removed to afford compound CHP344 (1.75 g, 88%) as a white solid: m.p. 122-123° C.; $^1$H NMR ($CDCl_3$, 500 MHz) δ 1.19 (t, J=7.0 Hz, 3H), 1.26 (d, J=7.3 Hz, 3H), 2.95-3.09 (m, 2H), 4.09 (q, J=7.0 Hz, 2H), 4.36 (m, 1H), 4.40 (m, 1H), 5.02 (brs, 2H), 5.21 (brs, 1H), 6.21 (brs, 1H), 7.10-7.30 (m, 10H); HRMS (FAB, m/z) calcd. for $C_{22}H_{27}N_2O_5$ ($M^+$+1) 399.1920, observed 399.1920.

To a solution of CHP344 (800 mg, 2 mmol) in 15 mL anhydrous dichloromethane was added DIBAL-H (1.5 M in toluene) (5.5 mL, 8 mmol) at 0° C. The reaction was stirred at this temperature for 1.5 h before being quenched by adding 1 mL of methanol and 7 mL of water. After warming to rt, the reaction mixture was extracted with dichloromethane. The organic layer was separated and dried over $Na_2SO_4$ and concentrated to give a yellowish solid, which after washed with ethyl ether gave CHP345 (640 mg, 83%) as a white solid: $^1$H NMR ($CDCl_3$, 500 MHz) δ 0.98 (d, J=6.5 Hz, 3H), 1.80 (brs, 1H), 2.91 (dd, J=13.5, 8.0 Hz, 1H), 3.07 (dd, J=13.5, 6.0 Hz, 1H), 3.24 (m, 1H), 3.36 (m, 1H), 3.88 (m, 1H), 4.25 (m, 1H), 5.03 (brs, 2H), 5.30 (brs, 1H), 5.52 (brs, 1H), 7.15-7.35 (m, 10H).

To a solution of oxalyl chloride (174 μL, 2 mmol) in 4 mL dichloromethane at −78° C. was added dried DMSO (343 μL, 4 mmol) in 0.5 mL dichloromethane. After stirring for 10 min, CHP345 (640 mg, 1.8 mmol) in 3 mL dichloromethane was added slowly to the solution, stirred for 20 min, then triethylamine (1.2 mL, 9 mmol) was added, and the reaction mixture was allowed to raise to rt, and stir for 30 min. The solution was diluted with 20 mL of dichloromethane, washed with ice water and brine, dried over anhydrous $Na_2SO_4$, and the solvent was removed on a rotovap to give crude aldehyde CHP346 (510 mg, 80%) as a colorless oil. Without further purification, CHP346 (510 mg, 1.4 mmol) was dissolved in 5 mL 70% $TFA/H_2O$, and the solution was stirred at rt for 2 h. The solvent was removed in vacuo to give a yellow oil, which was dissolved in ethyl acetate and washed with saturated $NaHCO_3$ aqueous solution and brine. The organic phase was dried over anhydrous $Na_2SO_4$, and the solvent was removed to give a colorless oil which was chromatographed on silica gel using hexane/EtOAc (3:1) as eluant to afford scaffold CHP347 (410 mg, 85%) as a colorless oil: $^1$H NMR ($CDCl_3$, 500 MHz) δ 1.72 (s, 1.5H), 1.86 (s, 1.5 H), 2.90-3.10 (m, 2H), 4.52 (d, J=12.0 Hz, 0.5 H), 4.89 (m, 0.5 H), 4.98 (d, J=12.0 Hz, 0.5H), 5.06 (d, J=12.0 Hz, 0.5H), 5.07 (m, 0.5 H), 5.16 (d, J=12.0 Hz, 0.5H), 5.91 (s, 0.5 H), 6.16 (s, 0.5H), 7.12-7.42 (m, 10H), 8.52 (s, 0.5H), 8.60 (s, 0.5 H); HRMS (FAB, m/z) calcd. for $C_{20}H_{21}N_2O_3$ ($M^+$+1) 337.1552, observed 337.1551.

Alkylation of scaffold CHP347 (330 mg, 1 mmol) with 4-chloromethyl-5-methyl-1-tritylimidazole[23] (9), using conditions similar to that described for the synthesis of compound CHP339, afforded compound CHP348 after column chromatography on silica gel using hexanes/EtOAc (3:1-1:1) as eluant. Unreacted CHP347 was recovered. CHP348 was obtained as a colorless oil (60 mg, 10%). Due to the existence of several rotamers, the proton NMR spectrum is difficult to characterize, the chemical shifts of protons on two major rotamers are listed as follow: $^1$H NMR ($CDCl_3$, 500 MHz) δ 1.39 and 1.41 (s, 3H), 1.95 and 2.05 (s, 3H), 2.75-2.92 (m, 2H), 4.27-4.46 (m, 2H), 4.79-5.06 (m, 3H), 5.87 and 6.10 (s, 1H), 6.97-7.39 (m, 26H); HRMS (FAB, m/z) calcd. for $C_{44}H_{41}N_4O_3$ ($M^+$+1) 673.3179, observed 673.3178.

Compound CHP348 was hydrogenated in methanol using 10% Pd/C under atmospheric pressure overnight. The reaction solution was filtered and concentrated to give CHP349 (43 mg, 90%), which was directly coupled to L-leucine methyl ester isocyanate following previously described general procedures. The product was purified by silica gel column chromatography using $MeOH/CH_2Cl_2$ (0.5%-5%) as eluant to afford compound CHP354 (55 mg, 79%) as a colorless oil: $^1$H NMR ($CDCl_3$, 500 MHz) δ 0.75 (d, J=6.0 Hz, 3H), 0.76 (d, J=6.0 Hz, 3H), 0.77-0.91 (m, 2H), 1.13 (m, 1H), 1.18 (d, J=6.3 Hz, 3H), 1.34 (s, 3H), 2.68 (dd, J=13.5, 11.0 Hz, 1H), 3.00 (dd, J=13.0, 10.0 Hz, 1H), 3.33 (dd, J=13.5, 3.0 Hz, 1H), 3.48 (s, 3H), 3.52 (m, 1H), 3.64 (m, 1H), 3.79 (d, J=8.0 Hz, 1H), 4.00 (d, J=15.0 Hz, 1H), 4.10 (m, 1H), 4.12 (m, 1H), 4.32 (brd, J=9.0 Hz, 1H), 5.29 (d, J=15.0 Hz, 1H), 7.00-7.29 (m, 21H); FAB MS ($M^+$+1) 712.

Deprotection of compound CHP354 following the general procedure described previously afforded CHP355 as a colorless oil (30 mg, 85% yield): $^1$H NMR ($CDCl_3$, 500 MHz) δ

0.71 (d, J=7.0 Hz, 3H), 0.73 (d, J=7.0 Hz, 3H), 0.86 (m, 1H), 0.97 (m, 1H), 1.05 (d, J=6.0 Hz, 3H), 1.10 (m, 1H), 2.25 (s, 3H), 2.67 (m, 1H), 3.03 (m, 1H), 3.28 (brd, J=8.0 Hz, 1H), 3.55 (s, 3H), 3.59 (m, 1H), 4.08 (m, 1H), 4.16 (brd, J=13.0 Hz, 1H), 4.27 (brs, 1H), 4.45 (brs, 1H), 4.56 (brs, 1H), 4.61 (brs, 1H), 7.12-7.24 (m, 5H), 8.37 (s, 1H); The 6S configuration of the newly generated stereocenter was confirmed by 2D NMR experiments, including $^1H$—$^1H$ COSEY and NOSEY. An NOE was observed between axial-H-5 and one of the H-7 protons confirming the pseudoaxial orientation of the 3S benzyl group, and the axial, β orientation of H-6 (6S configuration); HRMS (FAB, m/z) calcd. for $C_{25}H_{36}N_5O_4$ ($M^+$+1) 470.2767, observed 470.2767.

Saponification of CHP355 following the general procedure described previously afforded CHP356 as a colorless oil (25 mg, 85% yield): $^1H$ NMR (MeOH, 500 MHz) δ 0.72 (d, J=6.5 Hz, 3H), 0.76 (d, J=6.5 Hz, 3H), 0.78 (d, J=6.3 Hz, 3H), 0.86 (m, 2H), 1.36 (m, 1H), 2.10 (s, 3H), 2.61 (dd, J=14.0, 10.5 Hz, 1H), 3.33 (m, 1H), 3.87 (dd, J=14.0, 3.0 Hz, 1H), 4.00 (dd, J=9.5, 4.5 Hz, 1H), 4.05 (d, J=15.5 Hz, 1H), 4.71 (d, J=5.3 Hz, 1H), 5.18 (d, J=15.5 Hz, 1H), 7.15 (m, 5H), 7.59 (s, 1H); $^{13}C$ NMR (MeOH, 125 MHz) δ 8.88, 16.49, 20.83, 22.52, 24.71, 36.70, 37.27, 41.30, 44.00, 50.61, 53.86, 59.30, 126.87, 127.34, 127.35, 128.56, 128.56, 129.66, 129.66, 133.71, 137.83, 157.57, 169.79, 178.63; HRMS (FAB, m/z) calcd. for $C_{24}H_{34}N_5O_4$ ($M^+$+1) 456.2611, observed 456.2612.

Biological Assay In Vitro GGTase and FTase Inhibition

The in vitro inhibition assays of GGTase-1 and FTase were carried out by measuring the [$^3H$]GGPP and [$^3H$]FPP incorporated into H-Ras-CVLL and H-Ras-CVLS, respectively, as previously described.[27] The in vivo inhibition of geranylgeranylation and farnesylation was determined based on the level of inhibition of Rap1A and H-Ras processing, respectively.[10] Briefly, oncogenic H-Ras-transformed NIH 3T3 cells were treated with various concentrations of inhibitors, and the cell lysates were separated on 12.5% SDS-PAGE. The separated proteins were transferred to nitrocellulose and immunoblotted using an anti-Ras antibody (Y13-258) or an anti-Rap1A antibody (SC-65). Antibody reactions were visualized using either peroxidase-conjugated goat anti-rat IgG or goat anti-rabbit IgG and an enhanced chemiluminescence detection system. The results of those assays appear in Table 1 (FIG. 9), Table 2 (FIG. 10) and Table 3 (FIG. 11).

The results presented in FIGS. 9-11 evidence the structure activity relationships of a number of compounds according to the present invention in inhibiting GGTase. Using piperazine 2-one as a relatively rigid scaffold, a number of compounds were synthesized and tested in a well-defined arrangement to mimic the peptide sequence. High potency, exceptional selectivity and water-solubility were obtained for inhibition of GGTase-I with structures such as GGTI-2418 and GGTI-2432 (Table 3, FIG. 11) showing exceptional activity. The potency of this series of GGTIs is highly dependent on the presence of an L-leucine moiety with a free carboxyl terminus, as well as an S configuration of the 3-aryl group. The selectivity is significantly promoted by 5-methyl substitution on the imidazole ring and fluorine-substitution on the 3-aryl group. Modification of the 6-position of the piperazinone scaffold was found to be unfavorable. GGTI-2417, the corresponding methyl ester of GGTI-2418, was found to selectively block processing of Rap I A by GGCTase-1 with an $IC_{50}$ of 0.3 μM in NIH 3T3 cells. This series of compounds likely inhibit GGTase-I in a competitive manner to the CAAX tetrapeptide instead of geranylgeranylpyrophosphlate (GGPP), the universal geranylgeranyl source for all the different GGTase substrates. This suggests potentially good selectivity of this series of compounds in cell culture or in vivo systems and utility as inhibitors of GGTase and antitumor/anticancer agents, as well as a number of other disease states described herein.

In vivo Biological Activity

Geranylgeraniyltranisferase I Inhibitors Potently Inhibit A-549 Human Lung Cancer Cell Growth in Nude Mice.

Methods

Antitumor activity in the nude mouse tumor xenograft model—Nude mice (Charles River, Wilmington, Mass.) were maintained in accordance with the Institutional Animal Care and Use Committee (IACUC) procedures and guidelines. A-549 cells were harvested, resuspended in PBS and injected s.c. into the right and left flank ($7\times10^6$ cells per flank) of 8 week old female nude mice as reported previously (1, 2). When tumors reached 50 to 100 $mm^3$, animals either were implanted s.c. with 2-week osmotic mini-pumps (Alzet 2002, Alzet, Palo Alto, Calif.). The mini-pumps were implanted on the right flank and the tumor cells on the left flank. Control animals received a saline vehicle whereas treated animals were injected with either vehicle, GGTI-2154, GGTI-2418, GGTI-2432 and GGTI-2430. The tumor volumes were determined by measuring the length (l) and the width (w) and calculating the volume ($V=lw^2/2$) as described previously (30, 31).

Results

A-549 cells were implanted s.c. in nude mice and when the tumors reached an average size of about 50 to 100 $mm^3$, the animals were randomized and treated either with vehicle or peptidomimetics as described under Materials and Methods. FIGS. 12A-D show that, over a period of 28-34 days, tumors from animals that were treated with vehicle reached an average size of about 600 $mm^3$ whereas those treated with GGTI-2418 (FIG. 12A), GGTI-2132 (FIG. 12B), GGTI-2430 (FIG. 12C) and GGTI-2154 (FIG. 12D) grew to average sizes of 280, 300, 500 and 250 $mm^3$, respectively. Thus, these GGTIs inhibited A-549 tumor growth by 57%, 40%, 29% and 66%, respectively.

REFERENCES

1. Chow, M.; Der, C. J.; Buss, J. E. Structure and biological effects of lipid modification on proteins. *Curr. Opin. Cell. Biol.* 1992, 4 629-636.
2. Rowell, C. A.; Kowalczyk, J. J.; Lewis, M. D.; Garcia, A. M. Direct demonstration of geranylgeranylation and farnesylation of Ki-Ras in vivo. *J. Biol. Chem.* 1997, 272, 14093-14097.
3. Whyte, D. B.; Kirschmeier, P.; Hockenberry, T. N.; Nunez Oliva, I.; James, L.; Catino, J. J.; Bishop, W. R.; Pai, J. K. K- and N-Ras are geranylgeranylated in cells treated with farnesyl protein transferase inhibitors. *J. Biol. Chem.* 1997, 272, 14459-14464.
4. Clark, E. A.; Golub, T. R.; Lander, E. C.; Hynes, R. O. Genomic Analysis of Metastasis Reveals an Essential Role for RhoC. *Nature* 2000, 406, 532-535.
5. Zohn, I. M.; Campbell, S. L.; Khosravi-Far, R.; Rossman, K. I.; Der, C. J. Rho family proteins and Ras transformation: the RHOad less traveled gets congested. *Oncogene,* 1998, 17, 1415-1438.
6. Sebti, S. M.; Hamilton, A. D. Farnesyltransferase and geranylgeranyltransferase-I inhibitors and cancer therapy: lessons from mechanism and bench-to-bedside translational studies. *Oncogene,* 2000, 19, 6584-6593.
7. Aznar, S.; Lacal, J. C. Rho signals to cell growth and apoptosis. *Cancer Letters,* 2001, 165, 1-10.

8. Whitehead, I. P.; Zohn, I. E.; Der, C. J. Rho GTPase-dependent transformation by G-protein-coupled receptors. *Oncogene*, 2001, 20, 1547-1555.
9. Sun, J.; Blaskovich M. A.; Knowles, D.; Qian, Y.; Ohkanda, J.; Bailey, R. D.; Hamilton, A. D.; Sebti, S. M. Antitumor efficacy of a novel class of non-thiol-containing peptidomimetic inhibitors of farnesyltransferase and geranylgeranyltransferase I: Combination therapy with the cytotoxic agents cisplatin, taxol, and gemcitabine. *Cancer Res*. 1999, 59, 4919-4926.
10. Sun, J.; Qian Y.; Hamilton, A. D.; Sebti, S. M. Both farnesyltransferase and geranylgeranyltransferase I inhibitors are required for inhibition of oncogellic K-as prenylation but each alone is sufficient to suppress human tumor growth in nude mouse xenografts *Oncogene*, 1998, 16 1467-1473.
11. Sun, J.; Qian, Y.; Chen, Z.; Marfurt, J.; Hamilton, A. D.; Sebti, S. M. The geranylgeranyltransferase I inhibitor GGTI-298 induces hypophosphorylation of retinoblastoma and partner switching of cyclin-dependent kinase inhibitors—A potential mechanism for GGTI-298 antitumor activity. *J. Biol. Chem*. 1999, 274, 6930-6934.
12. Macchia, M.; Jannitti, N.; Gervasi, G.; Danesi, R. Geranylgeranyl diphosphate-based inhibitors of post-translational geranylgeranylation of cellular proteins. *J. Med. Chem*. 1996, 39, 1352-1356.
13. Zahn, T. J.; Whitney, J.; Weinbaum, C.; Gibbs, R. A. Synthesis and evaluation of GGPP geometric isomers: divergent substrate specificities of FTase and GGTase I. *Bioorg. Med. Chem. Lett*. 2001, 11 1605-1608.
14. Huber, H. E. Robinson, R. G.; Warkins, A.; Nahas, D. D.; Abrams, M. T.; Buser, C. A.; Lobell, R. B.; Patric, D.; Anthony, N. J.; Dinsmore, C. J.; Graham, S. L.; Hartman, G. D.; Lumma, W. C.; Williams, T. M.; Heimbrook, D. C. Anions modulate the potency of geranylgeranyl-protein transferase I inhibitors. *J. Biol. Chem*. 2001, 27, 24457-24465.
15. Graham, S. L.; deSolms, S. J.; Giuliani, E. A.; Kohl, N. E.; Mosser, S. D.; Oliff, A. I.; Pompliano, D. L.; Rands, E.; Breslin, M. J.; Deana, A. A.; Garsky, V. M.; Scholz, T. H.; Gibbs, J. B.; Smith, R. L. Pseudopeptide inhibitors of Ras farnesyl-protein transferase. *J. Med. Chem*. 1994, 37, 725-732.
16. Qian, Y. M., Vogt, A.; Vasudevan, A.; Sebti, S. M.; Hamilton, A. D. Selective inhibition of type-I geranylgeranyltransferase in vitro and in whole cells by CAAL peptidomimetics. *Bioorg. Med. Chem*. 1998, 6, 293-299.
17. Vasudevan, A; Qian, Y. M.; Vogt, A.; Blaskovich, M. A.; Ohkanda, J.; Sebti, S. M.; Hamilton, A. D. Potent, highly selective, and non-thiol inhibitors of protein geranylgeranyltransferase-I, *J. Med. Chem*. 1999, 42, 1333-1340.
18. Berman, J. M.; Abrams, M. T.; David, J. P.; Greenberg, I. B.; Robinson, R. G.; Buser, C. A.; Huber, H. E.; Koblan, K. S.; Kohl, N. E.; Lobell, R. B.; Graham, S. L.; Hartman, G. D.; Williams, T. M.; Dinsmore, C. J. Aryloxy substituted N-arylpiperazinone as dual inhibitors of farnesyltrasferase and geranylgeranyltransferase-I. *Bioorg. Med. Chem. Lett*. 2001, 1411-1415.
19. DiMaio J. Belleau, B. Synthesis of chiral piperazine-2-ones as model peptidomimetics. *J. Chem. Soc. Perkin Trans*. 11989, 1687-1689.
20. A similar observation was seen in all 4-N-Cbz-protected piperazillone derivatives, which resulted in fractional proton integration in the $^1$H NMR of these compounds. Two representative $^1$H NMR spectra are included for compounds 12a and 16 in the supporting information.
21. Hunt, J. T.; Lee, V. G.; Leftheris, K.; Seizinger, B.; Carboni, J.; Mabus, J.; Ricca, C.; Yan, N.; Manne, V. Potent, cell active, non-thiol tetrapeptide inhibitors of farnesyltransferase. *J. Med. Chem*. 1996, 39, 353-358.
22. Sellier, C.; Buschauer, A.; Elz, S.; Schunack, W.; *Liebigs Ann. Chem*. Zur Synthese von (Z)-und (E)-3-(1H-Imidazol-4-yl)-2-propenamin und einigen 3-(1H-Imidazol-4-yl) propanaminen. 1992, 317-324.
23. Matsui, T.; Sugiura, T.; Nakai, H.; Iguchi, S.; Shigeoka, S. Takada, H.; Odagaki, Y.; Nagao, Y.; Ushio, Y.; Ohmoto, K., Iwmara, H.; Yamazaki, S.; Arai, Y.; Kawamura, M. Novel 5-HT3 antagonists-isoquinolinones and 3-aryl-2-pyridones. *J. Med. Chem*. 1992, 35, 3307-3319.
24. Yamashita, T.; Tsuru, E.; Banjyo, E.; Doe, M.; Shibata, K.; Yasuda, M.; Gemba, M. Synthesis and opiate activity of pseudo-tetrapeptides containing chiral piperazine-2-one and piperazine derivatives. *Chem. Pharm. Bull*. 1997, 45, 1940-1944.
25. All protons were assigned using $^1$H—$^1$H COSEY, the axial H-5 and equatorial H-5 were assigned and differentiated by their correlation and coupling pattern. NOE was observed between axial H-5 and one of the H-7 protons in the NOSEY spectrum. The 2D NMR spectra of compound 25 are included in the supporting information.
26. Hoffman, R. W. Flexible molecules with defined shape-conformational design. *Angew. Chem. Int. Ed. Engl*. 1992, 31 1124-1134, and references cited therein.
27. Vogt, A.; Qian, Y.; McGuire, T. F.; Blaskovich, M. A.; Hamilton, A. D.; Sebti, S. M. Protein geranylgeranylation, not farnesylation, is required for G1 to S phase transition in mouse fibroblasts. *Oncogene* 1996, 13, 1991-1999.
28. Strickland, C. L.; Windsor, W. T.; Syto, R.; Wang, L.; Bond, R.; Wu, Z.; Schwartz, J.; Le, H. V.; Beese, L. S.; Weber, P. C. Crystal structure of farnesyl protein transferase complexed with a CaaX peptide and farnesyl diphosphate analogue. *Biochemistry*, 1998, 37, 16601.
29. Nowick, J. S.; Powell, N. A.; Nguyen, T. M.; Noronha, G. An improved method for the synthesis of enantiomerically pure amino acid ester isocyanates. *J. Org. Chem*. 1992, 57, 7364-7366.
30. Sun, J., Qian, Y. Hamilton, A. D., and Sebti, S. M. Both farnesytranisferase and geranylgeranyltransferase I inhibitors are required for inhibition of oncogenic K-Ras prenylation but each alone is sufficient to suppress human tumor growth in nude mouse xenografts. Oncogene, 16(11): 1467-1473, 1998.
31. Sun, J., Qian, Y., Hamilton, A. D. and Sebti, S. M. Ras CAAX peptidomimetic FTI-276 selectively blocks in nude mice the growth of a human lung carcinoma with a K-Ras mutation and a p53 deletion. Cancer Research, 55: 4243-4247, 1995.

The invention claimed is:

1. The compound according to the structure:

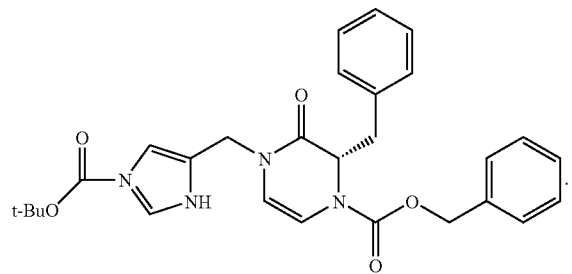

2. A compound according to the structure:

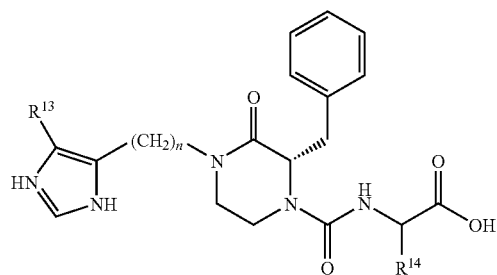

where n is 1-3;
$R^{13}$ is H or $CH_3$; and
$R^{14}$ is a group according to the structure:

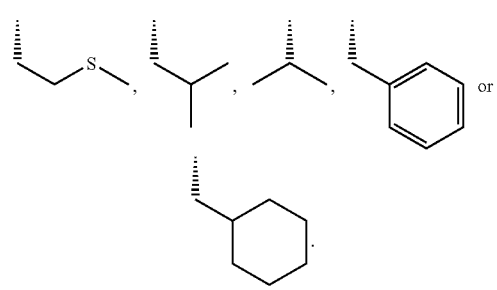

3. The compound according to claim 2 wherein $R^{14}$ is

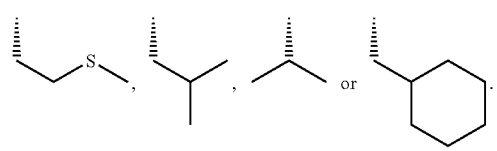

4. The compound according to claim 3 wherein $R^{13}$ is H.
5. The compound according to claim 3 wherein $R^{13}$ is $CH_3$.
6. The compound according to claim 3 wherein n is 3, $R^{13}$ is H and $R^{14}$ is

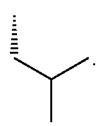

7. A compound according to the structure:

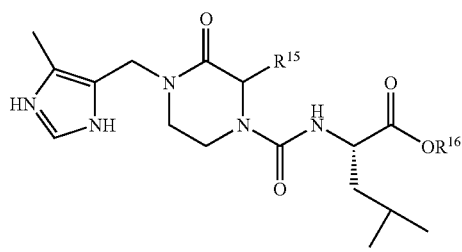

where $R^{16}$ is H or $CH_3$; and $R^{15}$ is

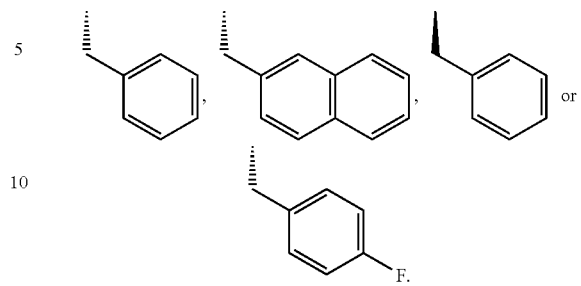

8. The compound according to claim 7 wherein $R^{15}$ is

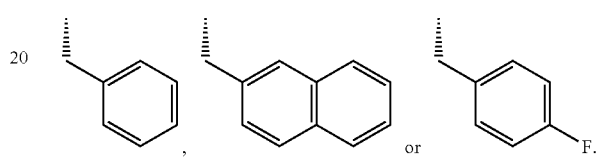

9. A pharmaceutical composition comprising an effective amount of at least one compound according to claim 6, in combination with a pharmaceutically acceptable additive, carrier or excipient.

10. A method of inhibiting GGTase I enzyme in a mammal comprising administering to said mammal an effective amount of a compound according to claim 6 to reduce the activity of GGTase I by at least about 100 fold.

11. A compound according to the formula:

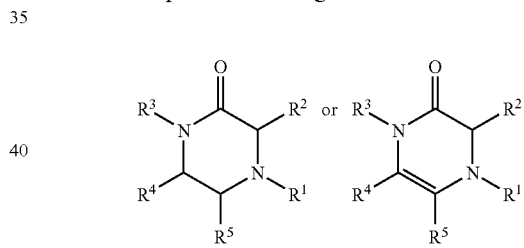

where $R^1$ is a

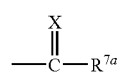

group wherein X is O or S, and $R^{7a}$ is

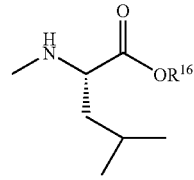

wherein $R^{16}$ is Na or H;
$R^3$ is a $C_5$-$C_{15}$ alkyl or alkenyl group, an aryl, heterocycle, alkylenearyl, alkenylenearyl, alkyleneheterocycle or alkenylene heterocycle group, wherein said alkylene, alkenylene, aryl or heterocycle group may be unsubstituted or substituted, a $C_2$-$C_{10}$ ether or thioether group, a COR, $CO_2R$, COSR, $(CH_2)_nCOR$, $(CH_2)_nCO_2R$ or $(CH_2)_nCOSR$ group, where R is H, a $C_1$-$C_{10}$ alkyl or alkenyl group, an unsubstituted or substituted aryl, a heterocycle group, an alkylenearyl, alkenylene aryl, alkyleneheterocycle or alkenyleneheterocycle group, wherein said alkylene, alkenylene, aryl or heterocycle group is unsubstituted or substituted, or a thioether group containing from 2 to 8 carbon atoms a

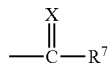

group, where X is O or S, $R^7$ is a $C_1$-$C_{10}$ alkyl, alkenyl, ether or thioether group, an aryl or heterocycle group, an alkylenearyl, alkenylenearyl, alkyleneheterocycle or alkenylene heterocycle group, which may be unsubstituted or substituted, wherein said alkylene or alkenylene group, an amine or alkyleneamine group which may be unsubstituted or substituted on the alkylene group or unsubstituted or mono- or disubstituted on the amine group with a $C_1$-$C_4$ alkyl or alkanol group, an amino acid residue or amino ester wherein the amine of said amino acid residue or amino ester is chemically bonded to the carbon of the

group, or a

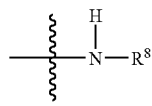

group,
wherein $R^8$ is H, a $C_1$-$C_{10}$ alkyl or alkenyl group, an aryl, heterocycle, alkylene aryl or alkyleneheterocycle group, which may be unsubstituted or substituted or an alkylene ester group

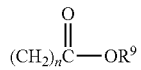

where n is 1-4 and said alkylene group of said alkylene ester may be substituted by a group $R^{10}$, where $R^9$ is a $C_1$-$C_6$ alkyl group and $R^{10}$ is a $C_1$-$C_8$ alkyl, alkenyl, ether or thioether group, an aryl, heterocycle, alkylenearyl, alkenylenearyl, alkyleneheterocycle or alkenylene heterocycle group, wherein said alkylene, alkenylene, aryl or heterocycle may be unsubstituted or substituted, with the proviso that $R^3$, but not $R^1$, may also represent an amino acid residue or amino ester wherein the amine group of said amino acid residue or amino ester forms the amine in the position alpha to the ketone in the pyrazinone ring;

$R^2$, $R^4$ and $R^5$ are each independently H, a $C_1$-$C_{15}$ alkyl or alkenyl group, $CF_3$, F, Cl, Br, I, CN, $NO_2$, $NH_2$, $NHR_1$, $NR_1R_1$, COR, $OR_1$, an aryl, heterocycle, alkylenearyl, alkenylenearyl, alkyleneheterocycle or alkenylene heterocycle group wherein said alkylene, alkenylene, aryl or heterocycle group may be unsubstituted or substituted, a $C_2$-$C_{10}$ ether or thioether group, a $CO_2R$) or $COSR_1$ where $R_1$ is H, a $C_1$-$C_{10}$ alkyl or alkenyl group, an unsubstituted or substituted aryl or heterocycle group, an alkylenearyl, alkenylene aryl, alkyleneheterocycle or alkenylene heterocycle group, wherein said alkylene, alkenylene, aryl or heterocycle group is unsubstituted or substituted, a thioether group containing from 2 to 8 carbon atoms, or a

group, where $R_3$ is H, a $C_1$-$C_{10}$ alkyl, alkenyl, ether or a thioether group, with the proviso that at least one of $R^2$, $R^4$ and $R^5$ is H;
said compound including all isomeric mixtures, isolated stereoisomers, geometric isomers and optical isomers thereof, or a pharmaceutically acceptable salt thereof.

12. A compound according to the formula:

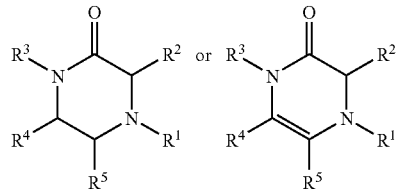

where $R^1$ is a

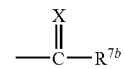

group wherein X is O or S, and $R^{7b}$ is

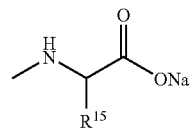

wherein $R^{15}$ is a group according to the structure:

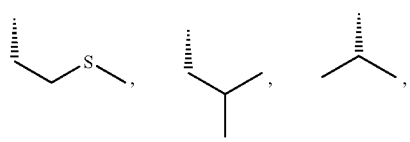

-continued

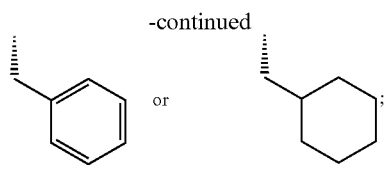

$R^3$ is a $C_5$-$C_{15}$ alkyl or alkenyl group, an aryl, heterocycle, alkylenearyl, alkenylenearyl, alkyleneheterocycle or alkenylene heterocycle group, wherein said alkylene, alkenylene, aryl or heterocycle group may be unsubstituted or substituted, a $C_2$-$C_{10}$ ether or thioether group, a COR, $CO_2R$, COSR, $(CH_2)_n$COR, $(CH_2)_n$$CO_2R$ or $(CH_2)_n$COSR group, where R is H, a $C_1$-$C_{10}$ alkyl or alkenyl group, an unsubstituted or substituted aryl, a heterocycle group, an alkylenearyl, alkenylene aryl, alkyleneheterocycle or alkenyleneheterocycle group, wherein said alkylene, alkenylene, aryl or heterocycle group is unsubstituted or substituted, or a thioether group containing from 2 to 8 carbon atoms a

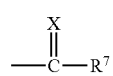

group, where X is O or S, $R^7$ is a $C_1$-$C_{10}$ alkyl, alkenyl, ether or thioether group, an aryl or heterocycle group, an alkylenearyl, alkenylenearyl, alkyleneheterocycle or alkenylene heterocycle group, which may be unsubstituted or substituted, wherein said alkylene or alkenylene group, an amine or alkyleneamine group which may be unsubstituted or substituted on the alkylene group or unsubstituted or mono- or disubstituted on the amine group with a $C_1$-$C_4$ alkyl or alkanol group, an amino acid residue or amino ester wherein the amine of said amino acid residue or amino ester is chemically bonded to the carbon of the

group, or a

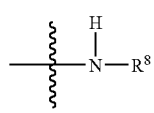

group,
wherein $R^8$ is H, a $C_1$-$C_{10}$ alkyl or alkenyl group, an aryl, heterocycle, alkylene aryl or alkyleneheterocycle group, which may be unsubstituted or substituted or an alkylene ester group

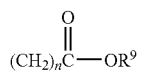

where n is 1-4 and said alkylene group of said alkylene ester may be substituted by a group $R^{10}$, where $R^9$ is a $C_1$-$C_6$ alkyl group and $R^{10}$ is a $C_1$-$C_8$ alkyl, alkenyl, ether or thioether group, an aryl, heterocycle, alkylenearyl, alkenylenearyl, alkyleneheterocycle or alkenylene heterocycle group, wherein said alkylene, alkenylene, aryl or heterocycle may be unsubstituted or substituted, with the proviso that $R^3$, but not $R^1$, may also represent an amino acid residue or amino ester wherein the amine group of said amino acid residue or amino ester forms the amine in the position alpha to the ketone in the pyrazinone ring;

$R^2$, $R^4$ and $R^5$ are each independently H, a $C_1$-$C_{15}$ alkyl or alkenyl group, $CF_3$, F, Cl, Br, I, CN, $NO_2$ $NH_2$, $NHR_1$, $NR_1R_1$, COR, $OR_1$, an aryl, heterocycle, alkylenearyl, alkenylenearyl, alkyleneheterocycle or alkenylene heterocycle group wherein said alkylene, alkenylene, aryl or heterocycle group may be unsubstituted or substituted, a $C_2$-$C_{10}$ ether or thioether group, a $CO_2R$) or $COSR_1$ where $R_1$ is H, a $C_1$-$C_{10}$ alkyl or alkenyl group, an unsubstituted or substituted aryl or heterocycle group, an alkylenearyl, alkenylene aryl, alkyleneheterocycle or alkenylene heterocycle group, wherein said alkylene, alkenylene, aryl or heterocycle group is unsubstituted or substituted, a thioether group containing from 2 to 8 carbon atoms, or a

group, where $R_3$ is H, a $C_1$-$C_{10}$ alkyl, alkenyl, ether or a thioether group, with the proviso that at least one of $R^2$, $R^4$ and $R^5$ is H;

said compound including all isomeric mixtures, isolated stereoisomers, geometric isomers and optical isomers thereof, or a pharmaceutically acceptable salt thereof.

13. The compound according to any of claims 11-12, wherein $R^2$ is a group according to the structure:

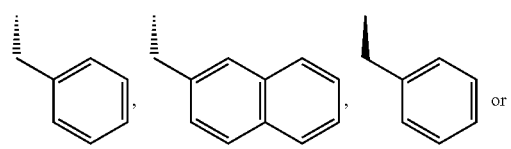

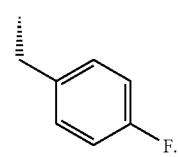

14. The compound according to any of claims 11-12, wherein $R^3$ is a group according to the structure:
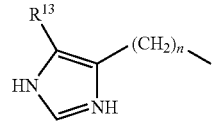
where n is 1-3; and
$R^{13}$ is H, CH$_3$, or
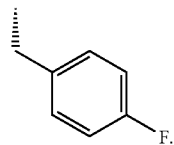
15. A pharmaceutical composition comprising an effective amount of at least one compound according to any of claims 11-14, in combination with a pharmaceutically acceptable additive, carrier or excipient.
* * * * *